(12) United States Patent
Turner et al.

(10) Patent No.: US 10,392,379 B2
(45) Date of Patent: Aug. 27, 2019

(54) HEPATITIS B CORE PROTEIN MODULATORS

(71) Applicants: Assembly Biosciences, Inc., Carmel, IN (US); INDIANA UNIVERSITY RESEARCH AND TECHNOLOGY CORPORATION, Indianapolis, IN (US)

(72) Inventors: William Turner, Bloomington, IN (US); Lee Daniel Arnold, Bloomington, IN (US); Hans Maag, Kleires Wiesental (DE); Mark Bures, Carmel, IN (US)

(73) Assignees: Assembly Biosciences, Inc., Carmel, IN (US); Indiana University Research And Technology Corporation, Indianapolis, IN (US)

( * ) Notice: Subject to any disclaimer, the term of this patent is extended or adjusted under 35 U.S.C. 154(b) by 0 days.

(21) Appl. No.: 15/760,343

(22) PCT Filed: Sep. 15, 2016

(86) PCT No.: PCT/US2016/051940
§ 371 (c)(1),
(2) Date: Mar. 15, 2018

(87) PCT Pub. No.: WO2017/048954
PCT Pub. Date: Mar. 23, 2017

(65) Prior Publication Data
US 2018/0273520 A1 Sep. 27, 2018

Related U.S. Application Data

(60) Provisional application No. 62/218,815, filed on Sep. 15, 2015.

(51) Int. Cl.
| | | |
|---|---|---|
| C07D 243/38 | (2006.01) |
| C07D 267/20 | (2006.01) |
| C07D 281/16 | (2006.01) |
| C07D 401/12 | (2006.01) |
| C07D 403/12 | (2006.01) |
| C07D 417/12 | (2006.01) |
| C07D 417/14 | (2006.01) |
| C07D 453/02 | (2006.01) |
| C07D 471/04 | (2006.01) |
| A61K 45/06 | (2006.01) |
| A61P 31/20 | (2006.01) |
| C07D 413/12 | (2006.01) |

(52) U.S. Cl.
CPC .......... *C07D 417/12* (2013.01); *A61K 45/06* (2013.01); *A61P 31/20* (2018.01); *C07D 243/38* (2013.01); *C07D 267/20* (2013.01); *C07D 281/16* (2013.01); *C07D 401/12* (2013.01); *C07D 403/12* (2013.01); *C07D 413/12* (2013.01); *C07D 417/14* (2013.01); *C07D 453/02* (2013.01); *C07D 471/04* (2013.01)

(58) Field of Classification Search
None
See application file for complete search history.

(56) References Cited

U.S. PATENT DOCUMENTS

| | | |
|---|---|---|
| 5,512,563 A | 4/1996 | Albright et al. |
| 8,618,090 B2 | 12/2013 | Desai et al. |
| 9,399,619 B2 | 7/2016 | Guo et al. |
| 9,873,684 B2 | 1/2018 | Kahraman et al. |
| 2007/0105819 A1 | 5/2007 | Olsson et al. |
| 2015/0368261 A1 | 12/2015 | Demin et al. |
| 2017/0107185 A1 | 4/2017 | Grammneos et al. |
| 2017/0267685 A1 | 9/2017 | D'Agostino et al. |

FOREIGN PATENT DOCUMENTS

| | | | |
|---|---|---|---|
| CL | 2015002706 A1 | 4/2016 |
| CL | 2015003456 A1 | 7/2016 |
| CL | 20105002628 | 8/2016 |
| CL | 2016003175 A1 | 8/2017 |
| GB | 1480553 A | 7/1977 |
| JP | 58225074 | 12/1983 |
| WO | WO-92/19277 A1 | 11/1992 |
| WO | WO-2005/072741 A1 | 8/2005 |
| WO | WO-2008/036139 A3 | 12/2008 |
| WO | WO-2008/118141 A3 | 12/2008 |
| WO | WO-2010/011537 A1 | 1/2010 |
| WO | WO-2012/045194 A1 | 4/2012 |
| WO | WO-2013/006394 A1 | 1/2013 |
| WO | WO-2015/017412 A1 | 2/2015 |
| WO | WO 2015/138895 * | 9/2015 | ............. A01N 43/00 |
| WO | WO-2015/138895 A1 | 9/2015 |

OTHER PUBLICATIONS

Supplemental European Search Report issued by the European Patent Office (Munich), dated Apr. 11, 2018, for related Application No. EP 15761201; 21 pages.

Takeda, M., et al., "Synthesis of Dibenzo [b,e] [1,4] Diazepine Derivatives as Anti-depressants," Yakugaku Zahhi, vol. 89, No. 2, (1969), 6 pages.

National Center for Biotechnology Information, PubChem Compound Database; CID-4152425, XP-002779931, modified Apr. 7, 2017, created Sep. 13, 2005; 3 pages.

National Center for Biotechnology Information, PubChem Compound Database; CID-46260649, XP-002779932, modified Apr. 7, 2017, created Jul. 21, 2010; 3 pages.

National Center for Biotechnology Information, PubChem Compound Database; CID-4163919, XP-002779933, modified Apr. 7, 2018, created Sep. 13, 2005; 3 pages.

National Center for Biotechnology Information, PubChem Compound Database; CID-4167865, XP-002779934, modified Apr. 7, 2018, created Sep. 13, 2005; 3 pages.

(Continued)

*Primary Examiner* — Alicia L Otton
(74) *Attorney, Agent, or Firm* — Goodwin Procter LLP

(57) ABSTRACT

The present disclosure provides, in part, compounds having allosteric effector properties against Hepatitis B virus Cp. Also provided herein are methods of treating viral infections, such as hepatitis B, comprising administering to a patient in need thereof a disclosed compound.

16 Claims, No Drawings

(56) References Cited

OTHER PUBLICATIONS

National Center for Biotechnology Information, PubChem Compound Database; CID-4338109, XP-002779935, modified Apr. 7, 2018, created Sep. 14, 2005; 3 pages.
National Center for Biotechnology Information, PubChem Compound Database; CID-4163918, XP-002779936, modified Apr. 7, 2018, created Sep. 13, 2005; 3 pages.
National Center for Biotechnology Information, PubChem Compound Database; CID-3576843, XP-002779937, modified Apr. 7, 2018, created Sep. 9, 2005; 3 pages.
National Center for Biotechnology Information, PubChem Compound Database; CID-4577044, XP-002779938, modified Apr. 7, 2018, created Sep. 15, 2005; 3 pages.
National Center for Biotechnology Information, PubChem Compound Database; CID-4097179, XP-002779940, modified Apr. 7, 2018, created Sep. 13, 2005; 3 pages.
National Center for Biotechnology Information, PubChem Compound Database; CID-23797169, XP-002779941, modified Apr. 7, 2018, created Feb. 20, 2008; 3 pages.
National Center for Biotechnology Information, PubChem Compound Database; CID-53384785, XP-002779942, modified Apr. 7, 2018, created Oct. 13, 2011; 3 pages.
National Center for Biotechnology Information, PubChem Compound Database; CID-20885138, XP-002775927, modified Nov. 18, 20187, created Dec. 5, 2007; 3 pages.
National Center for Biotechnology Information, PubChem Compound Database; CID-20885146, XP-002775928, modified Nov. 18, 2017, created Dec. 5, 2007; 3 pages.
National Center for Biotechnology Information, PubChem Compound Database; CID-20885149, XP-002775929, modified Nov. 18, 2017, created Dec. 5, 2007; 3 pages.
National Center for Biotechnology Information, PubChem Compound Database; CID-20885150, XP-002775930, modified Nov. 18, 2017, created Dec. 5, 2007; 3 pages.
National Center for Biotechnology Information, PubChem Compound Database; CID-20885171, XP-002775931, modified Nov. 18, 2017, created Dec. 5, 2007; 3 pages.
Letter Exam Report from the Australian Patent Office, dated May 6, 2018, for Australian Application No. 2015229174; 6 pages.
Office Action issued by the Belize Intellectual Property Office, dated May 18, 2018, for Belize Patent Application No. 887.16; 2 pages.
English translation of the First Official Action issued by the Mexican Patent Office for Mexican Patent Application No. MX/a/2016/011800, Jul. 4, 2018; 3 pages.
Letter dated Jun. 27, 2018 regarding Examination Report issued by the National Office of Industrial Property for Dominican Republic Patent Application No. P2016-0233; 2 pages.
Supplemental Partial European Search Report issued by the European Patent Office (Munich), dated Nov. 23, 2017, for related Application No. EP 15761201; 14 pages.
Letter Exam Report issued by the Patent Office of the People's Republic of China (translated in English language), dated Jun. 29, 2018, for Chinese Application No. 201580024580.0; (3 pages).
Letter Exam Report issued by the Chilean Patent Office, dated Jun. 12, 2018, for Chilean Application No. 2269-2016; 15 pages.
National Center for Biotechnology Information, PubChem Compound Database; CID-23734106, XP-002779939, modified Apr. 7, 2018, created Feb. 20, 2008; 3 pages.
Hall, Pamela R., et al., "*Small molecule inhibitors of hantavirus infection*,"Bioorganic & Medicinal Chemistry Letters, vol. 20, (2010), pp. 7085-7091.
Xiao, et al., "Discovery, Optimization, and Characterization of Novel D2 Dopamine Receptor Selective Antagonists," Journal of Medicinal Chemistry, Mar. 25, 2014, vol. 57, pp. 3450-3463.
International Preliminary Report on Patentability issued by the International Bureau of WIPO, dated Sep. 13, 2016, for International Application No. PCT/US2015/020444; 6 pages.
International Search Report and Written Opinion issued by the ISA/US, Commissioner for Patents, dated Jul. 6, 2015, for International Application No. PCT/US2015/020444; 10 pages.
National Center for Biotechnology Information. PubChem Compound Database; CID=20885151; available at https://pubchem.ncbi.nlm.nih.gov/compound/20885151 (accessed Sep. 13, 2016; deposit date Dec. 5, 2007); 10 pages.
National Center for Biotechnology Information. PubChem Compound Database; CID=4 II 9 I71, available at https://pubchem.ncbi.nlm.nih.gov/compound/4119171 (accessed Sep. 13, 2016; deposit date Sep. 3, 2005); 12 pages.
National Center for Biotechnology Information. PubChem Compound Database; CID=4167865, https://pubchem.ncbi.nlm.nih.gov/compound/4167865 (accessed Sep. 13, 2016; deposit date Sep. 13, 2005); 12 pages.
International Preliminary Report on Patentability dated Mar. 20, 2018, for International Application No. PCT/US2016/051934 (6 pages).
International Search Report and Written Opinion dated Dec. 29, 2016 for International Application No. PCT/US16/51934.
International Preliminary Report on Patentability dated Dec. 29, 2016, for International Application No. PCT/US2016/051949.
International Search Report and Written Opinion dated Dec. 29, 2016 for International Application No. PCT/US16/51949.
International Preliminary Report on Patentability dated Oct. 28, 2016, for International Application No. PCT/US2016/051940.
International Search Report and Written Opinion dated Oct. 28, 2016 for International Application No. PCT/US16/51949.
National Center for Biotechnology Information, PubChem Compound Database; CID-201327, create date: Aug. 9, 2005; 3 pages.
Supplementary European Search Report issued for EP16847298, dated Jan. 28, 2019 (6 pages).
Notice of Reasons for Rejection issued for Japanese Patent Application No. 2016-557019, dated Oct. 30, 2018 (6 pages).
Official Office Action issued in Eurasian application No. 201890731, dated Oct. 31, 2018.
Office Action issued by the Belize Intellectual Property Office, dated Nov. 21, 2018, for Belize Patent Application No. 925.18 (3 pages).
Extended European Search Report issued in EP16847298.3, dated Jan. 2, 2019.

\* cited by examiner

HEPATITIS B CORE PROTEIN MODULATORS

CROSS REFERENCE TO RELATED APPLICATION

The present application is a U.S. National Phase Application under 35 U.S.C. § 371 of International Application PCT/US2016/051940, filed Sep. 15, 2016, which claims priority to U.S. Provisional Application 62/218,815, filed Sep. 15, 2015, hereby incorporated by reference in its entirety.

BACKGROUND

Hepatitis B (HBV) causes viral Hepatitis that can further lead to chronic liver disease and increase the risk of liver cirrhosis and liver cancer (hepatocellular carcinoma). Worldwide, about 2 billion people have been infected with HBV, around 360 million people are chronically infected, and every year HBV infection causes more than one half million deaths (2009; WHO, 2009). HBV can be spread by body fluids: from mother to child, by sex, and via blood products. Children born to HBV-positive mothers may also be infected, unless vaccinated at birth.

The virus particle is composed of a lipid enveloped studded with surface protein (HBsAg) that surrounds the viral core. The core is composed of a protein shell, or capsid, built of 120 core protein (Cp) dimers, which in turn contains the relaxed circular DNA (rcDNA) viral genome as well as viral and host proteins. In an infected cell, the genome is found as a covalently closed circular DNA (cccDNA) in the host cell nucleus. The cccDNA is the template for viral RNAs and thus viral proteins. In the cytoplasm, Cp assembles around a complex of full-length viral RNA (the so-called pregenomic RNA or pgRNA and viral polymerase (P). After assembly, P reverse transcribes the pgRNA to rcDNA within the confines of the capsid to generate the DNA-filled viral core. For convenience, we divide the assembly process at the point of capsid assembly and pgRNA-packaging. Steps preceding this event are "upstream"; steps following RNA-packaging are "downstream".

At present, chronic HBV is primarily treated with nucleos(t)ide analogs (e.g. entecavir) that suppress the virus while the patient remains on treatment but do not eliminate the infection, even after many years of treatment. Once a patient starts taking nucleotide analogs most must continue taking them or risk the possibility of a life threatening immune response to viral rebound. Further, nucleos(t)ide therapy may lead to the emergence of antiviral drug resistance (Deres and Rubsamen-Waigmann, 1999; Tennant et al., 1998; Zhang et al., 2003) and—in rare patients—adverse events have been reported (Ayoub and Keeffe, 2011).

The only FDA approved alternative to nucleos(t)ide analogs is treatment with interferon α or pegylated interferon α. Unfortunately, the adverse event incidence and profile of interferon α can result in poor tolerability, and many patients are unable to complete therapy. Moreover, only a small percentage of patients are considered appropriate for interferon therapy, as only a small subset of patients are likely to have a sustained clinical response to a course of interferon therapy. As a result, interferon based therapies are used in only a small percentage of all diagnosed patients who elect for treatment.

Thus, current HBV treatments can range from palliative to watchful waiting. Nucleos(t)ide analogs suppress virus production, treating the symptom, but leave the infection intact. Interferon α has severe side effects and less tolerability among patients and is successful as a finite treatment strategy in only a small minority of patients. There is a clear on-going need for more effective treatments for HBV infections.

SUMMARY

Provided herein are compounds that can have properties such as those described below,
where the compounds in some embodiments may be represented by:

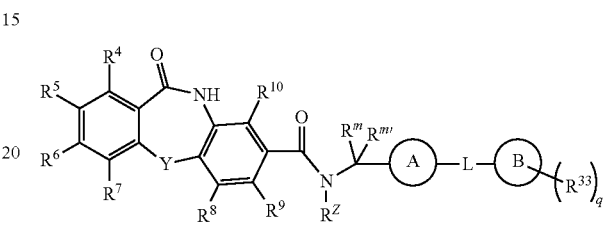

wherein
$R^4$, $R^5$, $R^6$, $R^7$, $R^8$, $R^9$, $R^{10}$, $R^m$, $R^{m'}$, $R^{33}$, $R^Z$, A, B, L and q are defined herein. Also provided herein are methods of treating viral infections, such as hepatitis B, comprising administering to a patient a disclosed compound.

For example, the present disclosure is directed in part to compounds having allosteric effector properties against Hepatitis B virus Cp, a protein found as a dimer, a multimer, and as the protein shell of the HBV core. Without being bound by theory, disclosed compounds may ultimately target multimerization of viral core proteins, which is central to HBV infection, where the core protein multimerizes into shell, or capsid, and/or disclosed compounds may for example, ultimately target interaction of viral core proteins with other macromolecules, such as host or viral nucleic acid, host proteins, or other viral proteins. For example, disclosed compounds may be considered in some embodiments CpAM—core protein allosteric modifiers. CpAM interaction with core protein can allosterically favor an assembly-active form of Cp dimer and lead to viral capsid assembly at an inappropriate time or place or lead to non-standard intersubunit interactions, all resulting in defective capsids. CpAMs may additionally or alternatively affect steps of "upstream" of capsid assembly by altering the concentrations or nature of Cp available as dimer as compared to capsid or other multimeric forms. Disclosed compounds or CpAMs may, in some embodiments, noticeably affect functions upstream of viral assembly such as modulation of cccDNA transcription, RNA stability and/or protein-protein interactions.

DETAILED DESCRIPTION

The features and other details of the disclosure will now be more particularly described. Before further description of the present invention, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

As intended herein, the terms "a" and "an" include singular as well as plural references unless the context clearly dictates otherwise. For example, the term "an assembly effector" can include one or more such effectors.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The terms "cycloalkyl" or a "carbocyclic group" as used herein refers to a saturated or partially unsaturated hydrocarbon group of, for example, 3-6, or 4-6 carbons, referred to herein as $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine etc.

The terms "heterocyclyl" or "heterocyclic group" are art-recognized and refer to saturated or partially unsaturated 4-7 membered ring structures, whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran etc The terms "hydroxy" and "hydroxyl" as used herein refers to the radical —OH.

"Treatment" as used herein includes the alleviation, prevention, reversal, amelioration or control of a pathology, disease, disorder, process, condition or event, including viral infection. In this context, the term "treatment" is further to be understood as embracing the use of a drug to inhibit, block, reverse, restrict or control progression of viral infection.

As used herein, the term "pharmaceutical composition" refers to compositions of matter comprising at least one pharmaceutical compound and optionally a pharmaceutically acceptable carrier.

As used herein, the term "pharmaceutical compound" or "drug" refers to a free compound, its therapeutically suitable salts, solvates such as hydrates, specific crystal forms of the compound or its salts, or therapeutically suitable prodrugs of the compound.

Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ═ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z"

or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the invention may have one or more H atom replaced with deuterium.

Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the examples herein by substituting an isotopically labeled reagent for a non-isotopically labeled reagent.

The term "therapeutically suitable salt," refers to salts or zwitterions of pharmaceutical compounds which are water or oil-soluble or dispersible, suitable for treatment of disorders and effective for their intended use. The salts may be prepared, for instance, during the final isolation and purification of the compounds or separately by reacting an amino group of the compounds with a suitable acid. For example, a compound may be dissolved in a suitable solvent, such as but not limited to methanol and water, and treated with at least one equivalent of an acid, for instance hydrochloric acid. The resulting salt may precipitate out and be isolated by filtration and dried under reduced pressure. Alternatively, the solvent and excess acid may be removed under reduced pressure to provide the salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, form ate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of a compound may also be quaternized with alkyl chlorides, bromides, and iodides such as methyl, ethyl, propyl, isopropyl, butyl, lauryl, myristyl, stearyl, and the like.

Basic addition salts may be prepared, for instance, during the final isolation and purification of pharmaceutical compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts may derived, for example, from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like.

The term "therapeutically suitable prodrug," refers to those prodrugs or zwitterions which are suitable for use in contact with the tissues of subjects and are effective for their intended use. The term "prodrug" refers to compounds that are transformed in vivo to a pharmaceutical compound, for example, by hydrolysis in blood. The term "prodrug," refers to compounds that contain, but are not limited to, substituents known as "therapeutically suitable esters." The term "therapeutically suitable ester," refers to alkoxycarbonyl groups appended to the parent molecule on an available carbon atom. More specifically, a "therapeutically suitable ester," refers to alkoxycarbonyl groups appended to the parent molecule on one or more available aryl, cycloalkyl and/or heterocycle groups. Compounds containing therapeutically suitable esters are an example, but are not intended to limit the scope of compounds considered to be prodrugs. Examples of prodrug ester groups include pivaloyloxymethyl, acetoxymethyl, phthalidyl, indanyl and methoxymethyl, as well as other such groups known in the art. Other examples of prodrug ester groups are found in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The terms "pharmaceutically effective amount" and "effective amount", as used herein, refer to an amount of a pharmaceutical formulation that will elicit the desired therapeutic effect or response when administered in accordance with the desired treatment regimen. US2011/0144086 describes the use of some diabenzothiazepine molecules (DBTs) as anti-malarial "inhibitors of the plasmodial surface anion channel." However, no study of DBT molecules as anti-virals has yet been reported.

In an embodiment, provided herein are compounds represented by Formula I:

Formula I wherein

Y is selected from the group consisting of $S(O)_y$, C=O, $C(R^{11})_2$, $NR_Y$ and O wherein y is 0, 1, or 2; $R^{11}$ is H or $C_{1-6}$alkyl, $R_Y$ is selected from the group consisting of H, methyl, ethyl, propyl, proprenyl, phenyl and benzyl, wherein $R_Y$ when not H may be optionally substituted by hydroxyl;

$R^Z$ is selected from the group consisting of H, methyl, ethyl, propyl, phenyl and benzyl;

$R^{m'}$ and $R^m$ are each independently selected from the group consisting of H and $C_{1-6}$alkyl (optionally substituted by one, two or three substituents each independently selected from halogen and hydroxyl);

L is bond or $C_{1-2}$alkylene (optionally substituted by halogen or $C_{1-2}$alkyl);

A is a 5-7 membered monocyclic heterocyclic or 5-6 membered monocyclic heteroaryl ring optionally substituted by one or two substituents selected from the group consisting of halogen, hydroxyl, cyano, $C_{1-6}$alkyl, $C_{2-6}$alkenyl, $C_{2-6}$alkynyl, $C_{1-6}$alkoxy, and NR'R";

B is selected from the group consisting of phenyl (optionally substituted by one, two or three substituents represented by $R^{33}$), 5-6 membered monocyclic heteroaryl optionally substituted by one, two or three substituents represented by $R^{33}$), and 9-10 membered bicyclic heteroaryl (optionally substituted by one, two or three substituents represented by $R^{33}$);

R' is selected, independently for each occurrence, from H, methyl, ethyl, and propyl;

R" is selected, independently for each occurrence, from H, methyl, ethyl, propyl, butyl, —C(O)-methyl and —C(O)-ethyl, or R' and R" taken together with the nitrogen to which they are attached may form a 4-6 membered heterocycle;

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R";

$R^{33}$ is independently selected for each occurrence from the group consisting of H, halogen, hydroxyl, nitro, cyano, $C_{1-6}$alkyl, —C(O)—O—$C_{1-6}$alkyl, —C(O)—NR'R", —C(=NH)—NR'R", $C_{2-6}$alkenyl, $C_{2-6}$alkynyl, $C_{1-6}$alkoxy, carboxy, —CHO, NR'R", —C(O)—$C_{1-6}$alkyl, —C(O)—$C_{1-6}$ alkoxy, $C_{3-6}$cycloalkyl, —S(O)$_w$—$C_{1-6}$alkyl (where w is 0, 1 or 2), —S(O)$_w$—NR'R" (where w is 0, 1 or 2), and —NR'—S(O)$_w$—$C_{1-6}$alkyl (where w is 0, 1 or 2);

q is 0, 1, 2 or 3;

wherein for each occurrence, $C_{1-6}$alkyl may be optionally substituted with one, two, three or more substituents selected from the group consisting of halogen, hydroxyl, nitro, cyano, carboxy, $C_{2-6}$alkenyl, $C_{2-6}$alkynyl, $C_{1-6}$alkoxy, NR'R", —NR'—S(O)$_w$—$C_{1-6}$alkyl (where w is 0, 1 or 2), and S(O)$_w$—NR'R" (where w is 0, 1 or 2); $C_{1-6}$alkoxy may be optionally substituted with one, two, three or more substituents selected from the group consisting of halogen, hydroxyl, nitro, cyano, carboxy, $C_{1-6}$alkyl, NR'R", —NR'—S(O)$_w$—$C_{1-6}$alkyl (where w is 0, 1 or 2), and S(O)$_w$—NR'R" (where w is 0, 1 or 2); and pharmaceutically acceptable salts thereof.

An exemplary compound may be represented by Formula II:

Formula II where for example the substituents are described above.

For example, a compound of one of the above Formulas I and II may have A is a 5-6 membered monocyclic heteroaryl. In some embodiments A is pyridinyl; in other embodiments A is pyrimidinyl; in still other embodiments A is thiadiazole. In some embodiments A is optionally substituted by one substituent selected from the group consisting of halogen, $C_{1-6}$haloalkyl, and $C_{1-6}$alkyl. In some embodiments, A is unsubstituted.

For example, a compound of one of the above formulas may have each of moieties $R^4$, $R^5$, $R^6$, $R^7$, $R^8$, $R^9$, and $R^{10}$ independently selected for each occurrence from the group consisting of hydrogen, methyl, trifluoromethyl, and halogen. In some embodiments, each of moieties $R^4$, $R^5$, $R^6$, $R^7$, $R^8$, $R^9$, and $R^{10}$ is hydrogen.

For example, in some embodiments $R^Z$ is hydrogen. In some embodiments $R^{m'}$ and $R^m$ are each hydrogen. In some embodiments L is a bond or a methylene. In some embodiments L is a bond. In some embodiments Y is $SO_2$.

For example, in some embodiments $R^{33}$ is selected from the group consisting of H, halogen, hydroxyl, cyano, $C_{1-6}$alkyl, —C(O)—O—$C_{1-6}$alkyl, —C(O)—NR'R", $C_{1-6}$alkoxy, carboxy, CHO, NR'R", and —$C_{1-6}$alkyl-OH.

For example, in some embodiments A is optionally substituted by one substituent selected from the group consisting of halogen, $C_{1-6}$haloalkyl, and $C_{1-6}$alkyl.

For example, in some embodiments B is selected from the group consisting of phenyl, indolyl, indazolyl, benzimidazolyl, and pyrimidinyl, each of which may be optionally substituted by one, two or three substituents represented by $R^{33}$.

For example, the present disclosure also provides, in part, a compound selected from the group consisting a compound of Table 3 and pharmaceutically acceptable salts thereof. In an embodiment, the present disclosure provides a pharmaceutically acceptable composition comprising a disclosed compound of any one of Formulas I to II, and a pharmaceutically acceptable excipient.

An exemplary compound may be represented by Formula III:

Formula III

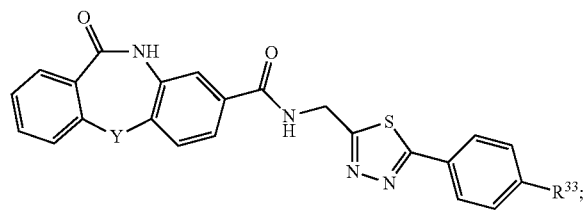

and pharmaceutically acceptable salts thereof; wherein

Y is selected from the group consisting of $S(O)_y$, C=O, $C(R^{11})_2$, $NR_Y$ and O wherein y is 0, 1, or 2; $R^{11}$ is H or $C_{1-6}$alkyl, $R_Y$ is selected from the group consisting of H, methyl, ethyl, propyl, phenyl and benzyl; and $R^{33}$ is selected from the group consisting of H, halogen, hydroxyl, nitro, cyano, $C_{1-6}$alkyl, —C(O)—O—$C_{1-6}$alkyl, —C(O)—NR'R", —C(=NH)—NR'R", $C_{2-6}$alkenyl, $C_{2-6}$alkynyl, $C_{1-6}$alkoxy, carboxy, —CHO, NR'R", —C(O)—$C_{1-6}$alkyl, —C(O)—$C_{1-6}$alkoxy, $C_{3-6}$cycloalkyl, —S(O)$_w$—$C_{1-6}$alkyl (where w is 0, 1, or 2), —S(O)$_w$—NR'R" (where w is 0, 1, or 2), and —NR'—S(O)$_w$—$C_{1-6}$alkyl (where w is 0, 1 or 2).

For example, in some embodiments of Formula III, Y is S, $S(O)_2$ or S(O).

An exemplary Compound may be represented by one of Formulas IV to VII: compound represented by:

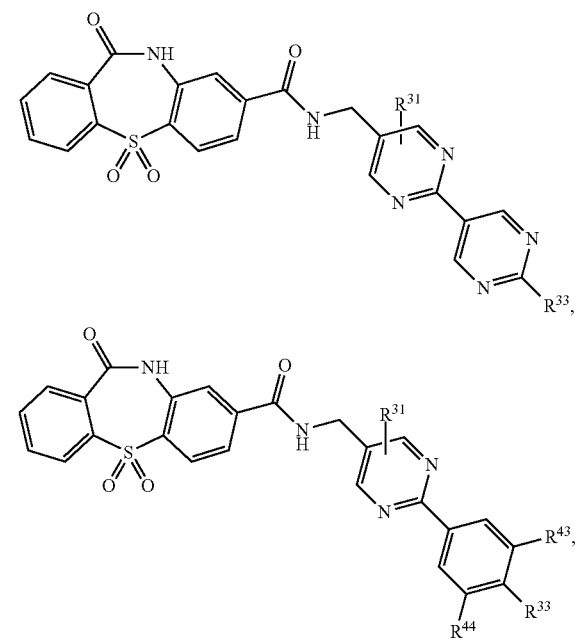

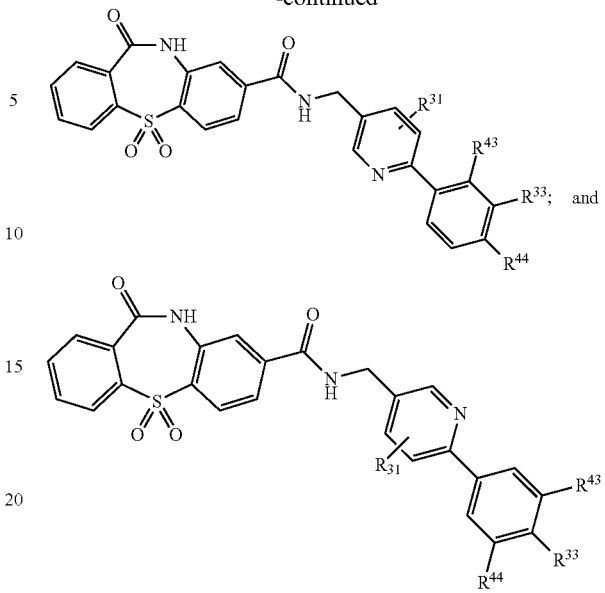

and pharmaceutically acceptable salts and N-oxides thereof, wherein $R^{33}$ is selected from the group consisting of H, halogen, hydroxyl, nitro, cyano, $C_{1-6}$ alkyl, —C(O)—O—$C_{1-6}$alkyl, —C(O)—NR'R", —C(=NH)—NR'R", $C_{2-6}$alkenyl, $C_{2-6}$alkynyl, $C_{1-6}$alkoxy, carboxy, —CHO, NR'R", —C(O)—$C_{1-6}$alkoxy, $C_{3-6}$cycloalkyl, —S(O)$_w$—$C_{1-6}$alkyl (where w is 0, 1 or 2), —S(O)$_w$—NR'R" (where w is 0, 1 or 2), and —NR'—S(O)$_w$—$C_{1-6}$alkyl (where w is 0, 1 or 2);

$R^{43}$ is selected from the group consisting of H, halogen, hydroxyl, nitro, cyano, $C_{1-6}$alkyl, —C(O)—O—$C_{1-6}$alkyl, —C(O)—NR'R", —C(=NH)—NR'R", $C_{2-6}$alkenyl, $C_{2-6}$alkynyl, $C_{1-6}$alkoxy, carboxy, —CHO, NR'R", —C(O)—$C_{1-6}$alkoxy, $C_{3-6}$cycloalkyl, —S(O)$_w$—$C_{1-6}$alkyl (where w is 0, 1 or 2), —S(O)$_w$—NR'R" (where w is 0, 1 or 2), and —NR'—S(O)$_w$—$C_{1-6}$alkyl (where w is 0, 1 or 2);

$R^{31}$ is optional, and may be selected from the group consisting of halogen, hydroxyl, nitro, cyano, $C_{1-6}$alkyl, —C(O)—O—$C_{1-6}$alkyl, —C(O)—NR'R", —C(=NH)—NR'R", $C_{2-6}$alkenyl, $C_{2-6}$alkynyl, $C_{1-6}$alkoxy, carboxy, —CHO, NR'R", —C(O)—O—$C_{1-6}$alkyl, —C(O)—$C_{1-6}$alkoxy, $C_{3-6}$cycloalkyl, —S(O)$_w$—$C_{1-6}$alkyl (where w is 0, 1 or 2), —S(O)$_w$—NR'R" (where w is 0, 1 or 2), and —NR'—S(O)$_w$—$C_{1-6}$alkyl (where w is 0, 1 or 2);

$R^{44}$ is selected from the group consisting of H, halogen, hydroxyl, nitro, cyano, $C_{1-6}$ alkyl, —C(O)—O—$C_{1-6}$alkyl, —C(O)—NR'R", —C(=NH)—NR'R", $C_{2-6}$alkenyl, $C_{2-6}$alkynyl, $C_{1-6}$alkoxy, carboxy, —CHO, NR'R", —C(O)—$C_{1-6}$alkoxy, $C_{3-6}$cycloalkyl, —S(O)$_w$—$C_{1-6}$alkyl (where w is 0, 1 or 2), —S(O)$_w$—NR'R" (where w is 0, 1 or 2), and —NR'—S(O)$_w$—$C_{1-6}$alkyl (where w is 0, 1 or 2);

wherein for each occurrence, $C_{1-6}$alkyl may be optionally substituted with one, two, three or more substituents selected from the group consisting of halogen, hydroxyl, nitro, cyano, carboxy, $C_{2-6}$alkenyl, $C_{2-6}$alkynyl, $C_{1-6}$alkoxy, NR'R", —NR'—S(O)$_w$—$C_{1-6}$alkyl (where w is 0, 1 or 2), and S(O)$_w$—NR'R" (where w is 0, 1 or 2); $C_{1-6}$alkoxy may be optionally substituted with one, two, three or more substituents selected from the group consisting of halogen, hydroxyl, nitro, cyano, carboxy, $C_{1-6}$alkyl, NR'R", —NR'—S(O)$_w$—$C_{1-6}$alkyl (where w is 0, 1 or 2), and S(O)$_w$—NR'R" (where w is 0, 1 or 2);

R' is selected, independently for each occurrence, from H, methyl, ethyl, and propyl;

R" is selected, independently for each occurrence, from H, methyl, ethyl, propyl, butyl, —C(O)-methyl and —C(O)-ethyl, or R' and R" taken together with the nitrogen to which they are attached may form a 4-7 membered heterocycle;

wherein for each occurrence, $C_{1-6}$alkyl may be optionally substituted with one, two, three or more substituents selected from the group consisting of halogen, hydroxyl, nitro, cyano, carboxy, $C_{2-6}$alkenyl, $C_{2-6}$alkynyl, $C_{1-6}$alkoxy, NR'R", —NR'—S(O)$_w$—$C_{1-6}$alkyl (where w is 0, 1 or 2), and S(O)$_w$—NR'R" (where w is 0, 1 or 2); $C_{1-6}$alkoxy may be optionally substituted with one, two, three or more substituents selected from the group consisting of halogen, hydroxyl, nitro, cyano, carboxy, $C_{1-6}$alkyl, NR'R", —NR'—S(O)$_w$—$C_{1-6}$alkyl (where w is 0, 1 or 2), and S(O)$_w$—NR'R" (where w is 0, 1 or 2).

In a further aspect, a method for treating a hepatitis B infection in a patient in need thereof is provided, comprising administering to a subject or patient an effective amount of a disclosed compound, and/or administering a first disclosed compound and optionally, and additional, different disclosed compound(s). In another embodiment, a method for treating a hepatitis B infection in a patient in need thereof is provided, comprising administering to a subject or patient a therapeutically effective amount of a pharmaceutical composition comprising a disclosed compound, or two or more disclosed compounds.

For use in accordance with this aspect, the appropriate dosage is expected to vary depending on, for example, the particular compound employed, the mode of administration, and the nature and severity of the infection to be treated as well as the specific infection to be treated and is within the purview of the treating physician. Usually, an indicated administration dose may be in the range between about 0.1 to about 1000 μg/kg body weight. In some cases, the administration dose of the compound may be less than 400 μg/kg body weight. In other cases, the administration dose may be less than 200 μg/kg body weight. In yet other cases, the administration dose may be in the range between about 0.1 to about 100 μg/kg body weight. The dose may be conveniently administered once daily, or in divided doses up to, for example, four times a day or in sustained release form.

A compound may be administered by any conventional route, in particular: enterally, topically, orally, nasally, e.g. in the form of tablets or capsules, via suppositories, or parenterally, e.g. in the form of injectable solutions or suspensions, for intravenous, intra-muscular, sub-cutaneous, or intra-peritoneal injection. Suitable formulations and pharmaceutical compositions will include those formulated in a conventional manner using one or more physiologically acceptable carriers or excipients, and any of those known and commercially available and currently employed in the clinical setting. Thus, the compounds may be formulated for oral, buccal, topical, parenteral, rectal or transdermal administration or in a form suitable for administration by inhalation or insufflation (either orally or nasally).

For oral administration, pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). Preparations may also contain buffer salts, flavoring, coloring and sweetening agents as appropriate.

Preparations for oral administration may also be suitably formulated to give controlled-release or sustained release of the active compound(s) over an extended period. For buccal administration the compositions may take the form of tablets or lozenges formulated in a conventional manner known to the skilled artisan.

A disclosed compound may also be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain additives such as suspending, stabilizing and/or dispersing agents. Alternatively, the compound may be in powder form for constitution with a suitable vehicle, e.g. sterile pyrogen-free water, before use. Compounds may also be formulated for rectal administration as suppositories or retention enemas, e.g. containing conventional suppository bases such as cocoa butter or other glycerides.

In some cases, a disclosed compound may be administered as part of a combination therapy in conjunction with one or more antivirals. Example antivirals include nucleoside analogs, interferon α, and other assembly effectors, for instance heteroaryldihydropyrimidines (HAPs) such as methyl 4-(2-chloro-4-fluorophenyl)-6-methyl-2-(pyridin-2-yl)-1,4-dihydropyrimidine-5-carboxylate (HAP-1). For example, provided herein is a method of treating patient suffering from hepatitis B comprising administering to a subject a first amount of a disclosed compound and a second amount of an antiviral, or other anti HBV agent, for example a second amount of a second compound selected from the group consisting of: another HBV caspid assembly promoter (such as certain compounds disclosed herein or for example, GLS4, BAY 41-4109, AT-130, DVR-23 (e.g., as depicted below),

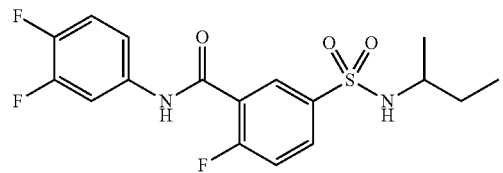

DVR-23

NVR 3-778, NVR1221 (by code); and N890 (as depicted below):

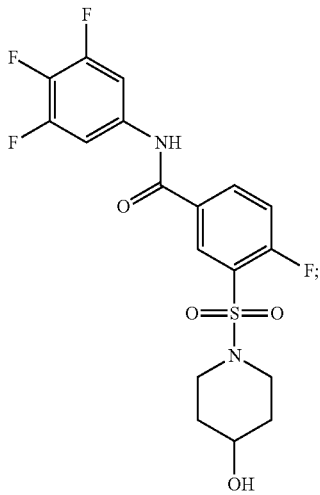 [SMILES: O=C(Nc1cc(F)c(F)c(F)c1)c1ccc(F)c(S(=O)(=O)N2CCC(O)CC2)c1]

other CpAMs such as those disclosed in the following patent applications hereby incorporated by reference: WO2014037480, WO2014184328, WO2013006394, WO2014089296, WO2014106019, WO2013102655, WO2014184350, WO2014184365, WO2014161888, WO2014131847, WO2014033176, WO2014033167, and WO2014033170; Nucleoside analogs interfering with viral polymerase, such as entecavir (Baraclude), Lamivudine, (Epivir-HBV), Telbivudine (Tyzeka, Sebivo), Adefovir dipivoxil (Hepsera), Tenofovir (Viread), Tenofovir alafenamide fumarate (TAF), prodrugs of tenofavir (e.g. AGX-1009), L-FMAU (Clevudine), LB80380 (Besifovir) and:

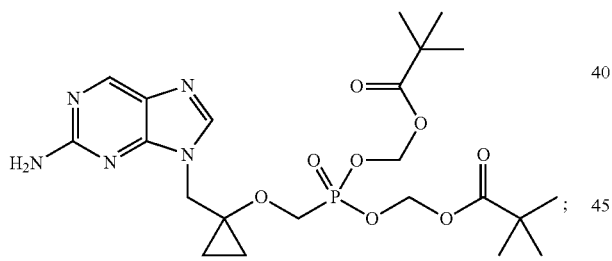

viral entry inhibitors such as Myrcludex B and related lipopeptide derivatives; HBsAg secretion inhibitors such as REP 9AC' and related nucleic acid-based amphipathic polymers, HBF-0529 (PBHBV-001), PBHBV-2-15 as depicted below:

22: HBF-0529

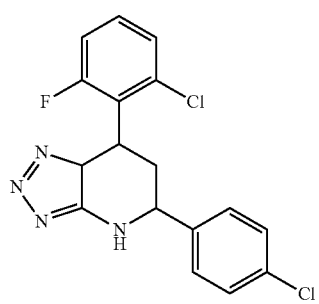

23: PBHBV-2-15

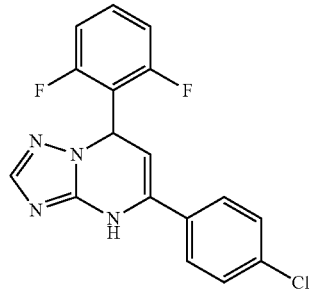

and BM601 as depicted below:

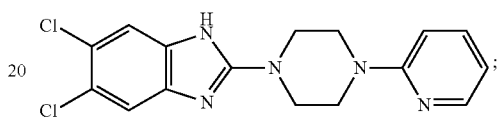

disruptors of nucleocapsid formation or integrity such as NZ-4/W28F:

NZ-4

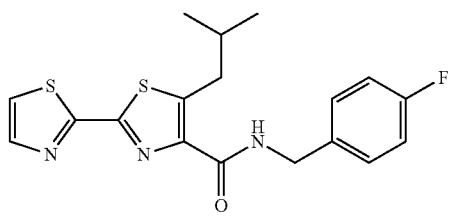

cccDNA formation inhibitors: such as BSBI-25, CCC-0346, CCC-0975 (as depicted below):

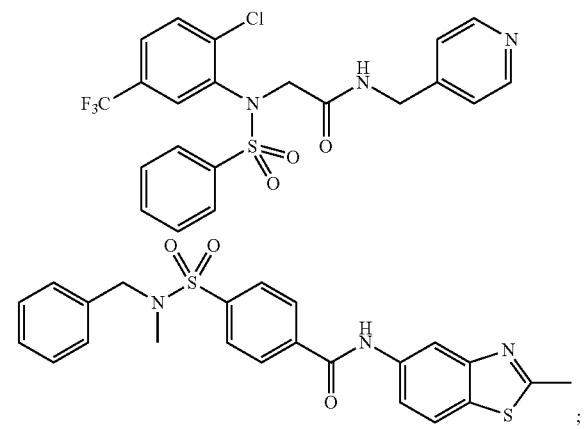

HBc directed transbodies such as those described in Wang Y, et al, Transbody against hepatitis B virus core protein inhibits hepatitis B virus replication in vitro, Int. Immunopharmacol (2014), located at //dx.doi.org/10.1016/j.intimp.2015.01.028; antiviral core protein mutant (such as Cp183-V124W and related mutations as described in WO/2013/010069, WO2014/074906 each incorporated by reference); inhibitors of HBx-interactions such as RNAi, antisense and nucleic acid based polymers targeting HBV RNA; e.g., RNAi (for example ALN-HBV, ARC-520, TKM-HBV, ddRNAi), antisense (ISIS-HBV), or nucleic acid based polymer: (REP 2139-Ca); immunostimulants such as Interferon alpha 2a (Roferon), Intron A (interferon alpha 2b), Pegasys (peginterferon alpha 2a), Pegylated IFN 2b, IFN lambda 1a and PEG IFN lambda 1a, Wellferon, Roferon, Infergen, lymphotoxin beta agonists such as CBE11 and BS1); Non-Interferon Immune enhancers such as Thymosin alpha-1 (Zadaxin) and Interleukin-7 (CYT107); TLR-7/9 agonists such as GS-9620, CYT003, Resiquimod; Cyclophilin Inhibitors such as NVP018; OCB-030; SCY-635; Alisporivir; NIM811 and related cyclosporine analogs; vaccines such as GS-4774, TG1050, Core antigen vaccine; SMAC mimetics such as birinapant and other IAP-antagonists; Epigenetic modulators such as KMT inhibitors (EZH1/2, G9a, SETD7, Suv39 inhibitors), PRMT inhibitors, HDAC inhibitors, SIRT agonists, HAT inhibitors, WD antagonists (e.g. OICR-9429), PARP inhibitors, APE inhibitors, DNMT inhibitors, LSD1 inhibitors, JMJD HDM inhibitors, and Bromodomain antagonists; kinase inhibitors such as TKB1 antagonists, PLK1 inhibitors, SRPK inhibitors, CDK2 inhibitors, ATM & ATR kinase inhibitors; STING Agonists; Ribavirin; N-acetyl cysteine; NOV-205 (BAM205); Nitazoxanide (Alinia), Tizoxanide; SB 9200 Small Molecule Nucleic Acid Hybrid (SMNH); DV-601; Arbidol; FXR agonists (such as GW 4064 and Fexaramin); antibodies, therapeutic proteins, gene therapy, and biologics directed against viral components or interacting host proteins.

In some embodiments, the disclosure provides a method of treating a hepatitis B infection in a patient in need thereof, comprising administering a first compound selected from any one of the disclosed compounds, and one or more other HBV agents each selected from the group consisting of HBV capsid assembly promoters, HBF viral polymerase interfering nucleosides, viral entry inhibitors, HBsAg secretion inhibitors, disruptors of nucleocapsid formation, cccDNA formation inhibitors, antiviral core protein mutant, HBc directed transbodies, RNAi targeting HBV RNA, immunostimulants, TLR-7/9 agonists, cyclophilin inhibitors, HBV vaccines, SMAC mimetics, epigenetic modulators, kinase inhibitors, and STING agonists. In some embodiments, the disclosure provides a method of treating a hepatitis B infection in a patient in need thereof, comprising administering an amount of a disclosed, and administering another HBV capsid assembly promoter.

In some embodiments, the first and second amounts together comprise a pharmaceutically effective amount. The first amount, the second amount, or both may be the same, more, or less than effective amounts of each compound administered as monotherapies. Therapeutically effective amounts of a disclosed compound and antiviral may be co-administered to the subject, i.e., administered to the subject simultaneously or separately, in any given order and by the same or different routes of administration. In some instances, it may be advantageous to initiate administration of a disclosed compound first, for example one or more days or weeks prior to initiation of administration of the antiviral. Moreover, additional drugs may be given in conjunction with the above combination therapy.

In another embodiment, a disclosed compound may be conjugated (e.g., covalently bound directly or through molecular linker to a free carbon, nitrogen (e.g. an amino group), or oxygen (e.g. an active ester) of a disclosed compound), with a detection moiety, e.g. a fluorophore moiety (such a moiety may for example re-emit a certain light frequency upon binding to a virus and/or upon photon excitation. Contemplated fluorophores include AlexaFluor® 488 (Invitrogen) and BODIPY FL (Invitrogen), as well as fluorescein, rhodamine, cyanine, indocarbocyanine, anthraquinones, fluorescent proteins, aminocoumarin, methoxycoumarin, hydroxycoumarin, Cy2, Cy3, and the like. Such disclosed compounds conjugated to a detection moiety may be used in e.g. a method for detecting HBV or biological pathways of HBV infection, e.g., in vitro or in vivo; and/or methods of assessing new compounds for biological activity.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. At least some of the compounds identified as "intermediates" herein are contemplated as compounds of the invention.

Example 1: Synthesis of 7-methyl-11-oxo-10,11-dihydrodibenzo[b,f][1,4]thiazepine-8-carboxylic Acid (7): A Common Intermediate

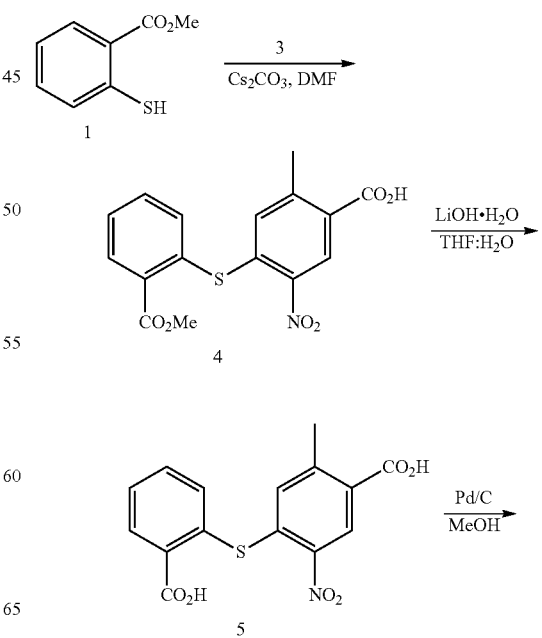

-continued

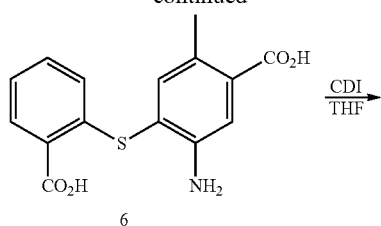
6

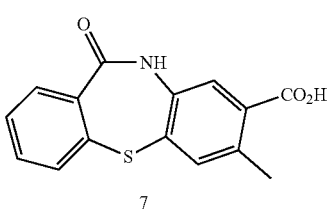
7

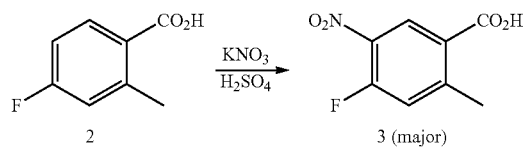

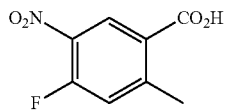
3A

Synthesis of 4-fluoro-2-methyl-5-nitrobenzoic Acid (3)

3

To a stirred solution of 4-fluoro-2-methylbenzoic acid 2 (500 mg, 3.24 mmol) in concentrated sulfuric acid (2.5 mL) under inert atmosphere was added potassium nitrate (655 mg, 6.49 mmol) at 0° C.; warmed to RT and stirred for 6 h. The reaction was monitored by TLC; after completion of the reaction, the reaction mixture was quenched with ice water (20 mL), filtered the precipitated solid and dried in vacuo to obtain the crude. The crude was purified through silica gel column chromatography using 5% MeOH/CH$_2$Cl$_2$ to afford compound 3 (300 mg, 60%) as brown syrup. TLC: 10% MeOH/CH$_2$Cl$_2$ (R$_f$: 0.3); $^1$H-NMR (DMSO-d$_6$, 500 MHz): δ 13.56 (br s, 1H), 8.52 (d, J=8.0 Hz, 1H), 7.61 (d, J=12.5 Hz, 1H), in 2.63 (s, 3H).

Synthesis of 4-((2-(methoxycarbonyl) phenyl) thio)-2-methyl-5-nitrobenzoic Acid (4)

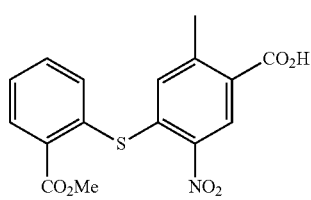
4

To a stirred solution of methyl 2-mercaptobenzoate 1 (514 mg, 3.08 mmol) in DMF (10 mL) under inert atmosphere were added cesium carbonate (1.81 g, 5.57 mmol), compound 3 (560 mg, 2.78 mmol) at RT; heated to 60° C. and stirred for 4 h. The reaction was monitored by TLC; after completion of the reaction, the volatiles were removed under reduced pressure. The residue was diluted with water (20 mL) and pH was adjusted to ~2 with 1 N HCl, filtered the precipitated solid and dried in vacuo to afford compound 4 (500 mg, 52%) as an off-white solid. TLC: 5% MeOH/CH$_2$Cl$_2$ (R$_f$: 0.4); $^1$H-NMR (DMSO-d$_6$, 400 MHz): δ 13.47 (br s, 1H), 8.59 (s, 1H), 7.94 (d, J=7.2 Hz, 1H), 7.68-7.60 (m, 3H), 6.83 (s, 1H), 3.72 (s, 3H), 2.40 (s, 3H).

Synthesis of methyl 3-amino-4-((2-(methoxycarbonyl) phenyl) thio)-5-methylbenzoate (5)

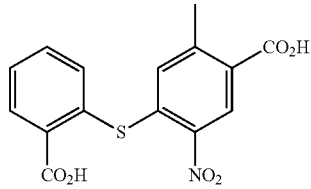
5

To a stirred solution of compound 4 (500 mg, 1.45 mmol) in THF:H$_2$O (2:1, 15 mL) was added lithium hydroxide monohydrate (300 mg, 7.31 mmol) at RT and stirred for 8 h. The reaction was monitored by TLC; after completion of the reaction, the volatiles were removed in vacuo. The residue was diluted with water (15 mL), and pH was adjusted to ~2 with 1 N HCl, filtered the precipitated solid and dried in vacuo to afford crude compound 5 (500 mg) as an off-white solid. TLC: 5% MeOH/CH$_2$Cl$_2$ (R$_f$: 0.1); $^1$H-NMR (DMSO-d$_6$, 400 MHz): δ 13.51 (br s, 2H), 8.57 (s, 1H), 7.92 (d, J=7.2 Hz, 1H), 7.64-7.58 (m, 2H), 7.53 (t, J=8.0 Hz, 1H), 6.89 (s, 1H), 2.41 (s, 3H).

Synthesis of 5-amino-4-((2-carboxyphenyl)thio)-2-methylbenzoic Acid (6)

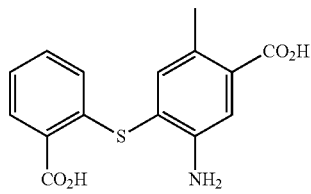
6

To a stirred solution of compound 5 (500 mg) in MeOH (15 mL) under inert atmosphere was added Pd/C (250 mg) at RT and stirred under hydrogen atmosphere for 16 h. The reaction was monitored by TLC; after completion of the reaction, the volatiles were removed in vacuo to afford crude compound 6 (430 mg) as an off-white solid. TLC: MeOH/CH$_2$Cl$_2$ (R$_f$: 0.1); LC-MS: 84.24%; 304.5 (M$^+$+1); (column; X-Select CSH C-18, (50×3.0 mm, 3.5 µm); RT 3.75 min. 0.05% TFA (Aq): ACN; 0.8 mL/min).

Synthesis of 7-methyl-11-oxo-10,11-dihydrodibenzo[b,f][1,4]thiazepine-8-carboxylic Acid (7)

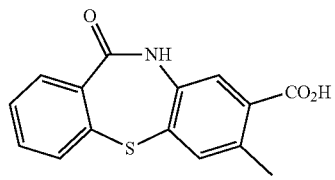

To a stirred solution of compound 6 (430 mg) in THF (20 mL) under inert atmosphere was added CDI (1.15 g, 7.09 mmol) at RT and stirred for 18 h. The reaction was monitored by TLC; after completion of the reaction, the volatiles were removed in vacuo and neutralized with 1 N HCl, filtered the precipitated solid and dried in vacuo to afford the crude compound 7 (290 mg) as an off-white solid. TLC: 10% MeOH/CH$_2$Cl$_2$ (R$_f$: 0.5); $^1$H-NMR (DMSO-d$_6$, 500 MHz): δ 13.15 (br s, 1H), 10.68 (s, 1H), 7.69-7.68 (m, 2H), 7.67-7.44 (m, 4H), 2.44 (s, 3H).

Example 2: Synthesis of 2-chloro-11-oxo-10,11-dihydrodibenzo[b,f][1,4]thiazepine-8-carboxylic Acid (16): A Common Intermediate

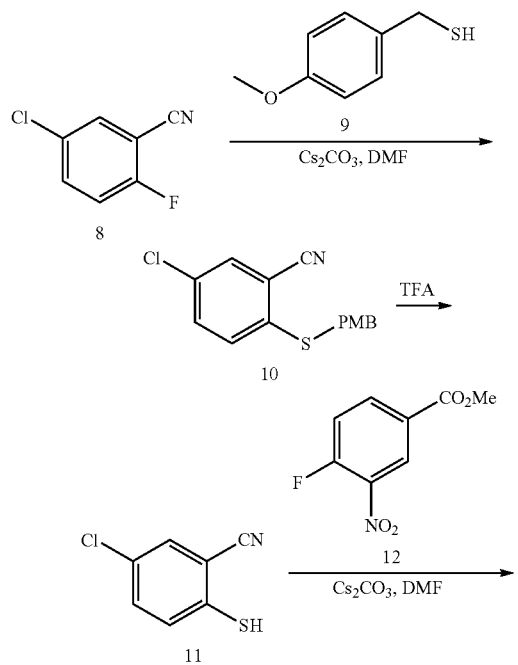

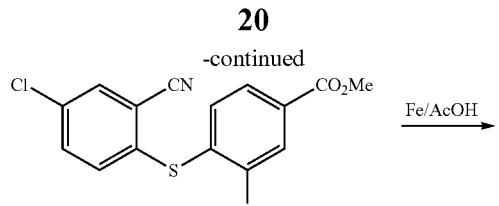

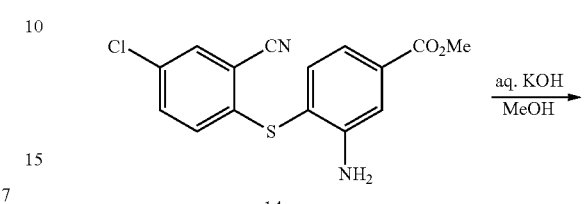

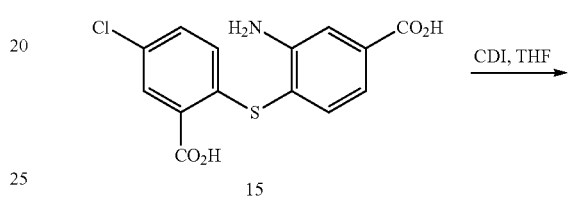

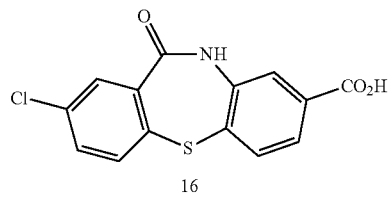

Synthesis of 5-chloro-2-((4-methoxybenzyl) thio) benzonitrile (10)

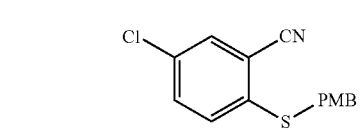

To a stirred solution of 5-chloro-2-fluorobenzonitrile 8 (1.0 g, 6.41 mmol) in DMF (10 mL) under inert atmosphere was added cesium carbonate (2.30 g, 7.05 mmol) at RT; heated to 40° C. and to this was added (4-methoxyphenyl) methanethiol 9 (1.08 g, 7.05 mmol); heated to 60° C. and stirred for 2 h. The reaction was monitored by TLC; after completion of the reaction, the reaction mixture was diluted with water (20 mL) and extracted with EtOAc (2×25 mL). The combined organic extracts were dried over sodium sulfate, filtered and concentrated in vacuo to obtain the crude. The crude was purified through silica gel column chromatography using 3-5% EtOAc/hexanes to afford compound 10 (1 g, 54%) as white solid. TLC: 10% EtOAc/hexanes (R$_f$: 0.6); $^1$H-NMR (CDCl$_3$, 500 MHz): δ 7.57 (s, 1H), 7.39 (d, J=8.0 Hz, 1H), 7.28-7.27 (m, 1H), 7.20 (d, J=9.0 Hz, 2H), 6.81 (d, J=9.0 Hz, 2H), 4.15 (s, 2H), 3.78 (s, 3H).

Synthesis of 5-chloro-2-mercaptobenzonitrile (11)

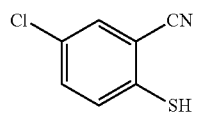

A stirred solution of compound 10 (1 g, 3.47 mmol) in trifluoro acetic acid (10 mL) under inert atmosphere was stirred at 70° C. for 5 h. The reaction was monitored by TLC; after completion of the reaction, the volatiles were removed in vacuo to obtain the crude compound 11 (590 mg) which was carried to the next step without further purification. TLC: 30% EtOAc/hexanes ($R_f$: 0.2); $^1$H-NMR (CDCl$_3$, 500 MHz): δ 7.57 (s, 1H), 7.41 (d, J=9.0 Hz, 1H), 7.34 (d, J=9.0 Hz, 1H), 4.08 (s, 1H).

Synthesis of methyl 4-((4-chloro-2-cyanophenyl) thio)-3-nitrobenzoate (13)

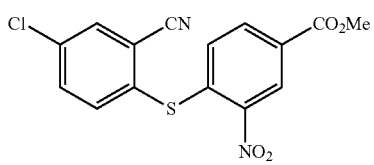

To a stirred solution of compound 11 (620 mg, 3.11 mmol) in DMF (10 mL) under inert atmosphere was added cesium carbonate (1.1 g, 3.42 mmol) at RT; heated to 40° C. and stirred for 10 min. To this was added methyl 4-fluoro-3-nitrobenzoate 12 (582 mg, 3.42 mmol) at 60° C. and stirred for 3 h. The reaction was monitored by TLC; after completion of the reaction, the reaction mixture was diluted with water (20 mL) and extracted with EtOAc (2×20 mL). The combined organic extracts were dried over sodium sulfate, filtered and concentrated in vacuo to obtain the crude. The crude was purified through silica gel column chromatography using 25% EtOAc/hexanes to afford compound 13 (600 mg, 55%) as pale yellow solid. TLC: 30% EtOAc/hexanes ($R_f$: 0.4); $^1$H-NMR (DMSO-d$_6$, 400 MHz): δ 8.66 (s, 1H), 8.33 (s, 1H), 8.05-8.03 (m, 1H), 7.98-7.92 (m, 2H), 7.02 (d, J=8.4 Hz, 1H), 3.86 (s, 3H).

Synthesis of methyl 3-amino-4-((4-chloro-2-cyanophenyl) thio) benzoate (14)

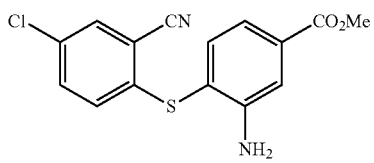

To a stirred solution of compound 13 (450 mg, 1.29 mmol) in acetic acid (15 mL) under inert atmosphere was added iron powder (724 mg, 12.9 mmol) at RT; heated to 90° C. and stirred for 3 h. The reaction was monitored by TLC; after completion of the reaction, the volatiles were removed in vacuo. The residue was basified with saturated NaHCO$_3$ solution (15 mL) and extracted with CH$_2$Cl$_2$ (2×20 mL). The combined organic extracts were dried over sodium sulfate, filtered and concentrated in vacuo to obtain the crude. The crude was triturated with 3% EtOAc/hexanes (2×5 mL) to afford compound 14 (290 mg, 70%) as pale yellow solid. TLC: 20% MeOH/CH$_2$Cl$_2$ ($R_f$: 0.7); $^1$H-NMR (DMSO-d$_6$, 400 MHz): δ 8.05 (s, $^1$H), 7.63-7.60 (m, 1H), 7.48 (s, 1H), 7.43 (d, J=8.0 Hz, 1H), 7.14 (d, J=8.8 Hz, 1H), 6.75 (d, J=8.8 Hz, 1H), 5.88 (s, 2H), 3.84 (s, 3H).

Synthesis of 2-((2-amino-4-carboxyphenyl) thio)-5-chlorobenzoic Acid (15)

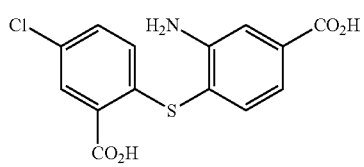

To a stirred solution of compound 14 (450 mg, 1.41 mmol) in MeOH (10 mL) was added potassium hydroxide (792 mg, 14.1 mmol) in water (3 mL) at 0° C.; heated to 90° C. and stirred for 9 h. The reaction was monitored by TLC; after completion of the reaction, the volatiles were removed in vacuo. The residue was acidified with 1 N HCl to pH~4.0. The obtained solid was filtered, washed with ether (2×5 mL) and dried in vacuo to afford compound 15 (350 mg, 76%) as an off-white solid. TLC: 20% MeOH/CH$_2$Cl$_2$ ($R_f$: 0.3); $^1$H-NMR (DMSO-d$_6$, 400 MHz): δ 12.92 (br s, 2H), 7.89 (s, 1H), 7.44-7.38 (m, 3H), 7.14 (d, J=8.8 Hz, 1H), 6.60 (d, J=8.8 Hz, 1H), 5.64 (br s, 2H).

Synthesis of 2-chloro-11-oxo-10,11-dihydrodibenzo [b,f][1,4]thiazepine-8-carboxylic Acid (16)

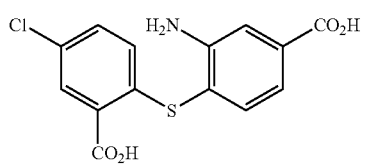

To a stirred solution of compound 15 (30 mg, 0.09 mmol) in THF (2 mL) under inert atmosphere was added CDI (45 mg, 0.27 mmol) at RT and stirred for 7 h. The reaction was monitored by TLC; after completion of the reaction, the volatiles were removed in vacuo. The residue was acidified with 2 N HCl to pH~4.0. The obtained solid was filtered, washed with ether (2×3 mL) and dried in vacuo to afford compound 16 (15 mg, 53%) as an off-white solid. TLC: 15% MeOH/CH$_2$Cl$_2$ ($R_f$: 0.5); $^1$H-NMR (DMSO-d$_6$, 400 MHz): δ 13.05 (br s, 1H), 10.98 (s, 1H), 7.80 (s, 1H), 7.72-7.70 (m, 3H), 7.64 (s, 2H).

Example 3: Synthesis of 3-chloro-11-oxo-10,11-dihydrodibenzo[b,f][1,4]thiazepine-8-carboxylic Acid (23): A Common Intermediate

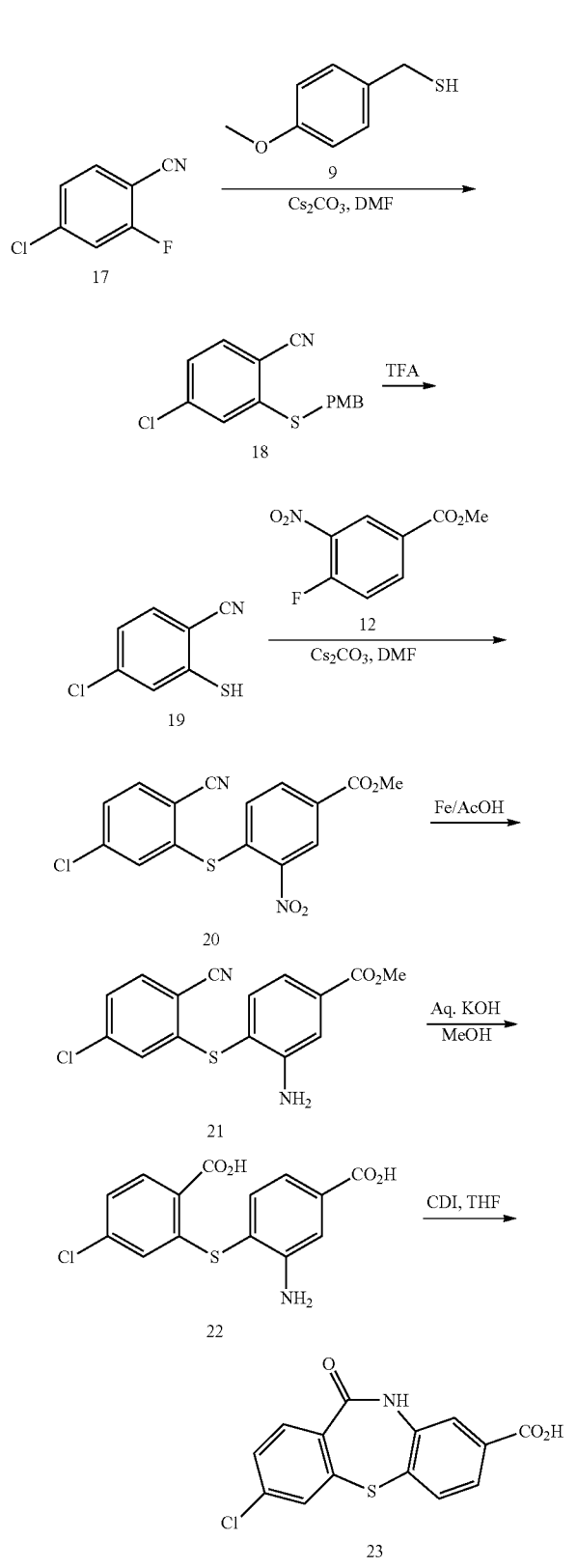

Synthesis of 4-chloro-2-((4-methoxybenzyl) thio) benzonitrile (18)

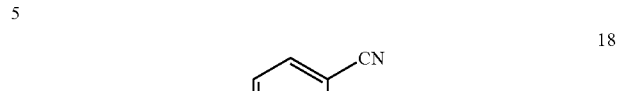

To a stirred solution of 4-chloro-2-fluorobenzonitrile 17 (1 g, 6.41 mmol) in DMF (25 mL) under inert atmosphere was added cesium carbonate (2.30 g, 7.05 mmol) at RT; heated to 40° C. and to this was added (4-methoxyphenyl) methanethiol 9 (1.08 g, 7.05 mmol); heated to 60° C. and stirred for 2 h. The reaction was monitored by TLC; after completion of the reaction, the reaction mixture was diluted with water (20 mL) and extracted with EtOAc (2×25 mL). The combined organic extracts were dried over sodium sulfate, filtered and concentrated in vacuo to obtain the crude. The crude was purified through silica gel column chromatography using 4% EtOAc/hexanes to afford compound 18 (900 mg, 48%) as white solid. TLC: 10% EtOAc/hexanes ($R_f$: 0.6); $^1$H-NMR (CDCl$_3$, 400 MHz): δ 7.51 (d, J=8.4 Hz, 1H), 7.33 (s, 1H), 7.23-7.20 (m, 3H), 6.84 (d, J=8.4 Hz, 2H), 4.19 (s, 2H), 3.79 (s, 3H).

Synthesis of 4-chloro-2-mercaptobenzonitrile (19)

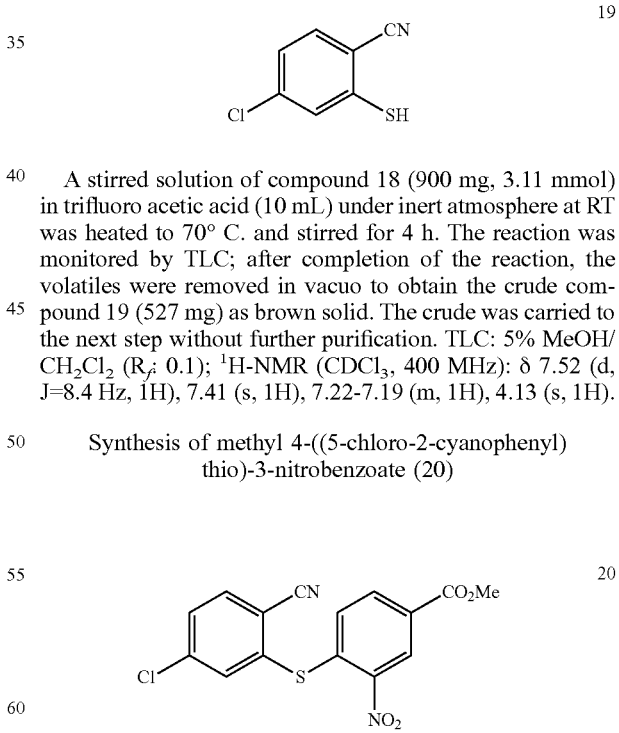

A stirred solution of compound 18 (900 mg, 3.11 mmol) in trifluoro acetic acid (10 mL) under inert atmosphere at RT was heated to 70° C. and stirred for 4 h. The reaction was monitored by TLC; after completion of the reaction, the volatiles were removed in vacuo to obtain the crude compound 19 (527 mg) as brown solid. The crude was carried to the next step without further purification. TLC: 5% MeOH/CH$_2$Cl$_2$ ($R_f$: 0.1); $^1$H-NMR (CDCl$_3$, 400 MHz): δ 7.52 (d, J=8.4 Hz, 1H), 7.41 (s, 1H), 7.22-7.19 (m, 1H), 4.13 (s, 1H).

Synthesis of methyl 4-((5-chloro-2-cyanophenyl) thio)-3-nitrobenzoate (20)

To a stirred solution of compound 19 (550 mg, 2.76 mmol) in DMF (15 mL) under inert atmosphere was added cesium carbonate (988 mg, 3.04 mmol) at RT; heated to 40° C. and stirred for 10 min. To this was added methyl 4-fluoro-3-nitrobenzoate 12 (515 mg, 3.04 mmol) at 60° C.

and stirred for 3 h. The reaction was monitored by TLC; after completion of the reaction, the reaction mixture was diluted with water (20 mL). The obtained solid was filtered, washed with 15% EtOAc/hexanes (2×5 mL) and dried in vacuo to afford compound 20 (700 mg, 73%) as yellow solid. TLC: 20% EtOAc/hexanes ($R_f$: 0.3); $^1$H-NMR (DMSO-$d_6$, 500 MHz): δ 8.69 (s, 1H), 8.18-8.15 (m, 2H), 8.10 (d, J=8.5 Hz, 1H), 7.92 (d, J=8.5 Hz, 1H), 7.10 (d, J=9.0 Hz, 1H), 3.90 (s, 3H).

Synthesis of methyl 3-amino-4-((5-chloro-2-cyanophenyl) thio) benzoate (21)

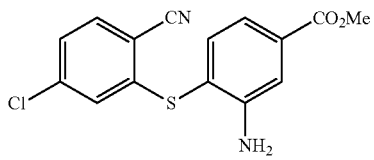

21

To a stirred solution of compound 20 (700 mg, 2.01 mmol) in acetic acid (15 mL) under inert atmosphere was added iron powder (1.12 g, 20.11 mmol) at RT; heated to 90° C. and stirred for 5 h. The reaction was monitored by TLC; after completion of the reaction, the volatiles were removed in vacuo. The residue was basified with 10% NaHCO$_3$ solution (20 mL) and extracted with CH$_2$Cl$_2$ (2×30 mL). The combined organic extracts were dried over sodium sulfate, filtered and concentrated in vacuo to obtain the crude. The crude was purified through silica gel column chromatography using 20% EtOAc/hexanes to afford compound 21 (500 mg, 78%) as yellow solid. TLC: 30% EtOAc/hexanes ($R_f$: 0.8); $^1$H-NMR (DMSO-$d_6$, 500 MHz): δ 7.92 (d, J=7.5 Hz, 1H), 7.51-7.43 (m, 3H), 7.17 (d, J=8.0 Hz, 1H), 6.66 (s, 1H), 5.96 (s, 2H), 3.86 (s, 3H).

Synthesis of 2-((2-amino-4-carboxyphenyl) thio)-4-chlorobenzoic Acid (22)

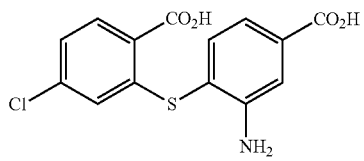

22

To a stirred solution of compound 21 (500 mg, 1.57 mmol) in MeOH (6 mL) was added potassium hydroxide (1.32 mg, 23.5 mmol) in water (6 mL) at 0° C.; heated to 90° C. and stirred for 24 h. The reaction was monitored by TLC; after completion of the reaction, the volatiles were removed in vacuo. The residue was diluted with water (20 mL) and extracted with EtOAc (2×25 mL). The aqueous layer was acidified with 1 N HCl to pH~6.0. The obtained solid was filtered, washed with ether (2×7 mL) and dried in vacuo to afford compound 22 (375 mg, 74%) as an off-white solid. TLC: 20% MeOH/CH$_2$Cl$_2$ ($R_f$: 0.2); $^1$H-NMR (CDCl$_3$, 400 MHz): δ 8.05 (d, J=8.4 Hz, 1H), 7.55-7.47 (m, 3H), 7.17-7.14 (m, 1H), 6.67 (s, 1H).

Synthesis of 3-chloro-11-oxo-10,11-dihydrodibenzo[b,f][1,4]thiazepine-8-carboxylic Acid (23)

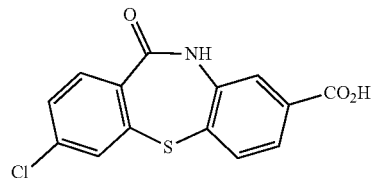

23

To a stirred solution of compound 22 (375 mg, 1.16 mmol) in THF (10 mL) under inert atmosphere was added CDI (564 mg, 3.48 mmol) at RT and stirred for 16 h. The reaction was monitored by TLC; after completion of the reaction, the volatiles were removed in vacuo. The residue was diluted with water (15 mL) and acidified with 6 N HCl to pH~1.0. The obtained solid was filtered, washed with ether (2×5 mL) and dried in vacuo to afford compound 23 (285 mg, 81%) as an off-white solid. TLC: 20% MeOH/CH$_2$Cl$_2$ ($R_f$: 0.4); $^1$H-NMR (DMSO-$d_6$, 400 MHz): δ 14.56 (br s, 2H), 10.90 (s, 1H), 9.11 (s, 1H), 7.71-7.65 (m, 4H).

Example 4: Synthesis of 11-oxo-10,11-dihydrodibenzo[b,f][1,4]thiazepine-8-carboxylic Acid (30): A Common Intermediate

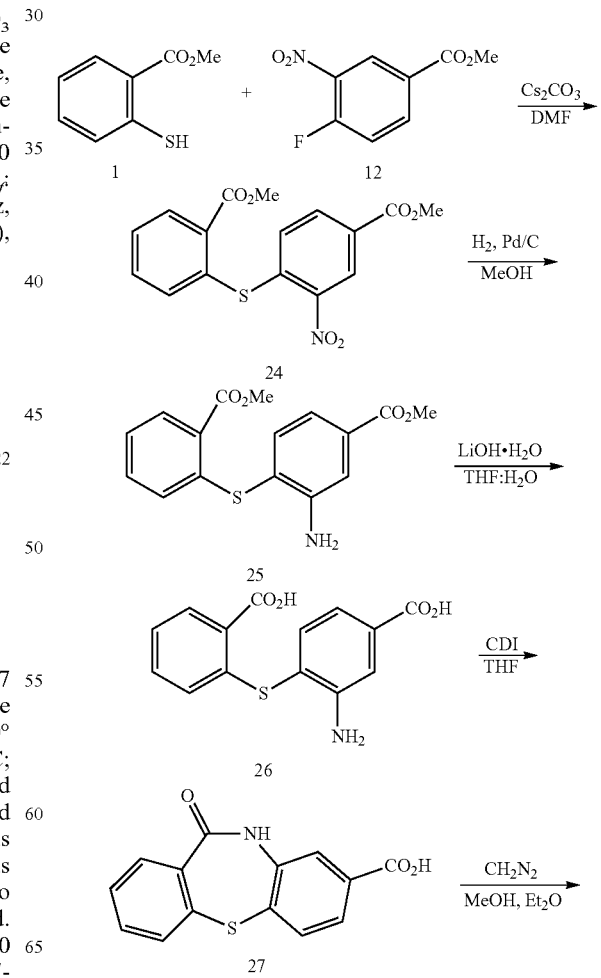

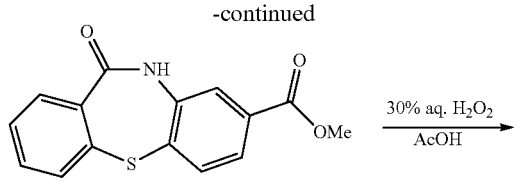

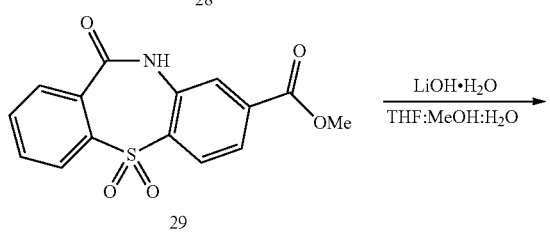

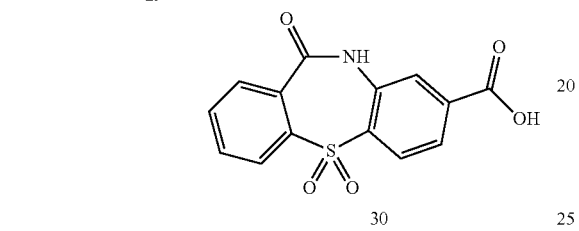

Synthesis of methyl 4-((2-(methoxycarbonyl) phenyl) thio)-3-nitrobenzoate (24)

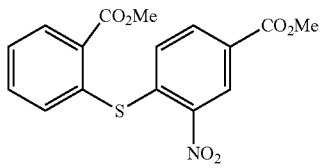

To a stirred solution of methyl 4-fluoro-3-nitrobenzoate 12 (30 g, 150.67 mmol) in DMF (300 mL) under inert atmosphere were added cesium carbonate (58.76 g, 180.8 mmol) and methyl 2-mercaptobenzoate 1 (22.6 mL, 165.47 mmol) at RT; heated to 55-60° C. and stirred for 2 h. The reaction was monitored by TLC; after completion of the reaction, the reaction mixture was diluted with water (1500 mL) and the precipitated solid was filtered to obtain the crude. The crude was washed with water (500 mL), hexane (200 mL) and dried in vacuo to afford compound 24 (48.8 g, 93%) as yellow solid. TLC: 20% EtOAc/hexanes ($R_f$: 0.4); $^1$H NMR (CDCl$_3$, 400 MHz): δ 8.85 (s, 1H), 7.99-7.92 (m, 2H), 7.66-7.56 (m, 3H), 6.93 (d, J=8.6 Hz, 1H), 3.94 (s, 3H), 3.79 (s, 3H).

Synthesis of methyl 3-amino-4-((2-(methoxycarbonyl) phenyl) thio) benzoate (25)

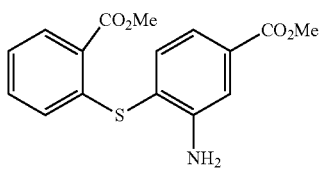

To a stirred solution of compound 24 (48 g, 138.32 mmol) in MeOH (1000 mL) under inert atmosphere was added 10% Pd/C (20 g, wet) at RT under hydrogen atmosphere in an autoclave (100 psi pressure) and stirred for 24 h. The reaction was monitored by TLC; after completion of the reaction, the reaction mixture was filtered through celite, washed with 50% MeOH/CH$_2$Cl$_2$ (500 mL). The filtrate was removed in vacuo to obtain the crude which as triturated with diethyl ether (200 mL), washed with hexane (200 mL) and dried in vacuo to afford compound 25 (40 g, 91%) as yellow solid. TLC: 10% EtOAc/hexanes ($R_f$: 0.3); $^1$H NMR (DMSO-d$_6$, 400 MHz): δ 7.95 (dd, J=7.8, 1.4 Hz, 1H), 7.48-7.35 (m, 3H), 7.23 (td, J=7.5, 1.1 Hz, 1H), 7.15 (dd, J=8.0, 1.8 Hz, 1H), 6.66 (dd, J=8.2, 0.8 Hz, 1H), 5.67 (br s, 2H), 3.88 (s, 3H), 3.84 (s, 3H).

Synthesis of 3-amino-4-((2-carboxyphenyl) thio) benzoic Acid (26)

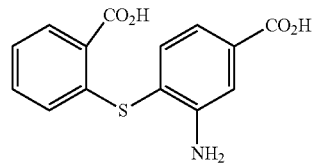

To a stirred solution of compound 25 (40 g, 126.18 mmol) in THF:H$_2$O (5:1, 400 mL) was added lithium hydroxide monohydrate (26 g, 619.0 mmol) at 0° C.; warmed to RT and stirred for 48 h. The reaction was monitored by TLC; after completion of the reaction, the volatiles were removed in vacuo. The pH of the residue was acidified with 2 N HCl to ~2. The precipitated solid was filtered and dried in vacuo to afford compound 26 (34.6 g, 95%) as an off-white solid. TLC: 30% EtOAc/hexanes ($R_f$: 0.1); $^1$H NMR (DMSO-d$_6$, 500 MHz): δ 13.00 (br s, 2H), 7.93 (dd, J=7.7, 1.0 Hz, 1H), 7.42 (s, 1H), 7.40-7.31 (m, 2H), 7.18 (t, J=7.4 Hz, 1H), 7.13 (dd, J=8.0, 1.6 Hz, 1H), 6.61 (d, J=7.8 Hz, 1H), 5.55 (br s, 2H).

Synthesis of 11-oxo-10,11-dihydrodibenzo[b,f][1,4] thiazepine-8-carboxylic Acid (27)

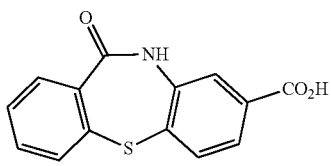

To a stirred solution of compound 26 (31 g, 107.26 mmol) in THF (600 mL) under inert atmosphere was added CDI (86.88 g, 536.29 mmol) at 0° C.; warmed to RT and stirred for 16 h. The reaction was monitored by TLC; after completion of the reaction, the reaction mixture was acidified with 2 N HCl to pH~4. The obtained solid was filtered and further dried by using toluene (2×200 mL) to afford compound 27 (26 g, 90%) as white solid. TLC: 10% MeOH/CH$_2$Cl$_2$ ($R_f$: 0.3); $^1$H NMR (DMSO-d$_6$, 400 MHz): δ 13.22 (br s, 1H), 10.81 (s, 1H), 7.78 (s, 1H), 7.72-7.64 (m, 3H), 7.57-7.44 (m, 3H).

Synthesis of methyl 11-oxo-10,11-dihydrodibenzo[b,f][1,4]thiazepine-8-carboxylate (28)

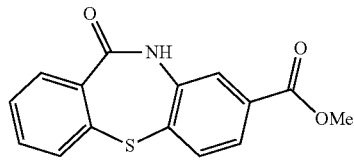

28

To a stirred solution of 27 (500 mg, 1.84 mmol) in MeOH:CH$_2$Cl$_2$ (1:1, 20 mL) under argon atmosphere was added CH$_2$N$_2$ (in situ prepared using N-nitrosomethyl urea (0.95 g, 9.2 mmol)+KOH (0.51 g, 9.22 mmol) at 0° C.; warmed to RT and stirred for 1 h. The reaction was monitored by TLC; after completion of the reaction, the volatiles were removed in vacuo to obtain the crude. The crude was purified through silica gel column chromatography using 20% EtOAc/hexanes to afford compound 28 (450 mg, 86%) as white solid. TLC: 30% EtOAc/hexanes (R$_f$: 0.5); $^1$H-NMR (DMSO-d$_6$, 500 MHz): δ 10.82 (s, 1H), 7.82 (s, 1H), 7.75-7.69 (m, 3H), 7.58-7.63 (m, 3H), 3.82 (s, 3H).

Synthesis of methyl 11-oxo-10,11-dihydrodibenzo[b,f][1,4]thiazepine-8-carboxylate 5,5-dioxide (29)

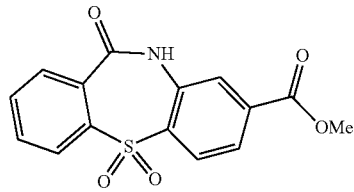

29

To a stirred solution of 28 (5 g, 17.54 mmol) in acetic acid (25 mL) was added 30% aqueous hydrogen peroxide (100 mL) at 0° C.; warmed to 50° C. and stirred for 72 h. The reaction was monitored by TLC; after completion of the reaction, the obtained solid was filtered, washed with water (100 mL), 10% EtOAc/hexanes (100 mL) and dried in vacuo to afford compound 29 (3.5 g, 64%) as white solid. TLC: 5% MeOH/CH$_2$Cl$_2$ (R$_f$: 0.3); $^1$H NMR (DMSO-d$_6$, 500 MHz): δ 11.58 (s, 1H), 8.09 (d, J=8.4 Hz, 1H), 8.01-7.95 (m, 3H), 7.93-7.83 (m, 3H), 3.88 (s, 3H);

Synthesis of 11-oxo-10,11-dihydrodibenzo[b,f][1,4]thiazepine-8-carboxylic acid 5,5-dioxide (30)

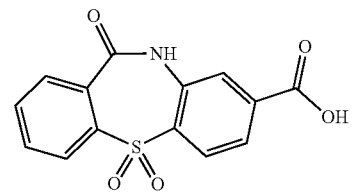

30

To a stirred solution of compound 29 (3.5 g, 11.04 mmol) in a mixture of THF:MeOH:H$_2$O (2:2:1, 25 mL) was added lithium hydroxide monohydrate (1.3 g, 33.12 mmol) portion wise for 10 min at 0° C.; warmed to RT and stirred for 3 h. The reaction was monitored by TLC; after completion of the reaction, the volatiles were removed in vacuo. The residue was diluted with water (20 mL) and acidified with 1 N HCl to pH~2. The obtained solid was filtered, washed with isopropyl alcohol (15 mL) and dried in vacuo to obtain compound 30 (2.8 g, 84%) as white solid. TLC: 5% MeOH/CH$_2$Cl$_2$ (R$_f$: 0.1); $^1$H NMR (DMSO-d$_6$, 400 MHz): δ 13.65 (br s, 1H), 11.55 (s, 1H), 8.07 (d, J=8.3 Hz, 1H), 8.03-7.82 (m, 6H).

Example 5: Synthesis of 11-oxo-10,11-dihydrodibenzo[b,f][1, 4]oxazepine-8-carboxylic Acid (35): A Common Intermediate

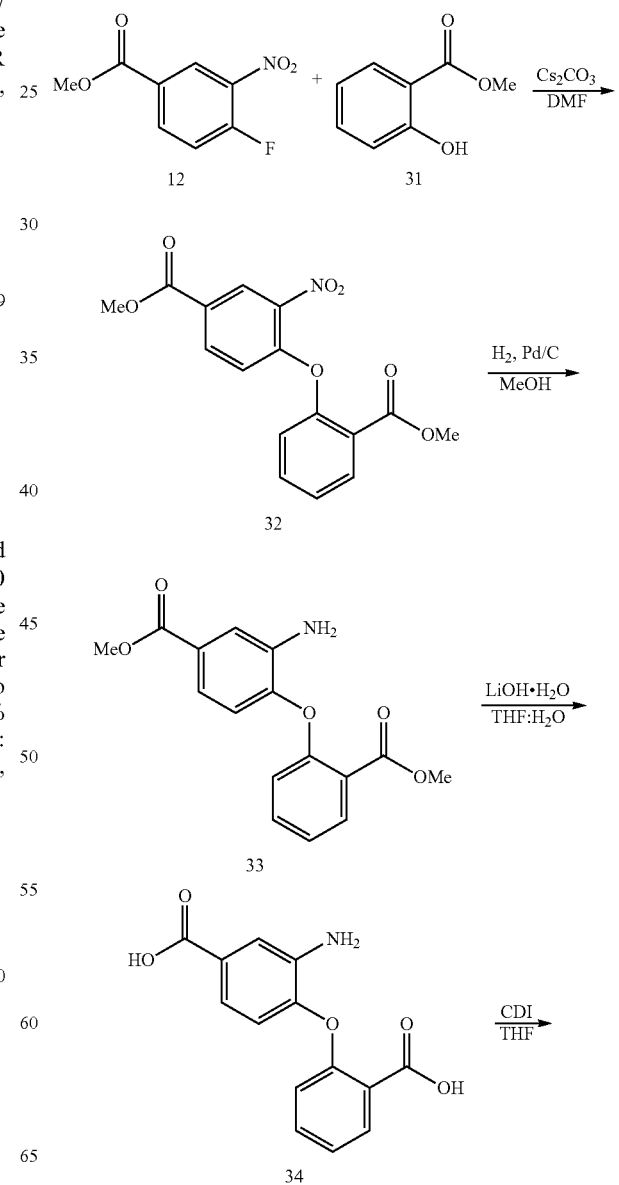

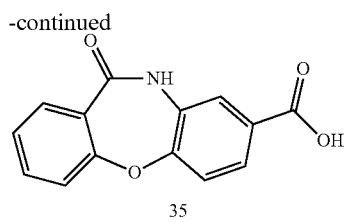

35

Synthesis of methyl 4-(2-(methoxycarbonyl) phenoxy)-3-nitrobenzoate (32)

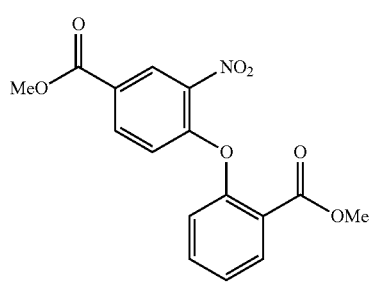

32

To a stirred solution of methyl 4-fluoro-3-nitrobenzoate 12 (5 g, 25.12 mmol) in DMF (75 mL) under argon atmosphere were added methyl 2-hydroxybenzoate 31 (4.2 g, 27.63 mmol), cesium carbonate (8.98 g, 27.64 mmol), at RT; heated to 100° C. and stirred for 2 h. The reaction was monitored by TLC; after completion of the reaction, the reaction mixture was diluted with ice-cold water (200 mL). The precipitated solid was filtered, washed with n-hexane (100 mL) and dried in vacuo to afford compound 32 (6.2 g, 75%) as an off-white solid. TLC: 30% EtOAc/hexanes ($R_f$: 0.4); $^1$H NMR (DMSO-$d_6$, 500 MHz): δ 8.54 (s, 1H), 8.11 (dd, J=8.8, 2.2 Hz, 1H), 8.02 (dd, J=7.7, 1.6 Hz, 1H), 7.80 (td, J=7.8, 1.7 Hz, 1H), 7.52 (t, J=7.4 Hz, 1H), 7.45 (d, J=7.8 Hz, 1H), 6.89 (d, J=8.7 Hz, 1H), 3.88 (s, 3H), 3.64 (s, 3H).

Synthesis of methyl 3-amino-4-(2-(methoxycarbonyl) phenoxy) benzoate (33)

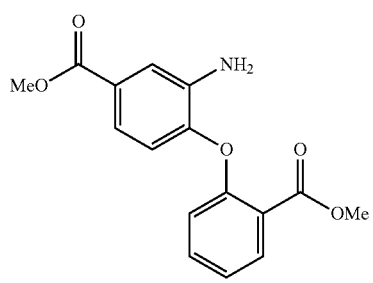

33

To a stirred solution of compound 32 (2 g, 6.04 mmol) in MeOH (50 mL) was evacuated for 5 min and added 10% Pd/C (1 g, 50% wet) under argon atmosphere at RT and stirred under hydrogen atmosphere (balloon pressure) at RT for 16 h. The reaction was monitored by TLC; after completion of the reaction, the reaction mixture was filtered through celite and washed with 20% MeOH/CH$_2$Cl$_2$ (200 mL). The filtrate was concentrated in vacuo to obtain the crude. The crude was purified by combiflash chromatography using 20% EtOAc/hexanes to afford compound 33 (1.4 g, 77%) as an off-white solid. TLC: 30% EtOAc/hexanes ($R_f$: 0.3); $^1$H NMR (DMSO-$d_6$, 400 MHz): δ 7.84 (dd, J=7.7, 1.6 Hz, 1H), 7.61-7.55 (m, 1H), 7.44 (s, 1H), 7.27 (t, J=7.2 Hz, 1H), 7.13 (dd, J=8.3, 2.0 Hz, 1H), 7.00 (d, J=8.0 Hz, 1H), 6.65 (d, J=8.3 Hz, 1H), 5.30 (br s, 2H), 3.80 (s, 3H), 3.74 (s, 3H).

Synthesis of 3-amino-4-(2-carboxyphenoxy) benzoic Acid (34)

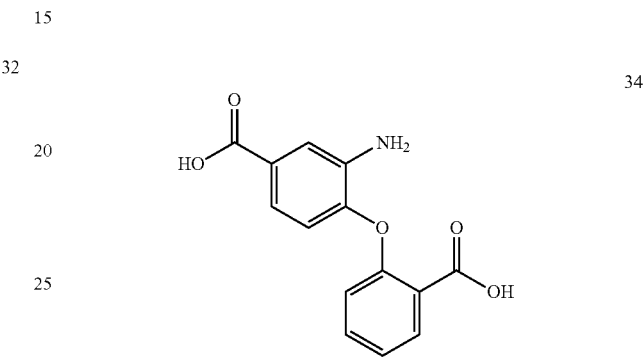

34

To a stirred solution of compound 33 (1.4 g, 4.65 mmol) in THF:H$_2$O (3:1, 40 mL) was added lithium hydroxide monohydrate (976 mg, 23.23 mmol) at RT; heated to reflux and stirred for 2 h. The reaction was monitored by TLC; after completion of the reaction, the volatiles were removed in vacuo. The pH of the residue was acidified to ~2 with 2 N HCl. The precipitated solid was filtered, washed with water (20 mL), n-pentane (20 mL) and dried in vacuo to afford compound 34 (700 mg, 56%) as an off-white solid. TLC: 30% EtOAc/hexanes ($R_f$: 0.1); $^1$H NMR (DMSO-$d_6$, 400 MHz): δ 7.86 (dd, J=7.7, 1.6 Hz, 1H), 7.63 (s, 1H), 7.62-7.57 (m, 1H), 7.37 (d, J=7.3 Hz, 1H), 7.31 (t, J=7.3 Hz, 1H), 7.06 (d, J=8.0 Hz, 1H), 6.69 (d, J=8.5 Hz, 1H).

Synthesis of 11-oxo-10,11-dihydrodibenzo[b,f][1,4]oxazepine-8-carboxylic Acid (35)

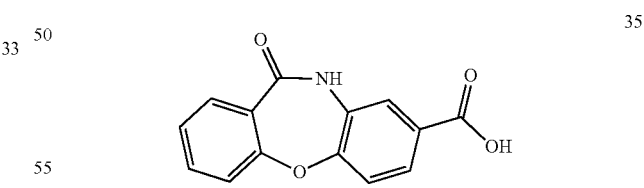

35

To a stirred solution of compound 34 (700 mg, 2.56 mmol) in THF (20 mL) under argon atmosphere was added CDI (2.07 g, 12.77 mmol) at RT and stirred for 24 h. The reaction was monitored by TLC; after completion of the reaction, the volatiles were removed in vacuo. The pH of the residue was acidified to ~2 using 2 N HCl. The precipitated solid was filtered, washed with n-pentane (50 mL) and dried in vacuo to afford compound 35 (450 mg, 69%) as an off-white solid. TLC: 10% MeOH/CH$_2$Cl$_2$ ($R_f$: 0.2); $^1$H NMR (DMSO-$d_6$, 400 MHz): δ 13.03 (br s, 1H), 10.65 (s, 1H), 7.81-7.76 (m, 2H), 7.70 (dd, J=8.4, 2.2 Hz, 1H), 7.67-7.61 (m, 1H), 7.43 (d, J=8.4 Hz, 1H), 7.40-7.31 (m, 2H).

Example 6: Synthesis of 11-oxo-10,11-dihydro-5H-dibenzo[b,e][1,4]diazepine-8-carboxylic Acid (40): A Common Intermediate

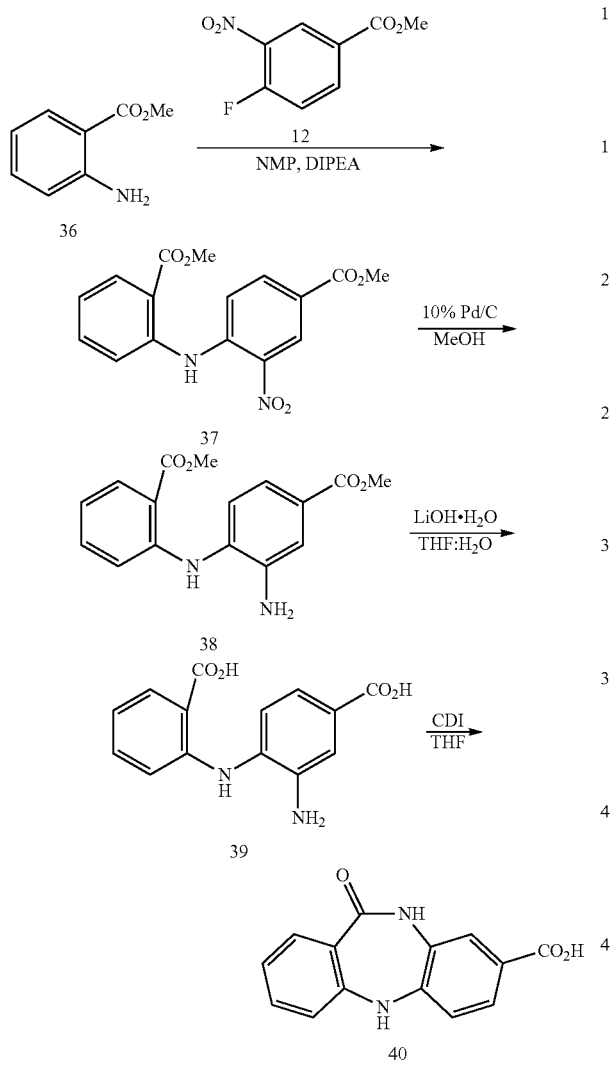

Synthesis of methyl 4-((2-(methoxycarbonyl) phenyl) amino)-3-nitrobenzoate (37)

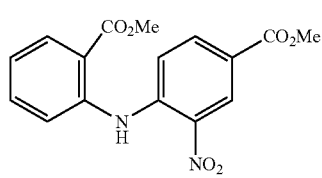

To a stirred solution of methyl 2-aminobenzoate 36 (5 g, 33.07 mmol) in N-Methyl-2-pyrrolidone (13 mL) under inert atmosphere were added diisopropylethylamine (18 mL, 103.46 mmol), methyl 4-fluoro-3-nitrobenzoate 12 (9.87 g, 49.21 mmol) at RT; heated to 120° C. in a sealed tube and stirred for 14 h. The reaction was monitored by TLC; after completion of the reaction, the reaction mixture was diluted with diethyl ether (100 mL) and stirred for 1 h. The obtained solid was filtered, washed with EtOAc (100 mL) and dried in vacuo to afford compound 37 (2.9 g, 26%) as yellow solid. TLC: 30% EtOAc/hexanes ($R_f$: 0.4); $^1$H NMR (DMSO-$d_6$, 400 MHz): δ 11.13 (s, 1H), 8.67 (s, 1H), 8.11-7.94 (m, 2H), 7.70-7.62 (m, 2H), 7.58 (d, J=9.0 Hz, 1H), 7.32-7.27 (m, 1H), 3.87 (s, 6H).

Synthesis of methyl 3-amino-4-((2-(methoxycarbonyl) phenyl) amino) benzoate (38)

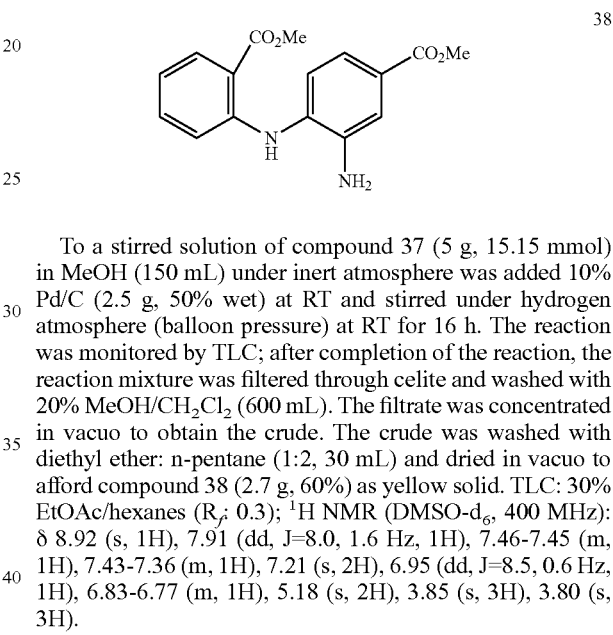

To a stirred solution of compound 37 (5 g, 15.15 mmol) in MeOH (150 mL) under inert atmosphere was added 10% Pd/C (2.5 g, 50% wet) at RT and stirred under hydrogen atmosphere (balloon pressure) at RT for 16 h. The reaction was monitored by TLC; after completion of the reaction, the reaction mixture was filtered through celite and washed with 20% MeOH/CH$_2$Cl$_2$ (600 mL). The filtrate was concentrated in vacuo to obtain the crude. The crude was washed with diethyl ether: n-pentane (1:2, 30 mL) and dried in vacuo to afford compound 38 (2.7 g, 60%) as yellow solid. TLC: 30% EtOAc/hexanes ($R_f$: 0.3); $^1$H NMR (DMSO-$d_6$, 400 MHz): δ 8.92 (s, 1H), 7.91 (dd, J=8.0, 1.6 Hz, 1H), 7.46-7.45 (m, 1H), 7.43-7.36 (m, 1H), 7.21 (s, 2H), 6.95 (dd, J=8.5, 0.6 Hz, 1H), 6.83-6.77 (m, 1H), 5.18 (s, 2H), 3.85 (s, 3H), 3.80 (s, 3H).

Synthesis of 3-amino-4-((2-carboxyphenyl) amino) benzoic Acid (39)

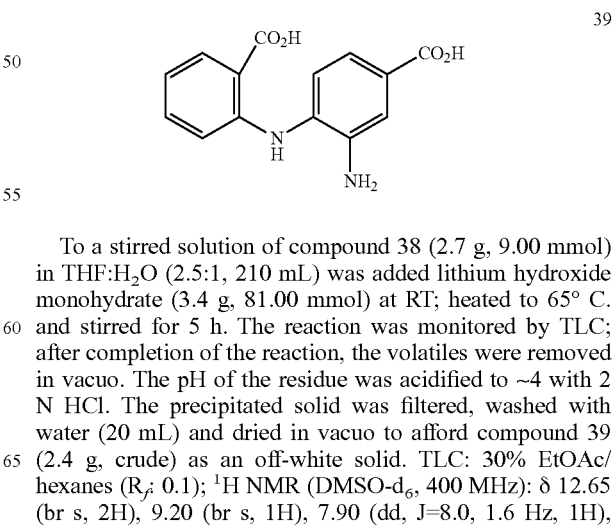

To a stirred solution of compound 38 (2.7 g, 9.00 mmol) in THF:H$_2$O (2.5:1, 210 mL) was added lithium hydroxide monohydrate (3.4 g, 81.00 mmol) at RT; heated to 65° C. and stirred for 5 h. The reaction was monitored by TLC; after completion of the reaction, the volatiles were removed in vacuo. The pH of the residue was acidified to ~4 with 2 N HCl. The precipitated solid was filtered, washed with water (20 mL) and dried in vacuo to afford compound 39 (2.4 g, crude) as an off-white solid. TLC: 30% EtOAc/hexanes ($R_f$: 0.1); $^1$H NMR (DMSO-$d_6$, 400 MHz): δ 12.65 (br s, 2H), 9.20 (br s, 1H), 7.90 (dd, J=8.0, 1.6 Hz, 1H), 7.44-7.42 (m, 1H), 7.39-7.35 (m, 1H), 7.20-7.18 (m, 2H), 6.92 (dd, J=8.5, 0.7 Hz, 1H), 6.79-6.75 (m, 1H), 5.08 (br s, 2H).

Synthesis of 11-oxo-10,11-dihydro-5H-dibenzo[b,e][1, 4]diazepine-8-carboxylic Acid (40)

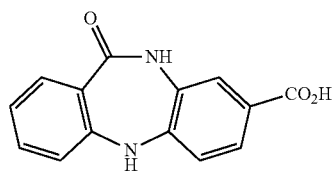

40

To a stirred solution of compound 39 (2.4 g, 8.82 mmol) in THF (80 mL) under inert atmosphere was added CDI (5.8 g, 35.29 mmol) at RT and stirred for 24 h. The reaction was monitored by TLC; after completion of the reaction, the volatiles were removed in vacuo. The pH of the residue was adjusted to ~2 using 2 N HCl. The precipitated solid was filtered, washed with n-pentane (50 mL) and dried in vacuo to afford compound 40 (1.9 g, 85%) as pale green solid. TLC: 10% MeOH/CH$_2$Cl$_2$ (R$_f$: 0.2); $^1$H NMR (DMSO-d$_6$, 400 MHz): δ 12.66 (br s, 1H), 9.93 (s, 1H), 8.26 (s, 1H), 7.70 (d, J=7.9 Hz, 1H), 7.58-7.50 (m, 2H), 7.36 (t, J=7.0 Hz, 1H), 7.02 (dd, J=17.4, 8.2 Hz, 2H), 6.91 (t, J=7.4 Hz, 1H).

Example 7: Synthesis of 11-methyl-6-oxo-6, 11-dihydro-5H-dibenzo[b,e]azepine-3-carboxylic Acid (51): A Common Intermediate

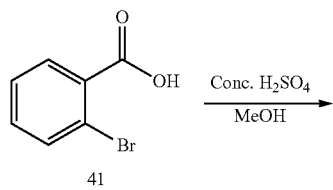

41

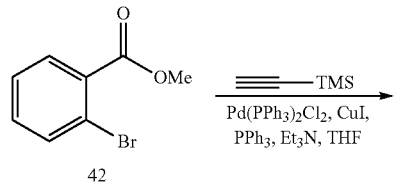

42

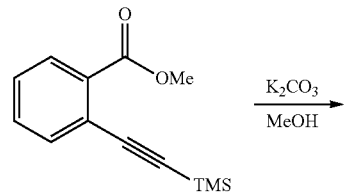

43

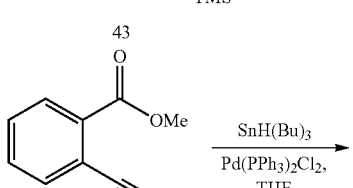

44

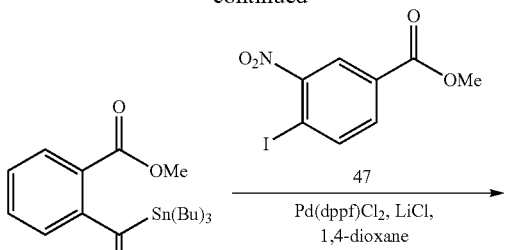

45

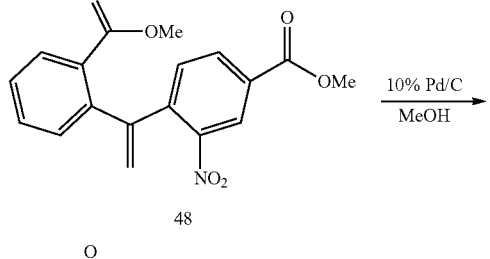

48

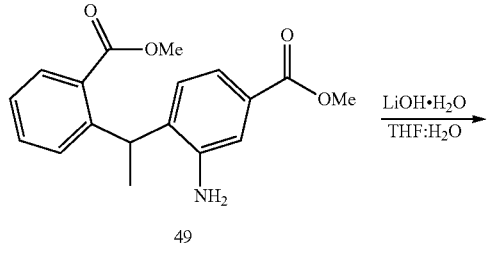

49

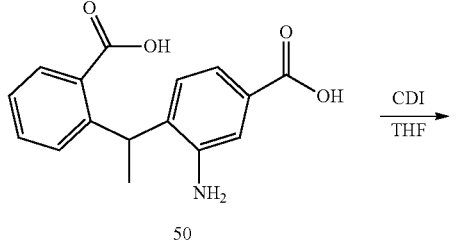

50

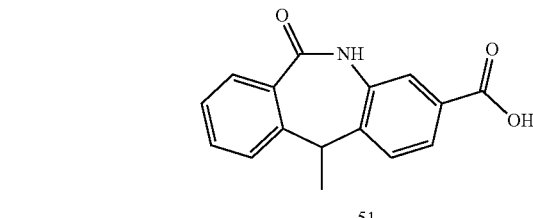

51

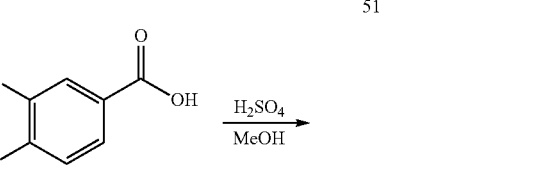

46

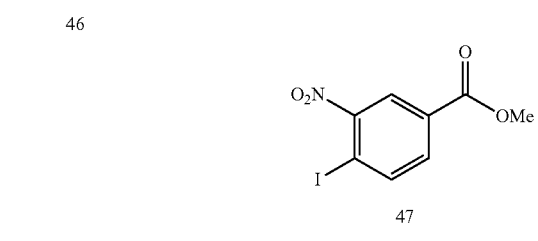

47

Synthesis of methyl 2-bromobenzoate (42)

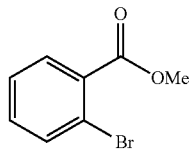

42

To a stirred solution of 2-bromobenzoic acid 41 (15 g, 74.62 mmol) in MeOH (150 mL) under inert atmosphere was added concentrated sulfuric acid (4 mL, 75.04 mmol) dropwise for 5 min at 0° C.; heated to reflux and stirred for 18 h. The reaction was monitored by TLC; after completion of the reaction, the volatiles were removed in vacuo. The residue was diluted with ice-cold water (100 mL) and extracted with EtOAc (2×100 mL). The combined organic extracts were dried over sodium sulfate, filtered and concentrated in vacuo to afford compound 42 (14 g, 93%) as colorless syrup. TLC: 10% EtOAc/hexanes ($R_f$: 0.5). $^1$H NMR (CDCl$_3$, 400 MHz): δ 7.81-7.77 (m, 1H), 7.70-7.64 (m, 1H), 7.39-7.30 (m, 2H), 3.94 (s, 3H).

Synthesis of methyl 2-((trimethylsilyl) ethynyl) benzoate (43)

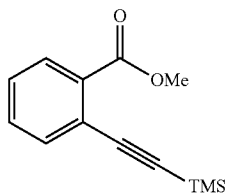

43

To a stirred solution of methyl 2-bromobenzoate 42 (14 g, 65.11 mmol) in THF (150 mL) under inert atmosphere were added triphenylphosphine (426 mg, 1.62 mmol), Pd(PPh$_3$)$_2$Cl$_2$ (4.57 g, 6.51 mmol), ethynyltrimethylsilane (18.4 mL, 130.23 mmol), triethyl amine (18.7 mL, 130.2 mmol) and purged under argon for 15 min. To this was added copper iodide (1.23 g, 6.51 mmol) at RT and stirred for 16 h. The reaction was monitored by TLC; after completion of the reaction, the reaction mixture was filtered through celite washed with EtOAc (200 mL). The filtrate was washed with water (150 mL), dried over sodium sulfate, filtered and concentrated in vacuo to obtain the crude. The crude was purified through silica gel column chromatography using 2% EtOAc/hexanes to afford compound 43 (11 g, 73%) a colorless syrup. TLC: 5% EtOAc/hexanes ($R_f$: 0.5); $^1$H NMR (CDCl$_3$, 400 MHz) δ 7.92-7.88 (m, 1H), 7.60-7.55 (m, 1H), 7.44 (td, J=7.6, 1.5 Hz, 1H), 7.36 (td, J=7.6, 1.3 Hz, 1H), 3.92 (s, 3H), 0.27 (s, 9H).

Synthesis of methyl 2-ethynylbenzoate (44)

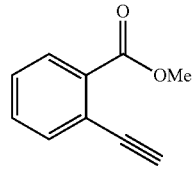

44

To a stirred solution of compound 43 (45 g, 193.96 mmol) in MeOH (500 mL) under inert atmosphere was added potassium carbonate (40 g, 290.94 mmol) at RT and stirred for 4 h. The reaction was monitored by TLC; after completion of the reaction, the reaction mixture was filtered through celite washed with CH$_2$Cl$_2$ (2×500 mL). The filtrate was removed in vacuo to obtain the crude. The crude was as purified through silica gel column chromatography using 2% EtOAc/hexanes to afford compound 44 (31 g, 33%) as colorless syrup. TLC: 5% EtOAc/hexanes ($R_f$: 0.5); $^1$H NMR (CDCl$_3$, 400 MHz): δ 7.97-7.91 (m, 1H), 7.62 (dd, J=7.7, 1.1 Hz, 1H), 7.47 (td, J=7.6, 1.5 Hz, 1H), 7.40 (td, J=7.7, 1.4 Hz, 1H), 3.38 (s, 1H), 3.91 (s, 3H).

Synthesis of methyl 2-(1-(tributylstannyl) vinyl) benzoate (45)

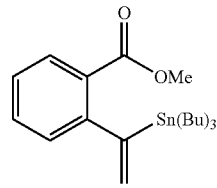

45

To a stirred solution of compound 44 (10 g, 62.5 mmol) and Pd(PPh$_3$)$_2$Cl$_2$ (877 mg, 1.25 mmol) in THF (37 mL) under inert atmosphere was added tributyltin hydride (20.43 mL, 75 mmol) at RT and stirred for 2.5 h. The reaction was monitored by TLC; after completion of the reaction, the volatiles were removed in vacuo to obtain the crude. The crude was purified through silica gel column chromatography using 2% EtOAc/hexanes to afford compound 45 (28 g, 54%) as colorless syrup. TLC: 5% EtOAc/hexanes ($R_f$: 0.8); $^1$H NMR (CDCl$_3$, 400 MHz): δ 7.87 (dd, J=7.8, 0.9 Hz, 1H), 7.41 (td, J=7.6, 1.4 Hz, 1H), 7.21 (td, J=7.6, 1.3 Hz, 1H), 7.01 (dd, J=7.7, 0.9 Hz, 1H), 5.67 (d, J=2.8 Hz, 1H), 5.38 (d, J=2.9 Hz, 1H), 3.82 (s, 3H), 1.49-1.39 (m, 6H), 1.30-1.20 (m, 6H), 0.90-0.83 (m, 15H).

Synthesis of methyl 4-iodo-3-nitrobenzoate (47)

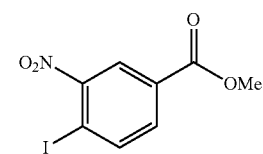

47

To a stirred solution of 4-iodo-3-nitrobenzoic acid 46 (15 g, 51.36 mmol) in MeOH (150 mL) under inert atmosphere was added concentrated sulphuric acid (15 mL) dropwise for 10 min at 0° C.; warmed to RT at stirred for 16 h. The reaction was monitored by TLC; after completion of the reaction, the volatiles were removed in vacuo. The residue was diluted with ice-cold water (500 mL) and extracted with EtOAc (3×100 mL). The combined organic extracts were washed saturated sodium bicarbonate solution (2×100 mL) dried over sodium sulfate, filtered and concentrated in vacuo to afford compound 47 (13 g, 83%) as an off-white solid. TLC: 30% EtOAc/hexanes ($R_f$: 0.8); $^1$H NMR (CDCl$_3$, 500 MHz) δ 8.45 (s, 1H), 8.15 (d, J=8.4 Hz, 1H), 7.88 (dd, J=8.2, 1.9 Hz, 1H), 3.97 (s, 3H).

Synthesis of methyl 4-(1-(2-(methoxycarbonyl) phenyl) vinyl)-3-nitrobenzoate (48)

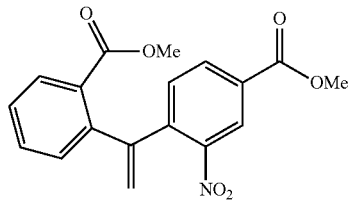

48

To a stirred solution of compound 45 (25 g, 5.52 mmol) in 1, 4-dioxane (40 mL) under inert atmosphere in a sealed tube were added methyl 4-iodo-3-nitrobenzoate 47 (1.86 g, 6.08 mmol), lithium chloride (813 mg, 19.35 mmol) and purged under argon for 20 min. To this was added Pd(dppf)Cl$_2$ (2 g, 2.76 mmol) at RT; heated to 120° C. and stirred for 16 h. The reaction was monitored by TLC; after completion of the reaction, the reaction mixture was filtered through celite washed with EtOAc (2×50 mL). The filtrate was washed with water (2×50 mL), dried over sodium sulfate, filtered and concentrated in vacuo to afford compound 48 (1.3 g, 70%) colorless syrup. TLC: 20% EtOAc/hexanes ($R_f$: 0.4); $^1$H-NMR (CDCl$_3$, 400 MHz): δ 8.30 (s, 1H), 8.17 (dd, J=8.2, 1.8 Hz, 1H), 7.69-7.65 (m, 2H), 7.52-7.42 (m, 2H), 7.40-7.35 (m, 1H), 5.61 (s, 1H), 5.58 (s, 1H), 3.96 (s, 3H), 3.58 (s, 3H).

Synthesis of methyl 3-amino-4-(1-(2-(methoxycarbonyl) phenyl) ethyl) benzoate (49)

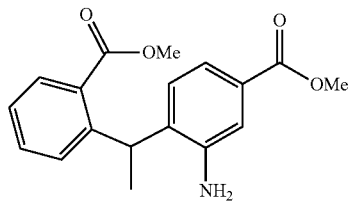

49

To a stirred solution of compound 48 (100 g, 0.29 mmol) in MeOH (10 mL) under inert atmosphere was added 10% Pd/C (40 mg, dry) at RT and stirred under hydrogen atmosphere (balloon pressure) for 16 h. The reaction was monitored by TLC; after completion of the reaction, the reaction mixture was filtered through celite, washed with CH$_2$Cl$_2$ (2×50 mL). The filtrate was concentrated in vacuo to afford compound 49 (70 mg, 77%) as colorless syrup. TLC: 20% EtOAc/hexanes ($R_f$: 0.7); $^1$H-NMR (DMSO-d$_6$, 500 MHz): δ 7.68 (dd, J=7.8, 1.2 Hz, 1H), 7.46 (td, J=7.6, 1.4 Hz, 1H), 7.32 (td, J=7.5, 1.0 Hz, 1H), 7.24 (s, 1H), 7.21-7.15 (m, 2H), 7.14-7.10 (m, 1H), 5.09 (s, 2H), 4.85 (q, J=6.9 Hz, 1H), 3.79 (s, 6H), 1.46 (d, J=7.0 Hz, 3H).

Synthesis of 3-amino-4-(1-(2-carboxyphenyl) ethyl) benzoic acid (50)

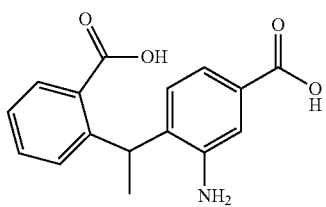

50

To a stirred solution of compound 49 (1.4 g, 4.47 mmol) in THF:H$_2$O (4:1, 20 mL) was added lithium hydroxide monohydrate (1.07 g, 22.3 mmol) at RT and heated to 70° C. and stirred for 6 h. The reaction was monitored by TLC; after completion of the reaction, the volatiles were removed in vacuo. The pH of the residue was acidified with 2 N HCl to ~4. The precipitated solid was filtered, washed with water (50 mL), n-pentane (30 mL) and dried in vacuo to afford compound 50 (900 mg, 71%) as an off-white solid. TLC: 10% MeOH/CH$_2$Cl$_2$ ($R_f$: 0.2); $^1$H-NMR (DMSO-d$_6$, 500 MHz): δ 12.50 (br s, 1H), 7.70 (dd, J=7.8, 1.2 Hz, 1H), 7.40 (td, J=7.6, 1.3 Hz, 1H), 7.28-7.23 (m, 2H), 7.19-7.17 (m, 2H), 7.09 (d, J=7.8 Hz, 1H), 4.98 (q, J=6.9 Hz, 1H), 1.44 (d, J=6.9 Hz, 3H).

Synthesis of 11-methyl-6-oxo-6, 11-dihydro-5H-dibenzo[b,e]azepine-3-carboxylic Acid (51)

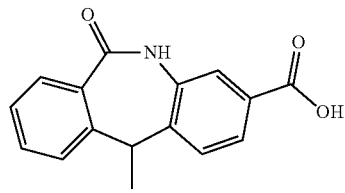

51

To a stirred solution of compound 50 (900 mg, 3.15 mmol) in THF (20 mL) under inert atmosphere was added CDI (2.5 g, 15.7 mmol) at RT and stirred for 16 h. The reaction was monitored by TLC; after completion of the reaction, the volatiles were removed in vacuo. The residue was diluted with water (15 mL) and pH was adjusted to ~4 with 2 N HCl The obtained solid was filtered washed with water (30 mL), diethyl ether (20 mL) and dried in vacuo to afford compound 51 (750 mg, 89%) as an off-white solid. TLC: 10% MeOH/CH$_2$Cl$_2$ ($R_f$: 0.3); LC-MS: 96.89%; 267.9 (M$^+$+1); (column; Ascentis Express C18, (50×3.0 mm, 2.7 μm); RT 2.14 min. 0.025% Aq. TFA+5% ACN: ACN+5% 0.025% Aq. TFA, 1.2 mL/min).

Example 8: Commercially Available Amines Used for Coupling

The following amines were obtained from commercial sources:

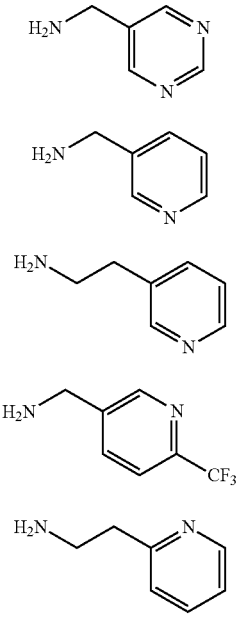

52

53

54

55

56

Preparation of the Amines for Coupling

Example 9: Synthesis of 4-(5-(aminomethyl)-1,3,4-thiadiazol-2-yl)phenol hydrochloride (63)

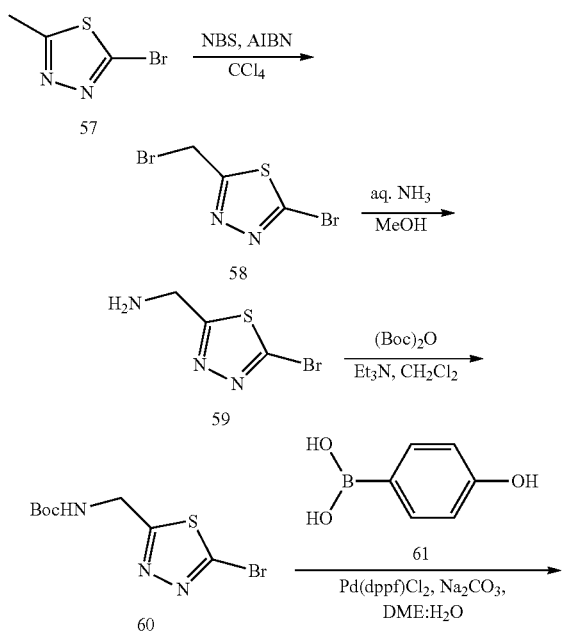

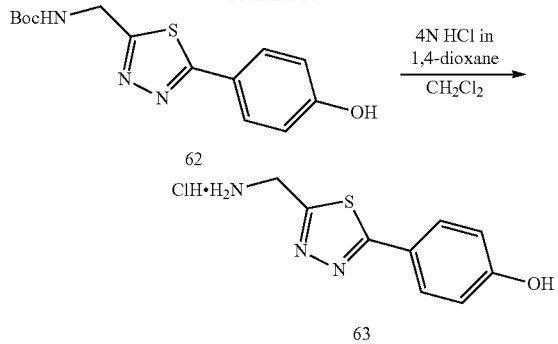

62

63

Synthesis of 2-bromo-5-(bromomethyl)-1, 3, 4-thiadiazole (58)

To a stirring solution of 2-bromo-5-methyl-1, 3, 4-thiadiazole 57 (2.7 g, 15.08 mmol) in CCl$_4$ (50 mL) under inert atmosphere were added N-bromosuccinimide (2.68 g, 15.08 mmol) and AIBN (247 mg, 1.50 mmol) at RT; heated to 80° C. and stirred for 24 h. The reaction was monitored by TLC; after completion of the reaction, the reaction mixture was filtered. The filtrate was concentrated in vacuo to obtain the crude. The residue was diluted with water (75 mL) and extracted with EtOAc (2×75 mL). The combined organic extracts were dried over sodium sulfate and concentrated in vacuo to the crude. The crude was purified through silica gel flash column chromatography using 5-7% EtOAc/hexanes to afford compound 58 (800 mg, 21%) as an off-white solid. TLC: 10% EtOAc/hexanes (R$_f$: 0.8); $^1$H NMR (400 MHz, DMSO-d$_6$): δ 5.14 (s, 2H)

Synthesis of (5-bromo-1, 3, 4-thiadiazol-2-yl) methanamine (59)

To a stirring solution of 2-bromo-5-(bromomethyl)-1, 3, 4-thiadiazole 58 (800 mg, 3.11 mmol) in MeOH (10 mL) under inert atmosphere in a sealed tube was added methanolic ammonia (20 mL) at 0° C.; warmed to RT and stirred for 16 h. The reaction was monitored by TLC; after completion of the reaction, the volatiles were removed in vacuo to the crude. The crude was triturated using diethyl ether (2×10 mL) and dried in vacuo to afford crude compound 59 (800 mg) as an off-white solid. TLC: 10% EtOAc/hexanes (R$_f$: 0.8); $^1$H-NMR (DMSO-d$_6$, 400 MHz): δ 7.32-7.68 (m, 2H), 4.62 (s, 2H);

Synthesis of tert-butyl ((5-bromo-1, 3, 4-thiadiazol-2-yl) methyl) carbamate (60)

To a stirring solution of (5-bromo-1, 3, 4-thiadiazol-2-yl) methanamine 59 (500 mg, 2.57 mmol) in CH$_2$Cl$_2$ (15 mL) under argon atmosphere were added triethylamine (0.50 mL, 3.09 mmol), Boc-anhydride (674 mg, 3.09 mmol) at 0° C.; warmed to RT and stirred for 6 h. The reaction was monitored by TLC; after completion of the reaction, the reaction mixture was diluted with water (50 mL) and extracted with CH$_2$Cl$_2$ (3×50 mL). The combined organic extracts were dried over sodium sulfate, filtered and concentrated in vacuo to obtain the crude. The crude was purified through silica gel column chromatography using 20% EtOAc/hexanes to afford compound 60 (550 mg, 23%) as an off-white solid.

TLC: 30% EtOAc/hexanes ($R_f$: 0.4); $^1$H NMR (500 MHz, DMSO-$d_6$): δ 7.84 (br s, 1H), 4.49 (d, J=6.1 Hz, 2H), 1.40 (s, 9H)

Synthesis of tert-butyl ((5-(4-hydroxyphenyl)-1, 3, 4-thiadiazol-2-yl) methyl) carbamate (62)

To a stirring solution of tert-butyl ((5-bromo-1, 3, 4-thiadiazol-2-yl) methyl) carbamate 60 (800 mg, 2.73 mmol) in 1, 2-dimethoxy ethane: $H_2O$ (4:1, 20 mL) under inert atmosphere were added (4-hydroxyphenyl) boronic acid 61 (453 mg, 3.28 mmol) and sodium carbonate (1 g, 9.58 mmol) in at RT and purged under argon atmosphere for 30 min. To this was added Pd(dppf)Cl$_2$ (200 mg, 0.27 mmol) and heated to 100° C. and stirred for 16 h. The reaction was monitored by TLC; after completion of the reaction, the reaction mixture was diluted with water (75 mL) and extracted with EtOAc (2×75 mL). The combined organic extracts were dried over sodium sulfate and concentrated in vacuo to obtain the crude. The crude was purified through silica gel column chromatography using 3% MeOH/CH$_2$Cl$_2$ to afford compound 62 (500 mg, 59%) as an off-white solid. TLC: 5% MeOH/CH$_2$Cl$_2$ ($R_f$: 0.2). $^1$H NMR (500 MHz, DMSO-$d_6$): δ 10.14 (s, 1H), 7.82-7.77 (m, 2H), 7.60-7.46 (m, 1H), 6.89 (d, J=8.4 Hz, 2H), 4.49 (d, J=5.8 Hz, 2H), 1.41 (s, 9H); LC-MS: 89.09%; 307.9 (M$^+$+1); (column; Ascentis Express C18, (50×3.0 mm, 2.7 μm); RT 2.10 min. 0.025% Aq. TFA+5% ACN: ACN+5% 0.025% Aq. TFA, 1.2 mL/min);

Synthesis of 4-(5-(aminomethyl)-1, 3, 4-thiadiazol-2-yl) phenol hydrochloride (63)

To a stirring solution of tert-butyl ((5-(4-hydroxyphenyl)-1, 3, 4-thiadiazol-2-yl) methyl) carbamate 62 (500 mg, 1.62 mmol) in CH$_2$Cl$_2$ (10 mL) under inert atmosphere was added 4 N HCl in 1, 4-dioxane (10 mL) at 0° C.; warmed to RT and stirred for 4 h. The reaction was monitored by TLC; after completion of the reaction, the volatiles were removed in vacuo. The crude was titrated with EtOAc (2×5 mL), diethyl ether (2×10 mL) and dried in vacuo to afford compound 63 (400 mg, Quantitative) as an off-white solid. TLC: 40% EtOAc/hexanes ($R_f$: 0.1); $^1$H NMR (500 MHz, DMSO-$d_6$): δ 8.82 (br s, 3H), 7.82 (d, J=8.7 Hz, 2H), 6.95 (d, J=8.7 Hz, 2H), 4.70 (br s, 1H), 4.57 (br d, J=4.3 Hz, 2H); LC-MS: 94.61%; 207.9 (M$^+$+1); (column; X-select CSH C-18 (50×3.0 mm, 2.5 μm); RT 1.85 min. 2.5 mM NH$_4$OOCH (Aq)+5% ACN: ACN+5% 2.5 mM NH$_4$OOCH (Aq); 0.8 mL/min).

Example 10: Synthesis of (6-(4-methoxybenzyl) pyridin-3-yl) methanamine hydrochloride (72)

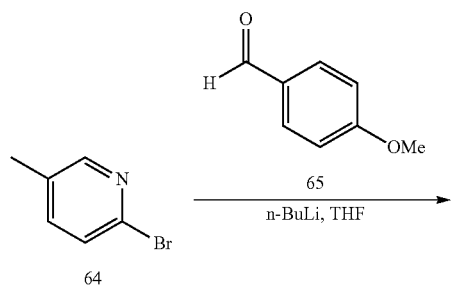

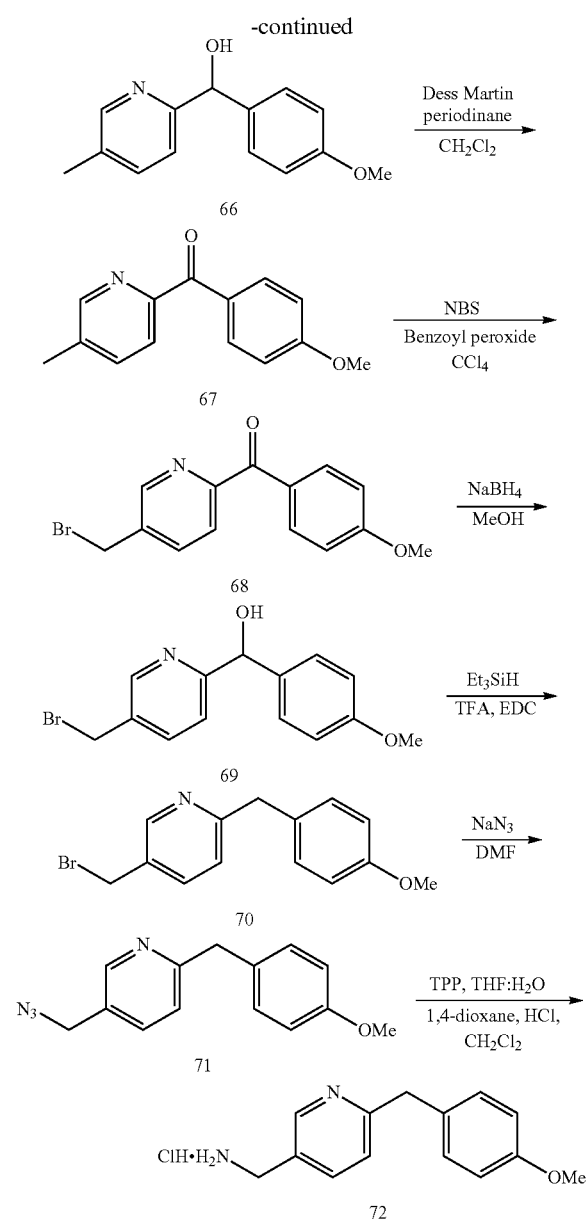

Synthesis of (4-methoxyphenyl) (5-methylpyridin-2-yl) methanol (66)

To a stirring solution 2-bromo-5-methylpyridine 64 (10 g, 58.13 mmol) in dry THF (200 mL) under inert atmosphere was added n-butyl lithium (1.6 M solution in hexane, 54 mL, 87.22 mmol) dropwise for 10 min at −78° C. and stirred for 30 min. To this was added 4-methoxybenzaldehyde 65 (9.48 g, 69.76 mmol) in dry THF (10 mL) at −78° C. for 10 min; warmed to 0° C. and stirred for 2 h. The reaction was monitored by TLC; after completion of the reaction, the reaction mixture was quenched with saturated ammonium chloride (20 mL) and extracted with EtOAc (2×200 mL). The combined organic extracts were dried over sodium sulfate, filtered and concentrated in vacuo to obtain the crude. The crude was purified through silica gel column chromatography using 30% EtOAc/hexanes to afford compound 66 (6.3 g, 47%) as an off-white solid. TLC: 30%

EtOAc/hexanes (R$_f$: 0.3); $^1$H-NMR (DMSO-d$_6$, 500 MHz): δ 8.26 (s, 1H), 7.56 (dd, J=7.8, 1.4 Hz, 1H), 7.41 (d, J=8.1 Hz, 1H), 7.26 (d, J=8.7 Hz, 2H), 6.83 (d, J=8.4 Hz, 2H), 5.87 (d, J=4.3 Hz, 1H), 5.61 (d, J=4.0 Hz, 1H), 3.70 (s, 3H), 2.24 (s, 3H); LC-MS: 95.28%; 230.0 (M$^+$+1); (column; Ascentis Express C-18, (50×3.0 mm, 2.7 μm); RT 1.35 min. 0.025% Aq. TFA+5% ACN: ACN+5% 0.025% Aq. TFA, 1.2 mL/min);

Synthesis of (4-methoxyphenyl) (5-methylpyridin-2-yl) methanone (67)

To a stirring solution of compound 66 (6 g, 26.20 mmol) in CH$_2$Cl$_2$ (200 mL) under argon atmosphere was added Dess-Martin periodinane (16.6 g, 39.30 mmol) at 0° C.; warmed to RT and stirred for 1 h. The reaction was monitored by TLC; after completion of the reaction, the reaction mixture was quenched with saturated NaHCO$_3$ solution and extracted with EtOAc (2×250 mL). The combined organic extracts were dried over sodium sulfate, filtered and concentrated in vacuo to obtain the crude. The crude was purified using silica gel column chromatography using 20% EtOAc/hexanes to afford compound 67 (3.35 g, 56%) as an off-white solid. TLC: 30% EtOAc/hexanes (R$_f$: 0.8); $^1$H NMR (DMSO-d$_6$, 400 MHz): δ 8.55 (s, 1H), 8.03 (d, J=8.9 Hz, 2H), 7.86 (s, 2H), 7.06 (d, J=8.9 Hz, 2H), 3.86 (s, 3H), 2.41 (s, 3H); LC-MS: 97.11%; 228.0 (M$^+$+1); (column; Ascentis Express C-18, (50×3.0 mm, 2.7 μm); RT 2.20 min. 0.025% Aq. TFA+5% ACN: ACN+5% 0.025% Aq. TFA, 1.2 mL/min);

Synthesis of (4-methoxyphenyl) (5-methylpyridin-2-yl) methanone (68)

To a stirring solution of compound 67 (3.45 g, 15.19 mmol) in CCl$_4$ (100 mL) under argon atmosphere were added N-bromosuccinimide (2.97 g, 16.71 mmol) and benzoylperoxide (367 mg, 1.51 mmol) at RT; heated to 80° C. and stirred for 6 h. The reaction was monitored by TLC; after completion of the reaction, the reaction mixture was diluted with CH$_2$Cl$_2$ (200 mL), washed with water (2×200 mL). The organic extract was dried over sodium sulfate, filtered and concentrated in vacuo to obtain the crude. The crude was purified through silica gel column chromatography using 7% EtOAc/hexanes to afford compound 68 (2.5 g, 54%) as white solid. TLC: 7% EtOAc/hexanes (R$_f$: 0.7); $^1$H-NMR (DMSO-d$_6$, 500 MHz): δ 8.78 (s, 1H), 8.11 (dd, J=8.0, 2.2 Hz, 1H), 8.02 (d, J=8.7 Hz, 2H), 7.93 (d, J=8.1 Hz, 1H), 7.08 (d, J=8.7 Hz, 2H), 4.85 (s, 2H), 3.86 (s, 3H); LC-MS: 76.09%; 305.8 (M$^+$+1); (column; Kinetex EVO C-18 (50×3.0 mm, 2.6 um); RT 3.06 min. 2.5 mM Aq. NH$_4$OOCH+5% ACN: ACN+5% 2.5 mM Aq.NH$_4$OOCH, 0.8 mL/min).

Synthesis of (5-(bromomethyl) pyridin-2-yl) (4-methoxyphenyl) methanol (69)

To a stirring solution of compound 68 (2.5 g, 8.19 mmol) in MeOH (100 mL) under argon atmosphere was added sodium borohydride (467 mg, 12.29 mmol) at 0° C. and stirred at the same temperature for 1 h. The reaction was monitored by TLC; after completion of the reaction, the reaction mixture was quenched with ice-cold water (50 mL) and extracted with CH$_2$Cl$_2$ (3×200 mL). The combined organic extracts were dried over sodium sulfate and concentrated in vacuo to obtain the crude which was triturated with n-hexane (30 mL) to afford compound 69 (2.2 g, 87%)

as yellow solid. TLC: 30% EtOAc/hexanes (R$_f$: 0.3); LC-MS: 74.95%; 309.9 (M+2)$^+$; (column; Ascentis Express C-18, (50×3.0 mm, 2.7 μm); RT 2.20 min. 0.025% Aq. TFA+5% ACN: ACN+5% 0.025% Aq. TFA, 1.2 mL/min);

Synthesis of 5-(bromomethyl)-2-(4-methoxybenzyl) pyridine (70)

To a stirring solution of compound 69 (2.2 g, 7.16 mmol) in 1, 2-dichloroethane (50 mL) under inert atmosphere were added triethylsilane (4.19 g, 35.83 mmol), trifluoroacetic acid (4.08 g, 35.83 mmol) at 0° C.; heated to 60-70° C. and stirred for 8 h. The reaction was monitored by TLC; after completion of the reaction, the volatiles were removed in vacuo. The crude was diluted with CH$_2$Cl$_2$ (200 mL), washed with water (2×150 mL). The organic extract was dried over sodium sulfate and concentrated in vacuo to obtain the crude. The crude was purified through silica gel column chromatography using 20% EtOAc/hexanes to afford compound 70 (800 mg, 40%) as brown syrup. TLC: 30% EtOAc/hexanes (R$_f$: 0.8); LC-MS: 67.00%; 291.8 (M$^+$+1), 293.9 (M+2)$^+$; (column; Kinetex EVO C-18 (50×3.0 mm, 2.6 um); RT 3.06 min. 2.5 mM Aq. NH$_4$OOCH+5% ACN: ACN+5% 2.5 mM Aq.NH$_4$OOCH, 0.8 mL/min).

Synthesis of 5-(azidomethyl)-2-(4-methoxybenzyl) pyridine (71)

To a stirring solution of compound 70 (800 mg, 2.74 mmol) in DMF (20 mL) under inert atmosphere was added sodium azide (536 mg, 8.244 mmol) at 0° C.; warmed to RT and stirred for 1 h. The reaction was monitored by TLC; after completion of the reaction, the reaction mixture was diluted with water (100 mL) and extracted with EtOAc (2×100 mL). The combined organic extracts were dried over sodium sulphate, filtered and concentrated in vacuo to afford crude compound 71 (1.5 g, 32% over 2 steps) as brown syrup. TLC: 20% EtOAc/hexanes (R$_f$: 0.4); $^1$H-NMR (DMSO-d$_6$, 500 MHz): δ 8.47 (s, 1H), 7.71 (dd, J=7.8, 2.0 Hz, 1H), 7.27 (d, J=8.1 Hz, 1H), 7.18 (d, J=8.4 Hz, 2H), 6.85 (d, J=8.4 Hz, 2H), 4.47 (s, 2H), 4.02 (s, 2H), 3.70 (s, 3H); LC-MS: 82.00%; 255.0 (M$^+$+1); (column; Kinetex EVO C-18 (50×3.0 mm, 2.6 um); RT 2.89 min. 2.5 mM Aq. NH$_4$OOCH+5% ACN: ACN+5% 2.5 mM Aq.NH$_4$OOCH, 0.8 mL/min).

Synthesis of (6-(4-methoxybenzyl) pyridin-3-yl) methanamine hydrochloride (72)

To a stirring solution of compound 71 (570 mg, crude) in THF:H$_2$O (20:5, 22 mL) was added triphenyl phosphine (1.17 g, 4.48 mmol) at 0° C.; warmed to RT and stirred for 16 h. The reaction was monitored by TLC; after completion of the reaction; the volatiles were removed in vacuo to obtain the crude amine (800 mg crude).

To the above crude amine (800 mg mg) in CH$_2$Cl$_2$ (20 mL) was added 4 N HCl in 1, 4-dioxane (5 mL) under inert atmosphere at 0° C. and stirred for 1 h. The reaction was monitored by TLC; after completion of the reaction, the volatiles were removed in vacuo. The crude was washed with triturated with EtOAc (5 mL), CH$_2$Cl$_2$ (5 mL) and dried in vacuo to afford compound 72 (450 mg, HCl salt, 76%) as an off-white solid. TLC: 5% MeOH/CH$_2$Cl$_2$ (R$_f$: 0.1); $^1$H-NMR (DMSO-d$_6$, 400 MHz): δ 8.80 (s, 1H), 8.55 (br s, 3H), 8.28 (d, J=6.9 Hz, 1H), 7.70 (d, J=8.0 Hz, 1H), 7.29 (d, J=8.7 Hz, 2H), 6.88 (d, J=8.7 Hz, 2H), 4.24 (s, 2H), 4.13 (q, J=5.6 Hz, 2H), 3.71 (s, 3H); LC-MS: 95.36%; 229.0

(M++1); column; Kinetex EVO C-18 (50×3.0 mm, 2.6 um); RT 1.55 min. 2.5 mM Aq. NH₄OOCH+5% ACN: ACN+5% 2.5 mM Aq.NH₄OOCH, 0.8 mL/min).

Example 11: Synthesis of (2-(trifluoromethyl) pyrimidin-5-yl) methanamine hydrochloride (77)

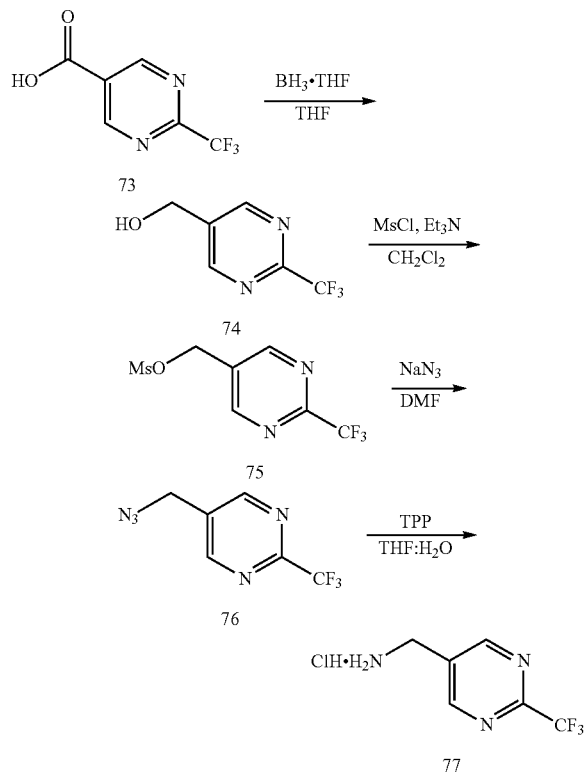

Synthesis of (2-(trifluoromethyl) pyrimidin-5-yl) methanol (74)

To a stirring solution of compound 73 (200 mg, 1.04 mmol) in THF (10 mL) under inert atmosphere was added Borane tetrahydrofuran complex (3.1 mL, 3.12 mmol; 1M in THF) drop wise for 15 min at 0° C.; stirred for 10 min. warmed to RT and stirred for 3 h. The reaction was monitored by TLC; after completion of the reaction, the reaction mixture was quenched with MeOH (5 mL) at 0° C. and diluted with EtOAc (30 mL). The organic layer washed with 10% sodium bicarbonate solution (20 mL) dried over sodium sulfate, filtered and concentrated in vacuo to obtain the crude. The crude was purified through silica gel column chromatography using 30% EtOAc/hexanes to afford compound 74 (80 mg, 43%) as colourless liquid. TLC: 70% EtOAc/hexanes (R$_f$: 0.1). ¹H NMR (500 MHz, DMSO-d₆) δ 8.99 (s, 2H), 5.64 (t, J=5.5 Hz, 1H), 4.68 (d, J=5.5 Hz, 2H); LC-MS: 92.60%; 179.2 (M++1); (column; X select CSH C-18 (50×3 mm, 2.5 μm); RT 1.78 min. 2.5 mM Aq. NH₄OAc: ACN, 0.8 mL/min);

Synthesis of (2-(trifluoromethyl) pyrimidin-5-yl) methyl methanesulfonate (75)

To a stirring solution of compound 74 (200 mg, 1.16 mmol) in CH₂Cl₂ (20 mL) under inert atmosphere were added triethylamine (0.48 mL, 3.48 mmol), methanesulfonyl chloride (0.13 mL, 1.75 mmol) at 0° C.; warmed to RT and stirred for 1 h. The reaction was monitored by TLC; after completion of the reaction, the reaction mixture was quenched with saturated sodium bicarbonate solution (25 mL) and extracted with CH₂Cl₂ (2×30 mL). The combined organic extracts were dried over sodium sulfate, filtered and concentrated in vacuo to afford crude compound 75 (220 mg crude) as off white solid. This material was taken up next reaction without purification. TLC: 50% EtOAc/hexanes (R$_f$: 0.5); LC-MS: 31.18%; 257.2 (M++1); (column; X select CSH C-18 (50×3 mm, 2.5 μm); RT 3.33 min. 2.5 mM Aq. NH₄OAC: ACN, 0.8 mL/min);

Synthesis of 5-(azidomethyl)-2-(trifluoromethyl) pyrimidine (76)

To a stirring solution of compound 75 (200 mg, 0.78 mmol) in DMF (2 mL) under argon atmosphere was added sodium azide (152 mg, 2.34 mmol) at RT and stirred for 3 h. The reaction was monitored by TLC; after completion of the reaction, the reaction mixture was filtered, washed with EtOAc (50 mL). The filtrate was washed with water (40 mL) dried over sodium sulfate, filtered and concentrated in vacuo to obtain the compound 76 (180 mg crude) as pale yellow oil. TLC: 50% EtOAc/hexanes (R$_f$: 0.8); LC-MS: 48.77%; 204.2 (M++1); (column; X select CSH C-18 (50×3 mm, 2.5 μm); RT 3.74 min. 2.5 mM Aq. NH₄OAc: ACN, 0.8 mL/min);

Synthesis of (2-(trifluoromethyl) pyrimidin-5-yl) methanamine hydrochloride (77)

To a stirring solution of compound 76 (180 mg, 0.88 mmol) in THF:H₂O (4:1, 10 mL) was added triphenyl phosphine (369 mg, 1.32 mmol) portion wise for 5 min at RT and stirred for 3 h. The reaction was monitored by TLC; after completion of the reaction, the volatiles were removed in vacuo. The residue was diluted with EtOAc (40 mL) and 1N HCl (20 mL). The aqueous layer was concentrated in vacuo to obtain the crude compound 77 (150 mg crude, HCl salt) as an off-white solid; which was carried forward for next step without further purification. TLC: 50% EtOAc/ hexanes (R$_f$: 0.1). LC-MS: 15.46%; 178.1 (M++1); (column; X-select CSH C-18 (50×3.0 mm, 2.5 μm); RT 0.5 min. 2.5 mM NH4OAc: ACN; 0.8 mL/min).

Example 12: Compound Preparation

Acids similar to compound 7 (compounds 7, 16, 23, 30, 35, 40, 51) were synthesized as mentioned in Example 1 and converted to final products either using commercially available amines or prepared amines employing typical procedure A and the results are captured in the Table 1:

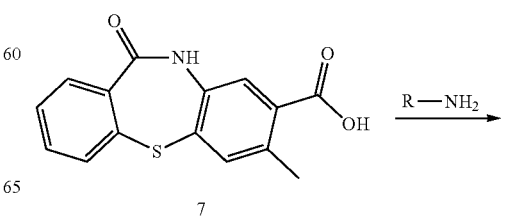

7

Typical Procedure A:

To a stirred solution of compound 7 (100 mg, 0.35 mmol) in DMF (5 mL) under inert atmosphere were added EDCI.HCl (95 mg, 0.55 mmol), HOBt (71 mg, 0.55 mmol), amine 52 (50 mg, 0.46 mmol) and diisopropylethylamine (0.2 mL, 1.05 mmol) at 0° C. warmed to RT and stirred for 16 h. The reaction was monitored by TLC; after completion of the reaction, the volatiles were removed in vacuo to obtain the crude. The crude was either directly dried in vacuo or triturated or purified through silica gel column chromatography to afford the desired compound.

TABLE 1

Synthesis from various acids and various amines

| Compound No. | Structure | Procedure, Intermediate, amine | Rx. Yield (%) | Mass Spec. Found | Mass Spec. Calculated | $^1$H-NMR |
|---|---|---|---|---|---|---|
| 495 | 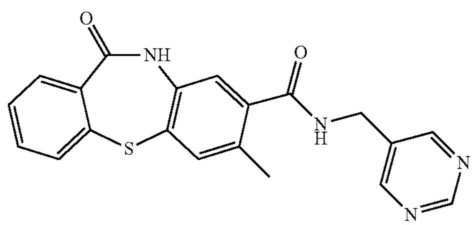 [SMILES: Cc1cc2c(cc1C(=O)NCc1cncnc1)NC(=O)c1ccccc1S2] | A, 7, 52 | 61 | 377.3 (M$^+$ + 1) | 376.10 for $C_{20}H_{16}N_4O_2S$ | $^1$H NMR (DMSO-d$_6$, 400 MHz): δ 10.62 (s, 1H), 9.10 (s, 1H), 8.91 (t, J = 5.7 Hz, 1H), 8.75 (s, 2H), 7.67 (dd, J = 1.6, 7.4, 1.6 Hz, 1H), 7.57-7.42 (m, 4H), 7.23 (s, 1H), 4.44 (d, J = 5.9 Hz, 2H), 2.23 (s, 3H) |
| 497 | 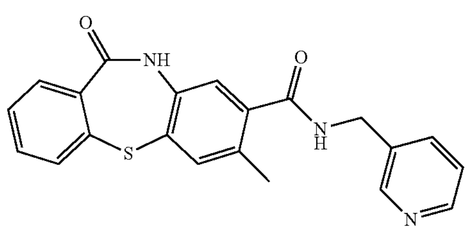 [SMILES: Cc1cc2c(cc1C(=O)NCc1cccnc1)NC(=O)c1ccccc1S2] | A, 7, 53 | 75 | 376.0 (M$^+$ + 1) | 375.10 for $C_{21}H_{17}N_3O_2S$ | $^1$H NMR (DMSO-d$_6$, 400 MHz): δ 10.63 (s, 1H), 8.87 (t, J = 5.9 Hz, 1H), 8.53 (s, 1H), 8.47 (dd, J = 4.8, 1.5 Hz, 1H), 7.74-7.65 (m, 2H), 7.56-7.41 (m, 4H), 7.36 (dd, J = 7.4, 5.1 Hz, 1H), 7.20 (s, 1H), 4.42 (d, J = 6.0 Hz, 2H), 2.23 (s, 3H) |
| 539 | 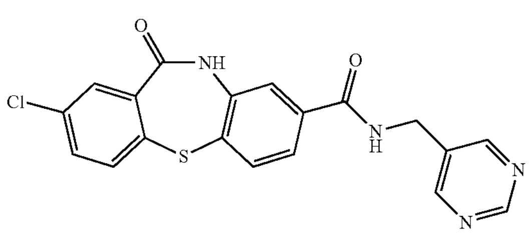 [SMILES: O=C(NCc1cncnc1)c1ccc2c(c1)NC(=O)c1cc(Cl)ccc1S2] | A, 16, 52 | 61 | 396.8 (M$^+$ + 1); | 396.04 for $C_{19}H_{13}ClN_4O_2S$ | $^1$H NMR (DMSO-d$_6$, 400 MHz): δ 10.91 (s, 1H), 9.17 (t, J = 5.6 Hz, 1H), 9.08 (s, 1H), 8.74 (s, 2H), 7.73-7.61 (m, 4H), 7.57-7.56 (m, 2H), 4.48 (d, J = 5.6 Hz, 2H); |

TABLE 1-continued

Synthesis from various acids and various amines

| Compound No. | Structure | Procedure, Intermediate, amine | Rx. Yield (%) | Mass Spec. Found | Mass Spec. Calculated | ¹H-NMR |
|---|---|---|---|---|---|---|
| 540 | 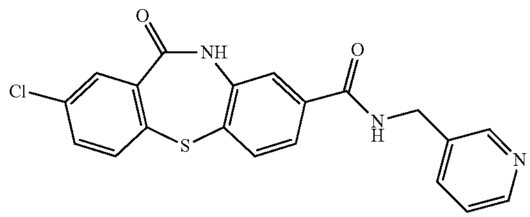 [SMILES: O=C(NCc1cccnc1)c1ccc2c(c1)NC(=O)c1cc(Cl)ccc1S2] | A, 16, 53 | 66 | 395.8 (M⁺ + 1); | 395.05 for $C_{20}H_{14}ClN_3O_2S$ | ¹H NMR (DMSO-d₆, 400 MHz): δ 10.91 (s, 1H), 9.15 (t, J = 5.8 Hz, 1H), 8.52 (s, 1H), 8.48-8.42 (m, 1H), 7.73-7.61 (m, 5H), 7.57-7.56 (m, 2H), 7.34 (dd, J = 8.0, 4.5 Hz, 1H), 4.47 (d, J = 5.7 Hz, 2H); |
| 542 | 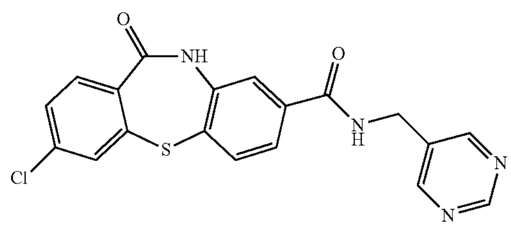 [SMILES: O=C(NCc1cncnc1)c1ccc2c(c1)NC(=O)c1ccc(Cl)cc1S2] | A, 23, 52 | 45 | 396.8 (M⁺ + 1); | 396.04 for $C_{19}H_{13}ClN_4O_2S$ | ¹H-NMR (DMSO-d₆, 400 MHz): δ 10.85 (s, 1H), 9.17 (t, J = 5.6 Hz, 1H), 9.08 (s, 1H), 8.74 (s, 2H), 7.74-7.61 (m, 5H), 7.53 (dd, J = 8.4, 2.1 Hz, 1H), 4.48 (d, J = 5.6 Hz, 2H); |
| 543 | 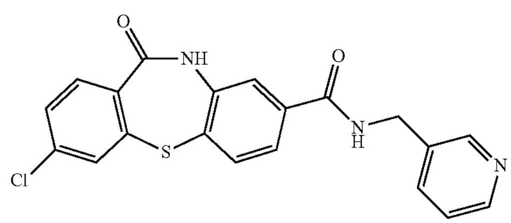 [SMILES: O=C(NCc1cccnc1)c1ccc2c(c1)NC(=O)c1ccc(Cl)cc1S2] | A, 23, 53 | 35 | 395.8 (M⁺ + 1); | 395.05 for $C_{20}H_{14}ClN_3O_2S$ | ¹H-NMR (DMSO-d₆, 400 MHz): δ 10.86 (s, 1H), 9.16 (t, J = 5.7 Hz, 1H), 8.53 (s, 1H), 8.45 (d, J = 3.7 Hz, 1H), 7.76-7.61 (m, 6H), 7.54 (dd, J = 8.4, 2.1 Hz, 1H), 7.34 (dd, J = 7.8, 4.9 Hz, 1H), 4.47 (d, J = 5.7 Hz, 2H); |
| 807 | 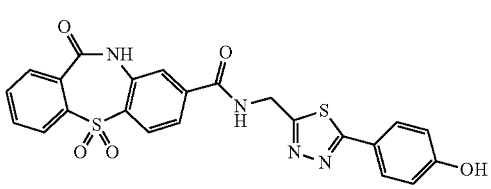 [SMILES: O=C(NCc1nnc(-c2ccc(O)cc2)s1)c1ccc2c(c1)NC(=O)c1ccccc1S2(=O)=O] | A, 30, 63 | 30 | 493.0 (M⁺ + 1); | 492.06 for $C_{23}H_{16}N_4O_5S_2$ | ¹H-NMR (DMSO-d₆, 400 MHz): δ 11.54 (br s, 1H), 10.15 (br s, 1H), 9.72 (t, J 5.7 Hz, 1H), 8.08 (d, J = 8.3 Hz, 1H), 7.99 (td J = 7.7, 0.8 Hz, 2H), 7.93-7.82 (m, 4H), 7.76 (d, J = 8.7 Hz, 2H), 6.87 (d, J = 8.7 Hz, 2H), 4.85 (d, J = 5.8 Hz, 2H); |

TABLE 1-continued

Synthesis from various acids and various amines

| Compound No. | Structure | Procedure, Intermediate, amine | Rx. Yield (%) | Mass Spec. Found | Mass Spec. Calculated | 1H-NMR |
|---|---|---|---|---|---|---|
| 825-A | 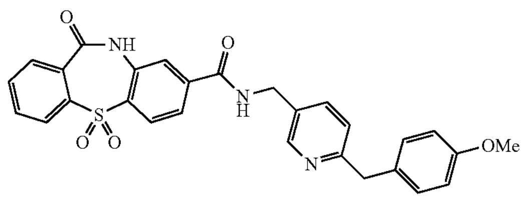 [SMILES: COc1ccc(Cc2ccc(CNC(=O)c3ccc4c(c3)NC(=O)c3ccccc3S4(=O)=O)cn2)cc1] | A[a], 30, 72 | 52 | 514.1 (M[+] + 1); | 513.14 for $C_{28}H_{23}N_3O_5S$ | 1H NMR (DMSO-d$_6$, 400 MHz): δ 11.49 (s, 1H), 9.25 (t, J = 5.8 Hz, 1H), 8.42 (d, J = 1H), 8.04 (d, J = 8.2 Hz, 1H), 8.00-7.94 (m, 2H), 7.92-7.78 (m, 4H), 7.60 (dd, J = 8.0 2.3 Hz, 1H), 7.23-7.13 (m, 3H), 6.82 (d, J = 8.7 Hz, 2H), 4.43 (br d, J = 5.6 Hz, 2H), 3.97 (s, 2H), 3.69 (s, 3H); |
| 875 | 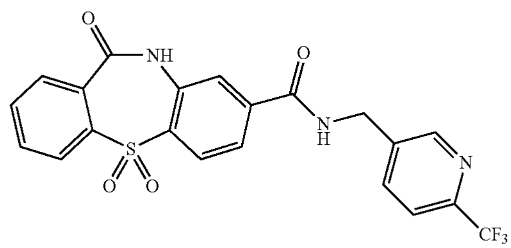 [SMILES: O=C(NCc1cnc(C(F)(F)F)nc1)c1ccc2c(c1)NC(=O)c1ccccc1S2(=O)=O] | A, 30, 55 | 89 | 462.0 (M[+] + 1); | 461.07 for C21H14F3N3O4S | 1H NMR (DMSO-d6, 400 MHz): δ 11.52 (s, 1H), 9.40 (t, J = 5.9 Hz, 1H), 8.73 (s, 1H), 8.07 (d, J = 8.2 Hz, 1H), 8.01-7.95 (m, 3H), 7.93-7.82 (m, 5H), 4.59 (d, J = 5.4 Hz, 2H); |
| 876 | 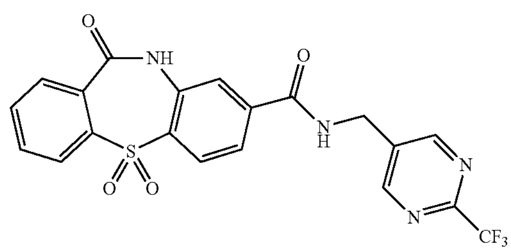 | A[b], 30, 77 | 22 | 463.0 (M[+] + 1); | 462.06 for $C_{20}H_{13}F_3N_4O_4S$ | 1H NMR (500 MHz, DMSO-d$_6$): δ 11.52 (s, 1H), 9.39 (t, J = 5.5 Hz, 1H), 9.02 (s, 2H), 8.07 (d, J = 8.1 Hz, 1H), 8.01-7.94 (m, 2H), 7.93-7.82 (m, 4H), 4.61 (d, J = 5.8 Hz, 2H); |
| 739 | 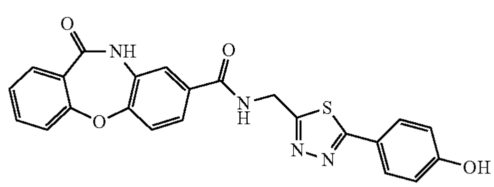 [SMILES: O=C(NCc1nnc(-c2ccc(O)cc2)s1)c1ccc2c(c1)NC(=O)c1ccccc1O2] | A, 35, 63 | 7 | 445.1 (M[+] + 1); | 444.09 for $C_{23}H_{16}N_4O_4S$ | 1H NMR (400 MHz, DMSO-d$_6$): δ 10.70 (ms 1H), 10.15 (br s, 1H), 9.46 (t, J = 5.8 Hz, 1H), 7.81-7.71 (m, 4H), 7.69-7.60 (m, 2H), 7.45 (d, J = 8.4 Hz, 1H), 7.39-7.30 (m, 2H), 6.87 (d, J = 8.7 Hz, 2H), 4.82 (d, J = 5.8 Hz, 2H) |

TABLE 1-continued

Synthesis from various acids and various amines

| Compound No. | Structure | Procedure, Intermediate, amine | Rx. Yield (%) | Mass Spec. Found | Mass Spec. Calculated | $^1$H-NMR |
|---|---|---|---|---|---|---|
| 837-A | 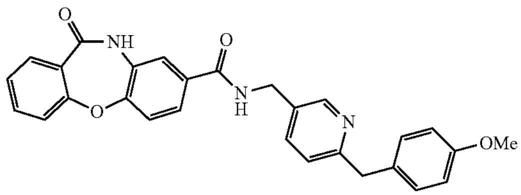 [SMILES: COc1ccc(Cc2ccc(CNC(=O)c3ccc4c(c3)NC(=O)c3ccccc3O4)cn2)cc1] | A$^a$, 35, 72 | 21 | 466.1 (M$^+$ + 1); | 465.17 for $C_{28}H_{23}N_3O_4$ | $^1$H-NMR (DMSO-d$_6$, 400 MHz): δ 10.62 (s, 1H), 9.06 (t, J = 5.6 Hz, 1H), 8.54 (br s, 1H), 7.87 (d, J = 6.4 Hz, 1H), 7.78 (d, J = 6.9 Hz, 1H), 7.68-7.60 (m, 3H), 7.42 (d, J = 8.1 Hz, 2H), 7.38-7.30 (m, 2H), 7.19 (d, J = 8.4 Hz, 2H), 6.85 (d, J = 8.4 Hz, 2H), 4.47 (d, J = 5.5 Hz, 2H), 4.08 (s, 2H), 3.70 (s, 3H); |
| 504 | 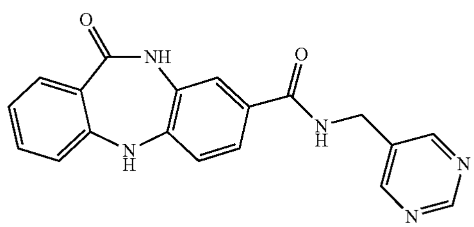 [SMILES: O=C(NCc1cncnc1)c1ccc2c(c1)NC(=O)c1ccccc1N2] | A, 40, 52 | 24% | 345.9 (M$^+$ + 1); | 345.12 for $C_{19}H_{15}N_5O_2$ | $^1$H-NMR (DMSO-d$_6$, 400 MHz): δ 9.89 (s, 1H), 9.08 (s, 1H), 8.91 (t, J = 5.7 Hz, 1H), 8.74 (s, 2H), 8.16 (s, 1H), 7.69 (dd, J = 7.8, 1.5 Hz, 1H), 7.50-7.44 (m, 2H), 7.38-7.32 (m, 1H), 7.01 (dd, J = 14.9, 7.8 Hz, 2H), 6.93-6.88 (m, 1H), 4.45 (d, J = 5.6 Hz, 2H); |
| 505 | 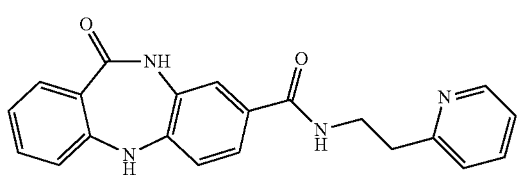 [SMILES: O=C(NCCc1ccccn1)c1ccc2c(c1)NC(=O)c1ccccc1N2] | A, 40, 56 | 51% | 358.9 (M$^+$ + 1); | 358.14 for $C_{21}H_{18}N_4O_2$ | $^1$H-NMR (DMSO-d$_6$, 400 MHz): δ 9.90 (s, 1H), 8.50 (d, J = 4.2 Hz, 1H), 8.36 (t, J = 5.4 Hz, 1H), 8.11 (s, 1H), 7.73-7.65 (m, 2H), 7.44 (s, 1H), 7.40 (dd, J = 8.2, 1.7 Hz, 1H), 7.37-7.32 (m, 1H), 7.26 (d, J = 7.7 Hz, 1H), 7.23-7.20 (1H), 6.99 (dd, J = 8.0, 4.8 Hz, 2H), 6.91 (t, J = 7.3 Hz, 1H), 3.60-3.54 (m, 2H), 2.96 (t, J = 7.3 Hz, 2H); |

TABLE 1-continued

Synthesis from various acids and various amines

| Compound No. | Structure | Procedure, Intermediate, amine | Rx. Yield (%) | Mass Spec. Found | Mass Spec. Calculated | $^1$H-NMR |
|---|---|---|---|---|---|---|
| 506 | 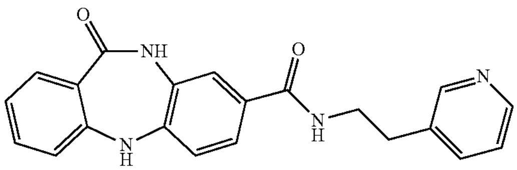 [SMILES: O=C(NCCc1cccnc1)c1ccc2c(c1)NC(=O)c1ccccc1N2] | A, 40, 54 | 43% | 358.9 ($M^+ + 1$); | 358.14 for $C_{21}H_{18}N_4O_2$ | $^1$H-NMR (DMSO-$d_6$, 400 MHz): δ 9.90 (s, 1H), 8.44 (s, 1H), 8.40 (dd, J = 4.8, 1.5 Hz, 1H), 8.36 (t, J = 5.4 Hz, 1H), 8.11 (s, 1H), 7.69 (dd, J = 7.9, 1.5 Hz, 1H), 7.64 (dt, J = 7.8, 1.8 Hz, 1H), 7.43 (s, 1H), 7.41-7.27 (m, 3H), 6.99 (dd, J = 7.9, 4.4 Hz, 2H), 6.94-6.88 (m, 1H), 3.51-3.43 (m, 2H), 2.84 (t, J = 7.1 Hz, 2H); |
| 507 | 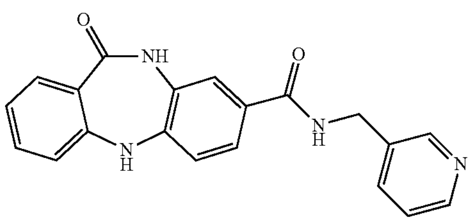 [SMILES: O=C(NCc1cccnc1)c1ccc2c(c1)NC(=O)c1ccccc1N2] | A, 40, 53 | 72% | 344.9 ($M^+ + 1$); | 344.13 for $C_{20}H_{16}N_4O_2$ | $^1$H-NMR (DMSO-$d_6$, 400 MHz): δ 9.90 (s, 1H), 8.88 (t, J = 5.7 Hz, 1H), 8.53 (s, 1H), 8.45 (d, J = 3.4 Hz, 1H), 8.15 (s, 1H), 7.69 (d, J = 7.8 Hz, 2H), 7.51-7.45 (m, 2H), 7.38-7.30 (m, 2H), 7.01 (dd, J = 13.7, 8.0 Hz, 2H), 6.91 (t, J = 7.4 Hz, 1H), 4.45 (d, J = 5.7 Hz, 2H); |
| 545 | 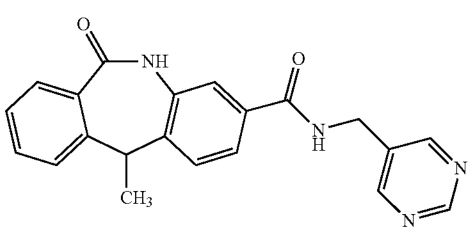 [SMILES: CC1c2ccc(C(=O)NCc3cncnc3)cc2NC(=O)c2ccccc21] | A, 51, 52 | 69% | 358.9 ($M^+ + 1$); | 358.14 for $C_{21}H_{18}N_4O_2$ | $^1$H-NMR (DMSO-$d_6$, 400 MHz): δ 10.64-10.52 (m, 1H), 9.07-9.06 (m, 1H), 9.03 (t, J = 5.4 Hz, 1H), 8.73 (d, J = 3.9 Hz, 2H), 7.77 (d, J = 8.6 Hz, 0.5 H), 7.67-7.60 (m, 2H), 7.56-7.47 (m, 1.5 H), 7.44-7.28 (m, 3H), 4.49-4.44 (m, 2H), 4.28-4.10 (m, 1H), 1.78, 1.44 (d, J = 7.3 Hz, 3 H); |

TABLE 1-continued

Synthesis from various acids and various amines

| Compound No. | Structure | Procedure, Intermediate, amine | Rx. Yield (%) | Mass Spec. Found | Mass Spec. Calculated | $^1$H-NMR |
|---|---|---|---|---|---|---|
| 547 | 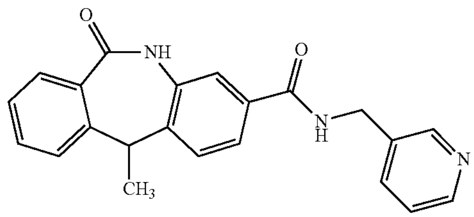 [SMILES: CC1c2ccc(C(=O)NCc3cccnc3)cc2NC(=O)c2ccccc21] | A, 51, 53 | 62% | 357.9 (M$^+$ + 1); | 357.15 for C$_{22}$H$_{19}$N$_3$O$_2$ | $^1$H-NMR (DMSO-d$_6$, 400 MHz): δ 10.65-10.50 (m, 1H), 9.00 (t, J = 4.9 Hz, 1H), 8.53-8.51 (m, 1H), 8.46-8.42 (m, 1H), 7.78 (d, J = 6.9 Hz, 0.5 H), 7.70-7.60 (m, 3H), 7.57-7.53 (m, 0.5 H), 7.52-7.47 (m, 1H), 7.43-7.29 (m, 4H), 4.46 (d, J = 5.9 Hz, 2H), 4.27-4.10 (m, 1H), 1.78, 1.44 (d, J = 7.2 Hz, 3H); |

A$^a$: DIPEA (5 equiv);
A$^b$: EDCI (2 equiv), HOBt (2 equiv);

Example 13: Synthesis of N-((6-chloropyridin-3-yl) methyl)-11-oxo-10,11-dihydrodibenzo[b,f][1,4]thiazepine-8-carboxamide 5,5-dioxide (79): A Common Intermediate

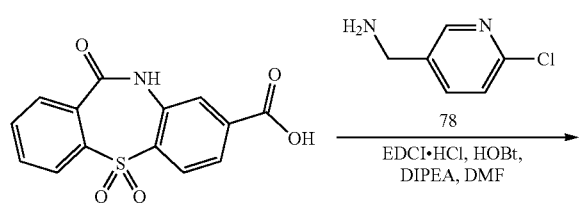

Synthesis of N-((6-chloropyridin-3-yl) methyl)-11-oxo-10,11-dihydrodibenzo[b,f][1, 4]thiazepine-8-carboxamide 5,5-dioxide (79)

To a stirring solution of compound 30 (2 g, 6.60 mmol) in DMF (40 mL) under inert atmosphere were added EDCI. HCl (1.91 g, 9.95 mmol), HOBt (1.34 g, 9.95 mmol), (6-chloropyridin-3-yl) methanamine 78 (938 mg, 6.60 mmol) and diisopropylethylamine (3.43 mL, 19.76 mmol) at 0° C.; warmed to RT and stirred for 16 h. The reaction was monitored by TLC; after completion of the reaction, the reaction mixture was poured into ice-cold water (100 mL). The solid obtained was filtered, washed with n-pentane (20 mL) and dried in vacuo to afford compound 79 (2.5 g, 89%) as white solid. TLC: 5% MeOH/CH$_2$Cl$_2$ (R$_f$: 0.3); $^1$H NMR (DMSO-d$_6$, 500 MHz): δ 11.51 (br s, 1H), 9.32 (t, J=5.6 Hz, 1H), 8.37 (s, 1H), 8.06 (d, J=8.4 Hz, 1H), 8.01-7.95 (m, 2H), 7.90 (t, J=7.4 Hz, 1H), 7.88-7.81 (m, 3H), 7.78 (dd, J=8.1, 2.0 Hz, 1H), 7.47 (d, J=8.4 Hz, 1H), 4.48 (d, J=5.8 Hz, 2H); LC-MS: 96.13%; 427.8 (M$^+$+1); (column; Ascentis Express C18, (50×3.0 mm, 2.7 μm); RT 2.12 min. 0.025% Aq. TFA+5% ACN: ACN+5% 0.025% Aq. TFA, 1.2 mL/min).

Example 14: Synthesis of N-((2-chloropyrimidin-5-yl) methyl)-11-oxo-10, 11-dihydrodibenzo[b,f][1,4] thiazepine-8-carboxamide 5,5-dioxide (84): A Common Intermediate

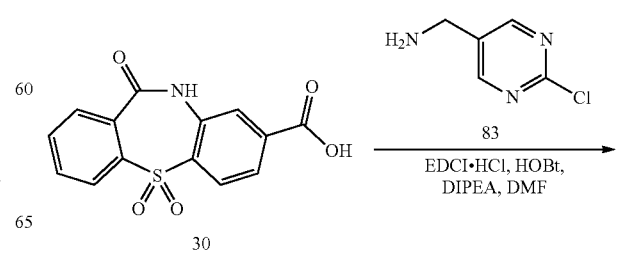

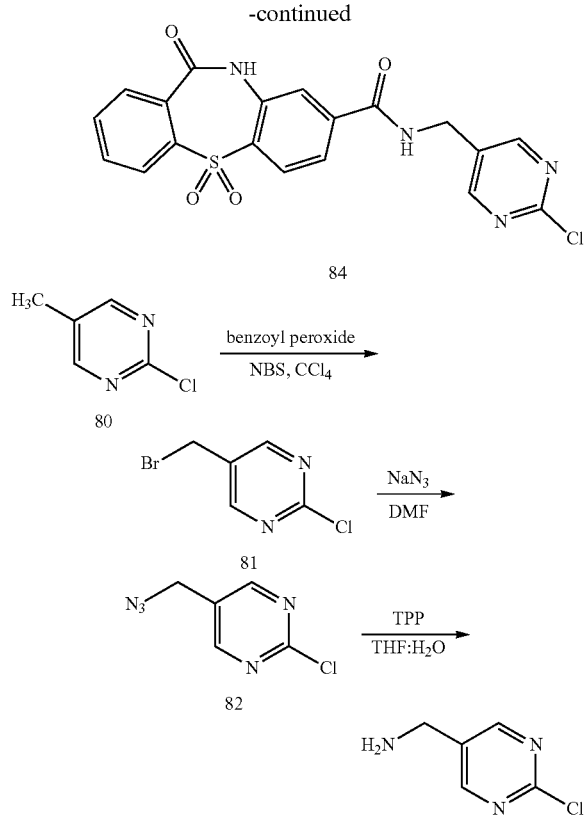

Synthesis of 5-(bromomethyl)-2-chloropyrimidine (81)

To a stirring solution of 2-chloro-5-methylpyrimidine 80 (5 g, 38.89 mmol) in CCl$_4$ (250 mL) under inert atmosphere were added N-bromosuccinimide (6.92 g, 38.89 mmol) and benzoyl peroxide (706 mg, 2.91 mmol) at RT; heated to 85° C. and stirred for 16 h. The reaction was monitored by TLC; after completion of the reaction, the reaction mixture was filtered. The filtrate was concentrated in vacuo to obtain the crude. The crude was purified through silica gel flash column chromatography using 7% EtOAc/hexanes to afford crude compound 81 (5 g, mixture of SM and product in the ratio of ~1:1) as pale yellow solid. TLC: 20% EtOAc/to hexanes (R$_f$: 0.5); LC-MS: 55.30%; 208.8 (M$^+$+1); (column; Ascentis Express C18, (50×3.0 mm, 2.7 μm); RT 1.79 min. 0.025% Aq. TFA+5% ACN: ACN+5% 0.025% Aq. TFA, 1.2 mL/min);

Synthesis of 5-(azidomethyl)-2-chloropyrimidine (82)

To a stirring solution of compound 81 (5 g, crude) in DMF (50 mL) under inert atmosphere was added sodium azide (4.7 g, 72.41 mmol) at RT and stirred for 16 h. The reaction was monitored by TLC; after completion of the reaction, the reaction mixture was diluted with water (250 mL) and extracted with EtOAc (2×100 mL). The combined organic extracts were dried over sodium sulphate, filtered and concentrated in vacuo to obtain the crude. The crude was purified through silica gel flash column chromatography using 5% EtOAc/hexanes to afford compound 82 (3.5 g, crude) as pale yellow liquid. TLC: 10% EtOAc/hexanes (R$_f$: 0.3); $^1$H NMR (DMSO-d$_6$, 400 MHz): δ 8.82 (s, 2H), 4.62 (s, 2H).

Synthesis of (2-chloropyrimidin-5-yl) methanamine (83)

To a stirring solution of compound 82 (3.5 g, crude) in THF:H$_2$O (4:1, 50 mL) was added triphenyl phosphine (5.41 g, 20.64 mmol) at 0° C.; warmed to RT and stirred for 16 h. The reaction was monitored by TLC and LC-MS; after completion of the reaction, the volatiles were removed in vacuo to obtain the crude. The crude was purified through silica gel column chromatography using 100% EtOAc to afford compound 83 (2.8 g, crude) as colorless liquid. TLC: 20% EtOAc/hexanes (R$_f$: 0.1);

Synthesis of N-((2-chloropyrimidin-5-yl) methyl)-11-oxo-10,11-dihydrodibenzo[b,f][1,4]thiazepine-8-carboxamide 5,5-dioxide (84)

To a stirring solution of compound 30 (1.23 mg, 4.07 mmol) in DMF (25 mL) under inert atmosphere were added EDCI.HCl (1.17 g, 6.10 mmol), HOBt (823 mg, 6.10 mmol), (2-chloropyrimidin-5-yl) methanamine 83 (700 mg, crude) and diisopropylethylamine (2.20 mL, 12.21 mmol) at 0° C.; warmed to RT and stirred for 16 h. The reaction was monitored by TLC; after completion of the reaction, the reaction mixture was diluted with water (125 mL) and extracted with EtOAc (2×75 mL). The combined organic extracts were dried over sodium sulfate, filtered and concentrated in vacuo to obtain the crude. The crude was purified through silica gel column chromatography using 1-3% MeOH/CH$_2$Cl$_2$ to afford compound 84 (1 g, 57%) as an off-white solid. TLC: 5% MeOH/CH$_2$Cl$_2$ (R$_f$: 0.4); $^1$H NMR (DMSO-d$_6$, 500 MHz): δ 11.51 (br s, 1H), 9.37-9.23 (m, 1H), 8.75-8.67 (m, 1H), 8.07-8.02 (m, 1H), 8.01-7.95 (m, 2H), 7.93-7.73 (m, 4H), 7.66-7.50 (m, 1H), 4.50 (d, J=5.8 Hz, 2H); LC-MS: 96.84%; 448.0 (M$^+$+1); (column; Ascentis Express C18, (50×3.0 mm, 2.7 μm); RT 2.19 min. 0.025% Aq. TFA+5% ACN: ACN+5% 0.025% Aq. TFA, 1.2 mL/min).

Example 15: Commercially Available Boronic Acids for Cross Coupling Reaction The following intermediates were obtained from commercial sources.

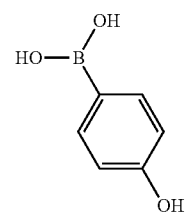

61

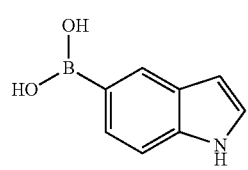

85

-continued

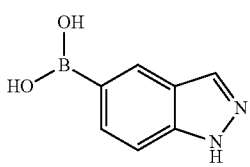
86

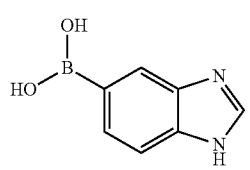
87

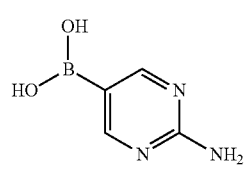
88

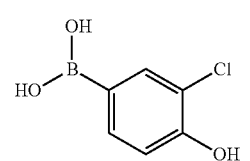
89

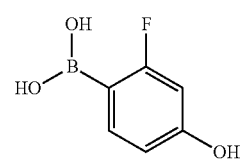
90

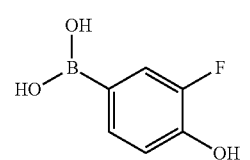
91

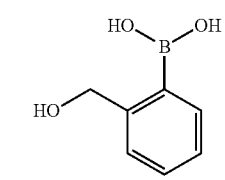
92

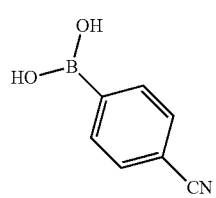
93

Example 16: Preparation of Boronic Acid or their Derivatives for Cross Coupling Reaction Synthesis of 3-chloro-4-(4, 4, 5, 5-tetramethyl-1, 3, 2-dioxaborolan-2-yl) phenol (95)

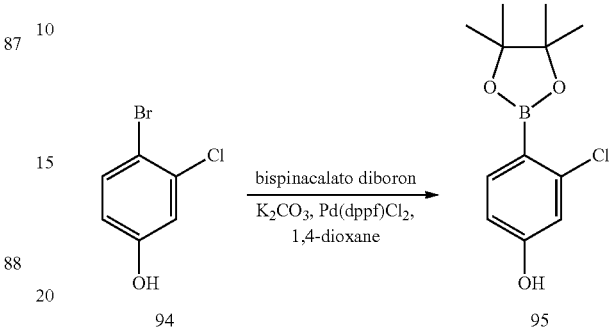

Synthesis of 3-chloro-4-(4, 4, 5, 5-tetramethyl-1, 3, 2-dioxaborolan-2-yl) phenol (95)

To a stirring solution of 4-bromo-3-chlorophenol 94 (500 mg, 2.41 mmol) in 1, 4-dioxane (30 mL) under inert atmosphere were added bis pinacolato diboron (1.20 g, 4.82 mmol), potassium carbonate (997 mg, 7.23 mmol) in a sealed tube at RT and stirred under argon atmosphere for 15 min, added Pd(dppf)Cl$_2$ (185 mg, 0.24 mmol) and heated to 90° C. and stirred for 12 h. The reaction was monitored by TLC; after completion of the reaction, the reaction mixture was filtered through celite, washed with EtOAc (2×50 mL). The filtrate was concentrated in vacuo to obtain the crude. The crude was purified through silica gel column chromatography using 10% EtOAc/hexanes to afford compound 95 (310 mg, 51%). TLC: 20% EtOAc/hexanes (R$_f$: 0.7); $^1$H NMR (DMSO-d$_6$, 400 MHz): δ 10.22 (s, 1H), 7.49 (d, J=8.3 Hz, 1H), 6.78 (d, J=2.2 Hz, 1H), 6.71 (dd, J=2.2, 8.3, 2.2 Hz, 1H), 1.27 (s, 12H); LC-MS: 89.28%; 253.1 (M-1)$^+$; (column; X Select CSH C-18, (50×3.0 mm, 2.5 μm); RT 1.68 min. 2.5 mM Aq. NH4OOCH+5% ACN: ACN+5% 2.5 mM Aq.NH$_4$OOCH, 0.8 mL/min).

Synthesis of 2, 6-difluoro-4-(4, 4, 5, 5-tetramethyl-1, 3, 2-dioxaborolan-2-yl) phenol (97)

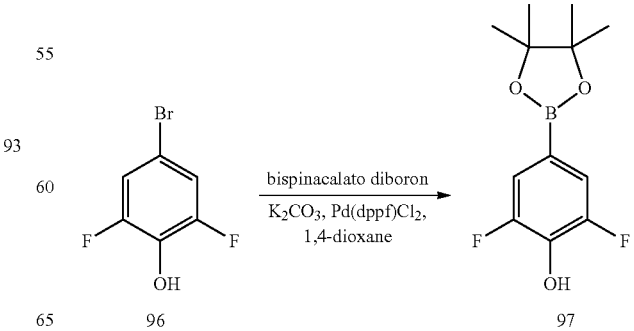

Synthesis of 2, 6-difluoro-4-(4, 4, 5, 5-tetramethyl-1, 3, 2-dioxaborolan-2-yl) phenol (97)

To a stirring solution of 4-bromo-2, 6-difluorophenol 96 (1 g, 4.80 mmol) in 1, 4-dioxane (25 mL) under inert atmosphere were added bis pinacolato diboron (1.83 g, 7.21 mmol), potassium carbonate (1.98 g, 14.40 mmol) and purged under argon atmosphere for 10 min. To this was added Pd(dppf)Cl$_2$ (350 mg, 0.48 mmol) and the reaction mixture was heated to 100° C. for 4 h. The reaction was monitored by TLC; after completion of the reaction, the reaction mixture was filtered through celite, eluted with CH$_2$Cl$_2$ (75 mL). The filtrate was concentrated in vacuo to obtain the crude. The crude was purified through silica gel column chromatography using 2-5% EtOAc/hexanes to compound 97 (620 mg, 50%) TLC: 10% EtOAc/hexanes (R$_f$: 0.5).

Example 17: Compound Preparation

The common intermediates 79 and 84 were converted to final products through cross coupling reaction using commercially available cross coupling reagents or prepared cross coupling reagents employing typical procedure B or C and the results are captured in the Table 2:

Typical Procedure B:

To a stirring solution of N-((2-chloropyrimidin-5-yl)methyl)-11-oxo-10,11-dihydrodibenzo[b,f][1,4]thiazepine-8-carboxamide 5,5-dioxide 84 (150 mg, 0.35 mmol) in 1, 2 dimethoxy ethane: H$_2$O (4:1, 8 mL) were added sodium carbonate (124 mg, 1.17 mmol), (1H-indazol-5-yl)boronic acid 86 (68 mg, 0.42 mmol) and purged under argon atmosphere for 20 min. To this was added Pd(dppf)Cl$_2$ (45 mg, 0.039 mmol) at RT; heated to 100-110° C. and stirred for 16 h. The reaction was monitored by TLC; after completion the volatiles were removed in vacuo to obtain the crude. The crude was either directly dried in vacuo or triturated or purified through silica gel column chromatography to afford the desired compound.

Typical Procedure C:

To a stirring solution of N-((6-chloropyridin-3-yl)methyl)-11-oxo-10, 11-dihydrodibenzo[b,f][1,4]thiazepine-8-carboxamide 5,5-dioxide 79 (150 mg, 0.35 mmol) in 1, 4 dioxane: H$_2$O (3:1, 10 mL) were added cesium carbonate (341 mg, 1.05 mmol), 4-hydroxy phenyl boronic acid 61 (97 mg, 0.70 mmol) and purged under argon atmosphere for 15 min. To this was added Pd(dppf)Cl$_2$ (26 mg, 0.035 mmol) at RT; heated to 100° C. and stirred for 16 h. The reaction was monitored by TLC; after completion the volatiles were removed in vacuo to obtain the crude. The crude was either directly dried in vacuo or triturated or purified through silica gel column chromatography to afford the desired compound.

TABLE 2

Synthesis using cross coupling reaction:

| Compound No. | Structure | Procedure, Intermediate, coupling reagents | Rx. Yield | Mass Spec. Found | Mass Spec. Calculated | $^1$H-NMR |
|---|---|---|---|---|---|---|
| 778 | 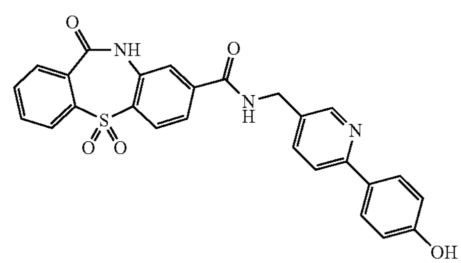 [SMILES: O=C(NCc1ccc(-c2ccc(O)cc2)nc1)c1ccc2c(c1)NC(=O)c1ccccc1S2(=O)=O] | C$^a$, 79, 61 | 71 | 485.9 (M$^+$ + 1); | 485.10 for C$_{26}$H$_{19}$N$_3$O$_5$S | $^1$H NMR (DMSO-d$_6$, 400 MHz): δ 11.51 (br s, 1H), 9.69 (s, 1H), 9.32 (t, J = 5.6 Hz, 1H), 8.53 (s, 1H), 8.06 (d, J = 8.4 Hz, 1H), 8.00-7.96 (m, 2H), 7.93-7.82 (m, 6H), 7.78 (d, J = 7.8 Hz, 1H), 7.74-7.68 (m, 1H), 6.84 (d, J = 8.7 Hz, 2H), 4.49 (d, J = 5.2 Hz, 2H); |
| 779 | 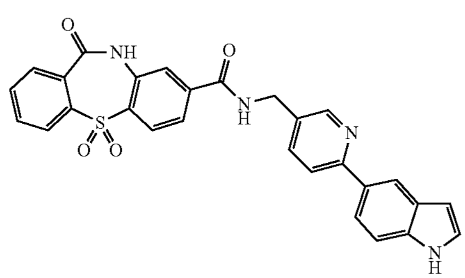 [SMILES: O=C(NCc1ccc(-c2ccc3[nH]ccc3c2)nc1)c1ccc2c(c1)NC(=O)c1ccccc1S2(=O)=O] | C$^a$, 79, 85 | 45 | 509.0 (M$^+$ + 1); | 508.12 for C$_{28}$H$_{20}$N$_4$O$_4$S | $^1$H NMR (DMSO-d$_6$, 400 MHz): δ 11.52 (s, 1H), 11.18 (br s, 1H), 9.33 (t, J = 5.5 Hz, 1H), 8.57 (s, 1H), 8.25 (s, 1H), 8.06 (d, J = 8.0 Hz, 1H), 7.98 (t, J = 8.5 Hz, 2H), 7.94-7.80 (m, 6H), 7.74 (dd, J = 8.2, 1.4 Hz, 1H), 7.45 (d, J = 8.5 Hz, 1H), 7.37 (br s, 1H), 6.51 (br s, 1H), 4.51 (d, J = 4.9 Hz, 2H); |

TABLE 2-continued

Synthesis using cross coupling reaction:

| Compound No. | Structure | Procedure, Intermediate, coupling reagents | Rx. Yield | Mass Spec. Found | Mass Spec. Calculated | ¹H-NMR |
|---|---|---|---|---|---|---|
| 780 | 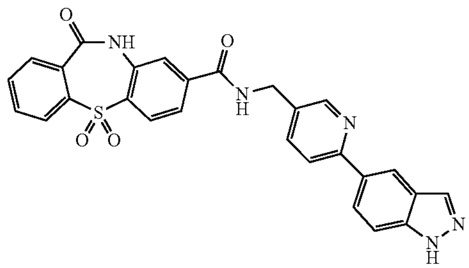 [SMILES: O=C(NCc1ccc(-c2ccc3[nH]ncc3c2)nc1)c1ccc2c(c1)NC(=O)c1ccccc1S2(=O)=O] | C$^a$, 79, 86 | 48 | 510.0 (M$^+$ + 1) | 509.12 for C$_{27}$H$_{19}$N$_5$O$_4$S | ¹H NMR (DMSO-d$_6$, 500 MHz): δ 13.14 (br s, 1H), 11.50 (br s, 1H), 9.34 (t, J = 5.5 Hz, 1H), 8.61 (s, 1H), 8.45 (s, 1H), 8.15 (s, 1H), 8.11 (d, J = 9.0 Hz, 1H), 8.06 (d, J = 8.1 Hz, 1H), 8.02-7.94 (m, 3H), 7.92-7.83 (m, 4H), 7.78 (dd, J = 8.1, 1.7 Hz, 1H), 7.61 (d, J = 8.7 Hz, 1H), 4.53 (d, J = 5.5 Hz, 2H); |
| 781 | 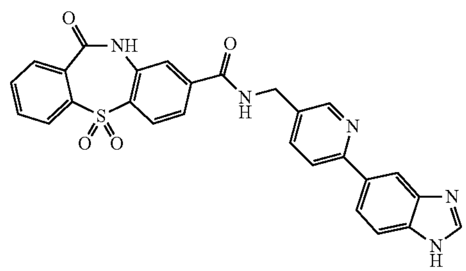 [SMILES: O=C(NCc1ccc(-c2ccc3[nH]cnc3c2)nc1)c1ccc2c(c1)NC(=O)c1ccccc1S2(=O)=O] | C$^a$, 79, 87 | 16 | 510.0 (M$^+$ + 1) | 509.12 for C$_{27}$H$_{19}$N$_5$O$_4$S | ¹H NMR (500 MHz, DMSO-d$_6$) δ 12.54 (d, J = 14.8 Hz, 1H), 11.51 (br s, 1H), 9.34 (t, J = 4.8 Hz, 1H), 8.61 (br s, 1H), 8.33-8.20 (m, 2H), 8.06 (d, J = 8.2 Hz, 1H), 8.02-7.74 (m, 8H), 7.71 (d, J = 8.5 Hz, 1H), 7.59 (d, J = 8.4 Hz, 1H), 4.53 (d, J = 5.4 Hz, 2H); |
| 782 | 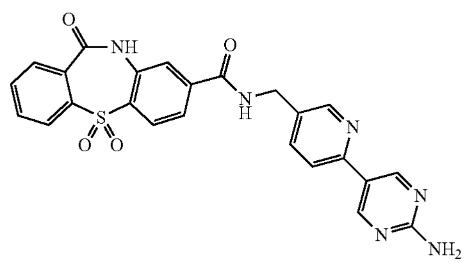 [SMILES: Nc1ncc(-c2ccc(CNC(=O)c3ccc4c(c3)NC(=O)c3ccccc3S4(=O)=O)cn2)cn1] | B$^a$, 79, 88 | 26 | 487.0 (M$^+$ + 1) | 486.11 for C$_{24}$H$_{18}$N$_6$O$_4$S | ¹H NMR (DMSO-d$_6$, 500 MHz): δ 11.51 (s, 1H), 9.32 (t, J = 5.6 Hz, 1H), 8.89 (s, 2H), 8.55 (s, 1H), 8.06 (d, J = 8.4 Hz, 1H), 8.01-7.95 (m, 2H), 7.93-7.80 (m, 5H), 7.74 (dd, J = 8.2, 1.6 Hz, 1H), 6.94 (s, 2H), 4.49 (d, J = 5.5 Hz, 2H); |
| 783 | 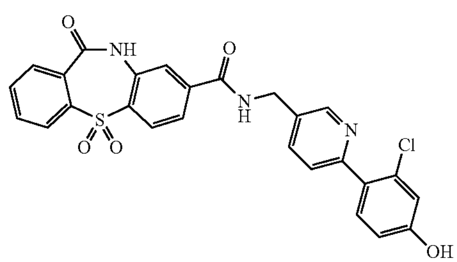 | C$^a$, 79, 95 | 16 | 520.3 (M$^+$ + 1) | 519.07 for C$_{26}$H$_{18}$ClN$_3$O$_5$S | ¹H NMR (DMSO-d$_6$, 400 MHz): δ 11.52 (s, 1H), 10.12 (br s, 1H), 9.36 (t, J = 5.8 Hz, 1H), 8.60 (d, J = 1.6 Hz, 1H), 8.06 (d, J = 8.3 Hz, 1H), 8.01-7.96 (m, 2H), 7.93-7.83 (m, 4H), 7.79 (dd, J = 8.0, 2.1 Hz, 1H), 7.60 (d, J = 8.0 Hz, 1H), 7.41 (d, J = 8.4 Hz, 1H), 6.91 (d, J = 2.5 Hz, 1H), 6.84 (dd, J = 8.5, 2.4 Hz, 1H), 4.54 (d, J = 5.8 Hz, 2H); |
| 784 | 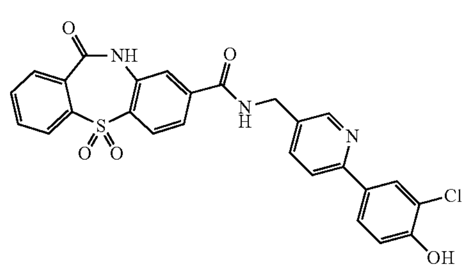 [SMILES: O=C(NCc1ccc(-c2ccc(O)c(Cl)c2)nc1)c1ccc2c(c1)NC(=O)c1ccccc1S2(=O)=O] | B, 79, 89 | 25 | 520.0 (M$^+$ + 1) | 519.07 for C$_{26}$H$_{18}$ClN$_3$O$_5$S | ¹H-NMR (DMSO-d$_6$, 400 MHz): δ 11.51 (s, 1H), 10.47 (s, 1H), 9.32 (t, J = 5.7 Hz, 1H), 8.55 (s, 1H), 8.08-8.03 (m, 2H), 8.01-7.95 (m, 2H), 7.93-7.81 (m, 6H), 7.74 (dd, J = 8.3, 2.3 Hz, 1H), 7.05 (d, J = 8.5 Hz, 1H), 4.50 (d, J = 5.6 Hz, 2H); |

TABLE 2-continued

Synthesis using cross coupling reaction:

| Compound No. | Structure | Procedure, Intermediate, coupling reagents | Rx. Yield | Mass Spec. Found | Mass Spec. Calculated | ¹H-NMR |
|---|---|---|---|---|---|---|
| 785 | 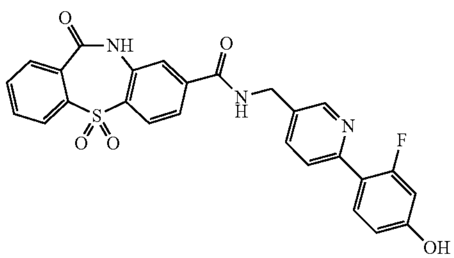 | B, 79, 90 | 26 | 504.0 (M⁺ + 1); | 503.10 for $C_{26}H_{18}FN_3O_5S$ | ¹H NMR (DMSO-d₆, 400 MHz): δ 11.51 (s, 1H), 10.17 (s, 1H), 9.34 (t, J = 5.7 Hz, 1H), 8.60 (s, 1H), 8.06 (d, J = 8.2 Hz, 1H), 8.01-7.95 (m, 2H), 7.93-7.82 (m, 4H), 7.81-7.73 (m, 2H), 7.64 (d, J = 6.9 Hz, 1H), 6.73 (dd, J = 8.5, 2.1 Hz, 1H), 6.65 (dd, J = 13.4, 2.1 Hz, 1H), 4.51 (d, J = 5.6 Hz, 2H); |
| 786 | 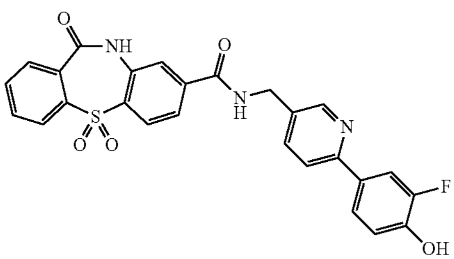 [SMILES: O=C(NCc1ccc(-c2ccc(O)c(F)c2)nc1)c1ccc2c(c1)NC(=O)c1ccccc1S2(=O)=O] | B, 79, 91 | 31 | 504.0 (M⁺ + 1); | 503.10 for $C_{26}H_{18}FN_3O_5S$ | ¹H NMR (DMSO-d₆, 400 MHz): δ 11.51 (s, 1H), 10.15 (s, 1H), 7.98 (s, 1H), 8.56-8.54 (m, 1H), 8.06 (d, J = 8.2 Hz, 1H), 7.98 (dd, J = 7.2, 1.8 Hz, 2H), 7.93-7.81 (m, 6H), 7.76-7.71 (m, 2H), 7.02 (t, J = 8.8 Hz, 1H), 4.50 (d, J = 5.8 Hz, 2H); |
| 787 | 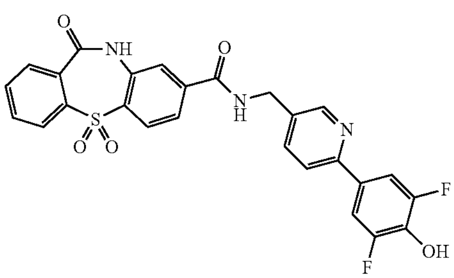 [SMILES: O=C(NCc1ccc(-c2cc(F)c(O)c(F)c2)nc1)c1ccc2c(c1)NC(=O)c1ccccc1S2(=O)=O] | B$^d$, 79, 97 | 6 | 522.0 (M⁺ + 1); | 521.09 for $C_{26}H_{17}F_2N_3O_5S$ | ¹H NMR (400 MHz, DMSO-d₆): δ 11.51 (s, 1H), 10.50 (s, 1H), 9.33 (t, J = 5.8 Hz, 1H), 8.57 (s, 1H), 8.06 (d, J = 8.2 Hz, 1H), 8.01-7.96 (m, 2H), 7.94-7.81 (m, 5H), 7.79-7.74 (m, 3H), 4.51 (d, J = 5.5 Hz, 2H); |
| 843 | 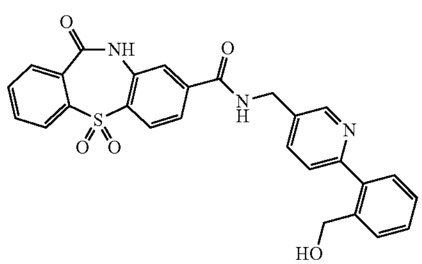 [SMILES: O=C(NCc1ccc(-c2ccccc2CO)nc1)c1ccc2c(c1)NC(=O)c1ccccc1S2(=O)=O] | B$^f$, 79, 92 | 45 | 500.0 (M⁺ + 1); | 499.12 for $C_{27}H_{21}N_3O_5S$ | ¹H NMR (400 MHz, DMSO-d₆): δ 11.52 (s, 1H), 9.37 (t, J = 5.8 Hz, 1H), 8.61 (s, 1H), 8.07 (d, J = 8.2 Hz, 1H), 8.02-7.95 (m, 2H), 7.93-7.80 (m, 5H), 7.59 (dd, J = 10.1, 8.1 Hz, 2H), 7.48-7.33 (m, 3H), 5.32 (t, J = 5.9 Hz, 1H), 4.56 (d, J = 5.8 Hz, 2H), 4.49 (d, J = 5.9 Hz, 2H); |
| 867 | 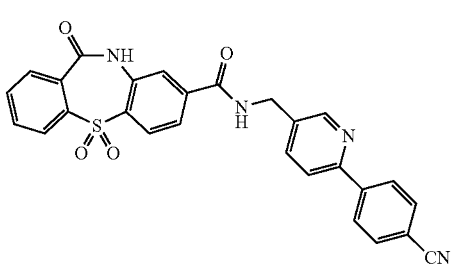 [SMILES: N#Cc1ccc(-c2ccc(CNC(=O)c3ccc4c(c3)NC(=O)c3ccccc3S4(=O)=O)cn2)cc1] | B$^c$, 79, 93 | 43 | 495.1 (M⁺ + 1); | 494.10 for $C_{27}H_{18}N_4O_4S$ | ¹H NMR (DMSO-d₆, 400 MHz): δ 11.52 (s, 1H), 9.37 (t, J = 5.5 Hz, 1H), 8.68 (s, 1H), 8.26 (d, J = 8.3 Hz, 2H), 8.06 (dd, J = 8.0, 3.4 Hz, 2H), 8.01-7.83 (m, 9H), 4.55 (d, J = 5.5 Hz, 2H); |

TABLE 2-continued

Synthesis using cross coupling reaction:

| Compound No. | Structure | Procedure, Intermediate, coupling reagents | Rx. Yield | Mass Spec. Found | Mass Spec. Calculated | ¹H-NMR |
|---|---|---|---|---|---|---|
| 788 | 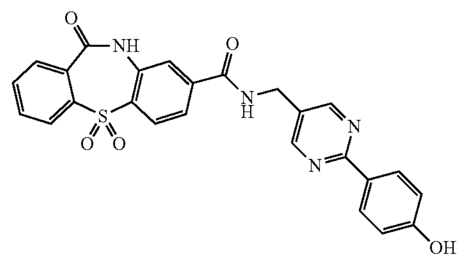 | B′, 84, 61 | 18 | 487.1 (M⁺ + 1); | 486.10 for $C_{25}H_{18}N_4O_5S$ | ¹H NMR (DMSO-d₆, 500 MHz): δ 11.49 (s, 1H), 9.91 (s, 1H), 9.30 (t, J = 5.7 Hz, 1H), 8.73 (s, 2H), 8.19 (d, J = 8.7 Hz, 2H), 8.04 (d, J = 8.4 Hz, 1H), 7.96 (dd, J = 11.1. 7.7 Hz, 2H), 7.89 (t, J = 7.5 Hz, 1H), 7.86-7.80 (m, 3H), 6.84 (d, J = 8.7 Hz, 2H), 4.47 (d, J = 5.7 Hz, 2H); |
| 789 | 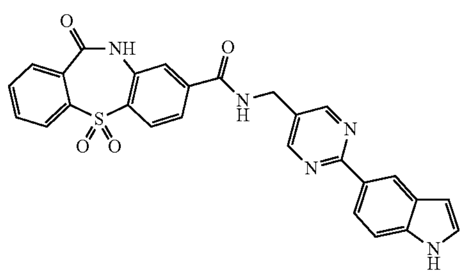 [SMILES: O=C(NCc1cnc(-c2ccc3[nH]ccc3c2)nc1)c1ccc2c(c1)NC(=O)c1ccccc1S2(=O)=O] | B′, 84, 85 | 16 | 510.1 (M⁺ + 1); | 509.12 for $C_{27}H_{19}N_5O_4S$ | ¹H NMR (DMSO-d₆, 500 MHz): δ 11.51 (br s, 1H), 11.28 (br s, 1H), 9.33 (t, J = 5.6 Hz, 1H), 8.78 (s, 2H), 8.64 (s, 1H), 8.17 (dd, J = 8.7, 1.2 Hz, 1H), 8.06 (d, J = 8.4 Hz, 1H), 7.98 (dd, J = 11.4, 7.7 Hz, 2H), 7.92-7.82 (m, 5H), 7.47 (d, J = 8.4 Hz, 1H), 7.40 (t, J = 2.6 Hz, 1H), 6.55 (br s, 1H), 4.50 (d, J = 5.5 Hz, 2H); |
| 790 | 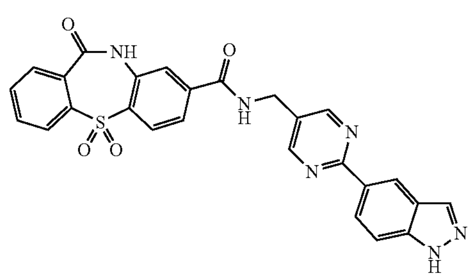 [SMILES: O=C(NCc1cnc(-c2ccc3[nH]ncc3c2)nc1)c1ccc2c(c1)NC(=O)c1ccccc1S2(=O)=O] | B′, 84, 86 | 11 | 511.1 (M⁺ + 1); | 510.11 for $C_{26}H_{18}N_6O_4S$ | ¹H NMR (DMSO-d₆, 400 MHz): δ 13.24 (br d, J = 2.1 Hz, 1H), 9.37 (t, J = 5.6 Hz, 1H), 8.83 (s, 2H), 8.40 (dd, J = 8.9, 1.4 Hz, 1H), 8.21 (s, 1H), 8.06 (d, J = 8.2 Hz, 1H), 8.01-7.95 (m, 2H), 7.93-7.82 (m, 4H), 7.63 (d, J = 8.9 Hz, 1H), 7.30 (br s, 2H), 4.52 (d, J = 5.5 Hz, 2H); |
| 791 | 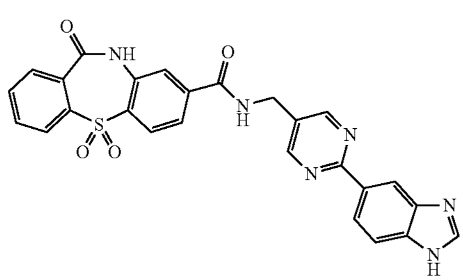 [SMILES: O=C(NCc1cnc(-c2ccc3[nH]cnc3c2)nc1)c1ccc2c(c1)NC(=O)c1ccccc1S2(=O)=O] | C, 84, 87 | 19 | 511.1 (M⁺ + 1); | 510.11 for $C_{26}H_{18}N_6O_4S$ | ¹H NMR (DMSO-d₆, 500 MHz, Varience temperature, RT): δ 12.70-12.59 (m, 1H), 11.52 (s, 1H), 9.37-9.35 (m, 1H), 8.83 (s, 2H), 8.68-8.54 (m, 1H), 8.35-7.57 (m, 10H), 4.52 (d, J = 4.0 Hz, 2H); |

TABLE 2-continued

Synthesis using cross coupling reaction:

| Compound No. | Structure | Procedure, Intermediate, coupling reagents | Rx. Yield | Mass Spec. Found | Mass Spec. Calculated | $^1$H-NMR |
|---|---|---|---|---|---|---|
| 792 | 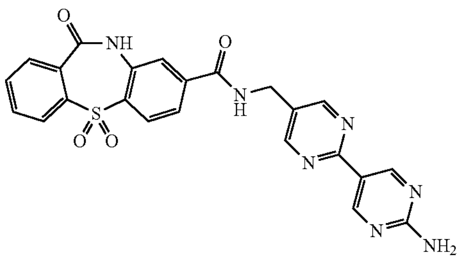 | B, 84, 88 | 7 | 488.2 (M$^+$ + 1) | 487.11 for C$_{23}$H$_{17}$N$_7$O$_4$S | $^1$H NMR (DMSO-d$_6$, 400 MHz): δ 11.51 (s, 1H), 9.35-9.30 (m, 1H), 9.08 (s, 2H), 8.76 (s, 2H), 8.06 (d, J = 8.2 Hz, 1H), 8.01-7.95 (m, 2H), 7.94-7.80 (m, 4H), 7.20 (s, 2H), 4.49 (d, J = 5.1 Hz, 2H); |
| 793 | 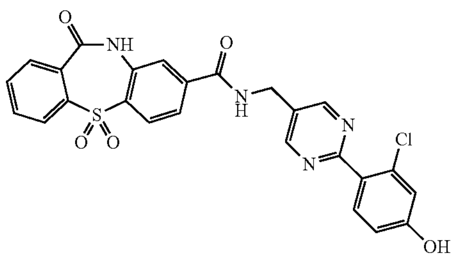 [SMILES: O=C(NCc1cnc(-c2ccc(O)cc2Cl)nc1)c1ccc2c(c1)NC(=O)c1ccccc1S2(=O)=O] | B$^f$, 84, 95 | 11 | 521.0 (M$^+$ + 1) | 520.06 for C$_{25}$H$_{17}$ClN$_4$O$_5$S | $^1$H NMR (DMSO-d$_6$, 500 MHz): δ 11.51 (s, 1H), 10.23 (s, 1H), 9.36 (t, J = 5.6 Hz, 1H), 8.83 (s, 2H), 8.06 (d, J = 8.2 Hz, 1H), 8.01-7.95 (m, 2H), 7.93-7.83 (m, 4H), 7.62 (d, 7 = 8.5 Hz, 1H), 6.91 (d, J = 2.4 Hz, 1H), 6.84 (dd, J = 8.5, 2.4 Hz, 1H), 4.54 (d, J = 5.5 Hz, 2H); |
| 794 | 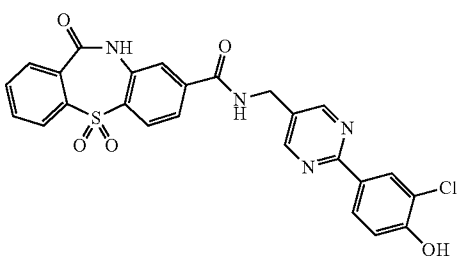 [SMILES: O=C(NCc1cnc(-c2ccc(O)c(Cl)c2)nc1)c1ccc2c(c1)NC(=O)c1ccccc1S2(=O)=O] | B$^b$, 84, 89 | 11 | 521.0 (M$^+$ + 1) | 520.06 for C$_{25}$H$_{17}$ClN$_4$O$_5$S | $^1$H NMR (DMSO-d$_6$, 400 MHz): δ 11.52 (br s, 1H), 10.76 (br s, 1H), 9.34 (t, J = 5.5 Hz, 1H), 8.79 (s, 2H), 8.29 (d, J = 2.0 Hz, 1H), 8.16 (dd, J = 8.6, 2.1 Hz, 1H), 8.06 (d, J = 8.2 Hz, 1H), 8.02-7.96 (m, 2H), 7.94-7.79 (m, 4H), 7.09 (d, J = 8.7 Hz, 1H), 4.50 (d, J = 5.5 Hz, 2H); |
| 795 | 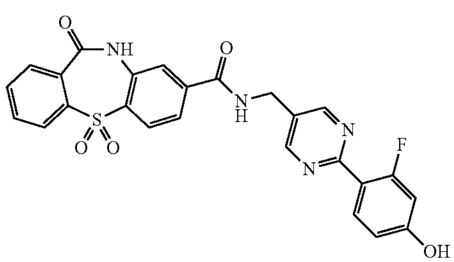 [SMILES: O=C(NCc1cnc(-c2ccc(O)cc2F)nc1)c1ccc2c(c1)NC(=O)c1ccccc1S2(=O)=O] | B, 84, 90 | 10 | 505.1 (M$^+$ + 1) | 504.09 for C$_{25}$H$_{17}$FN$_4$O$_5$S | $^1$H NMR (DMSO-d$_6$, 400 MHz): δ 11.51 (s, 1H), 10.34 (s, 1H), 9.34 (t, J = 5.0 Hz, 1H), 8.80 (s, 2H), 8.06 (br d, J = 8.2 Hz, 1H), 7.98 (t, J = 8.0 Hz, 2H), 7.94-7.81 (m, 5H), 6.68 (dd, J = 13.3, 9.2 Hz, 2H), 4.51 (d, J = 4.9 Hz, 2H); |
| 796 | 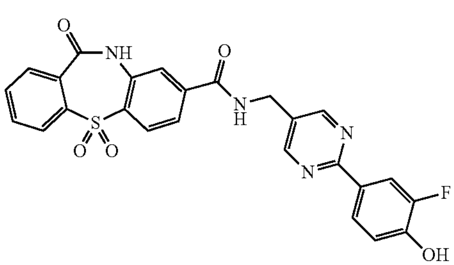 [SMILES: O=C(NCc1cnc(-c2ccc(O)c(F)c2)nc1)c1ccc2c(c1)NC(=O)c1ccccc1S2(=O)=O] | B$^e$, 84, 91 | 17 | 505.1 (M$^+$ + 1) | 504.09 for C$_{25}$H$_{17}$FN$_4$O$_5$S | $^1$H NMR (DMSO-d$_6$, 400 MHz): δ 11.51 (s, 1H), 10.42 (s, 1H), 9.33 (t, J = 5.5 Hz, 1H), 8.78 (s, 2H), 8.08-7.95 (m, 5H), 7.94-7.80 (m, 4H), 7.06 (t, J = 8.8 Hz, 1H), 4.50 (d, J = 5.3 Hz, 2H); |

TABLE 2-continued

Synthesis using cross coupling reaction:

| Compound No. | Structure | Procedure, Intermediate, coupling reagents | Rx. Yield | Mass Spec. Found | Mass Spec. Calculated | $^1$H-NMR |
|---|---|---|---|---|---|---|
| 844 | 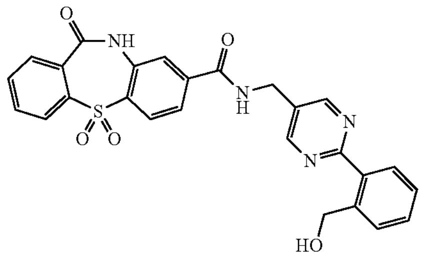 [SMILES: O=C(NCc1cnc(-c2ccccc2CO)nc1)c1ccc2c(c1)NC(=O)c1ccccc1S2(=O)=O] | $B^e$, 84, 92 | 27 | 501.1 ($M^+ + 1$); | 500.12 for $C_{26}H_{20}N_4O_5S$ | $^1$H NMR (DMSO-$d_6$, 400 MHz): δ 11.52 (s, 1H), 9.37 (t, J = 5.6 Hz, 1H), 8.88 (s, 2H), 8.07 (d, J = 8.2 Hz, 1H), 8.01-7.95 (m, 2H), 7.94-7.82 (m, 5H), 7.66 (d, J = 7.4 Hz, 1H), 7.49 (td, J = 7.5, 1.3 Hz, 1H), 7.39 (td, J = 7.5, 0.8 Hz, 1H), 5.19 (t, J = 6.0 Hz, 1H), 4.75 (d, J = 5.9 Hz, 2H), 4.56 (br d, J = 5.5 Hz, 2H); |
| 871 | 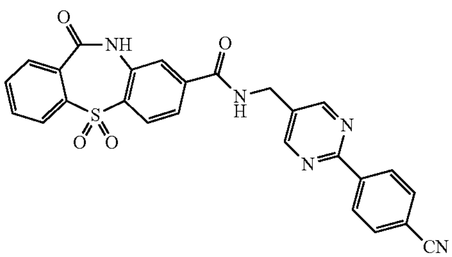 [SMILES: N#Cc1ccc(-c2ncc(CNC(=O)c3ccc4c(c3)NC(=O)c3ccccc3S4(=O)=O)cn2)cc1] | $B^f$, 84, 93 | 29 | 496.1 ($M^+ + 1$); | 495.10 for $C_{26}H_{17}N_5O_4S$ | $^1$H NMR (DMSO-$d_6$, 400 MHz): δ 11.52 (s, 1H), 9.38 (t, J = 5.6 Hz, 1H), 8.92 (s, 2H), 8.51 (d, J = 8.7 Hz, 2H), 8.06 (d, J = 8.2 Hz, 1H), 8.01-7.95 (m, 4H), 7.93-7.82 (m, 4H), 4.56 (d, J = 5.6 Hz, 2H); |

$B^a$: Pd(PPh$_3$)$_4$ (0.1 equiv), reaction temp 90-100° C.;
$B^b$: Pd(PPh$_3$)$_4$ (0.1 equiv), reaction performed in a sealed tube;
$B^c$: reaction performed at 120° C.;
$B^d$: boronate ester (2 equiv);
$B^e$: Reaction performed in a sealed tube;
$B^f$: DME: H$_2$O (3:1), Na$_2$CO$_3$ (3 equiv), boronate ester (1.2 equiv), reaction performed in sealed tube, reaction temp 120° C., 16 h.
$C^a$: boronic acid/ester (2.0 equiv), reaction time 16 h at 110° C., sealed tube.

Example 18: Synthesis of 868

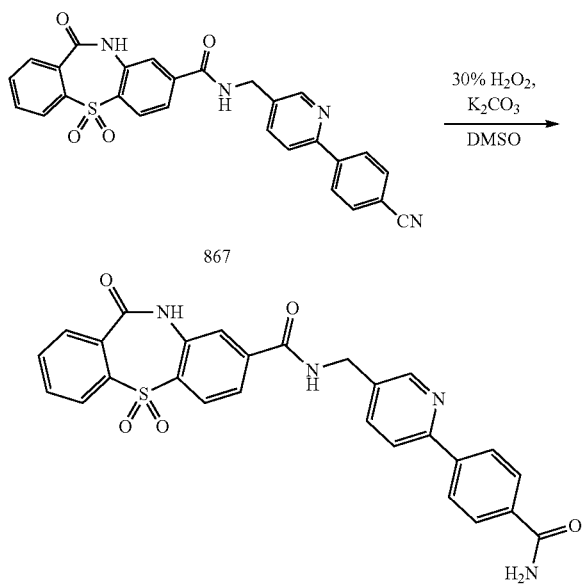

Synthesis N-((6-(4-carbamoylphenyl) pyridin-3-yl)methyl)-11-oxo-10,11-dihydrodibenzo[b,f][1,4]thiazepine-8-carboxamide 5,5-dioxide (868)

To a stirring solution of 867 (100 mg, 0.20 mmol) in DMSO (10 mL) under inert atmosphere were added potassium carbonate (139 mg, 1.00 mmol) and 30% aqueous H$_2$O$_2$ (0.23 mL, 2.00 mmol) at 0° C.; warmed to RT and stirred for 2 h. The reaction was monitored by TLC; after completion of the reaction, the reaction mixture poured into ice-cold water (50 mL) and extracted with EtOAc (3×150 mL) and dried in vacuo to obtain the crude. The crude was purified through silica gel column chromatography using 5% MeOH/CH$_2$Cl$_2$ to afford 868 (35 mg, 34%) as white solid. TLC: 10% MeOH/CH$_2$Cl$_2$ (R$_f$: 0.4). $^1$H-NMR (DMSO-$d_6$, 400 MHz): δ 11.53 (s, 1H), 9.37 (t, J=5.8 Hz, 1H), 8.65 (s, 1H), 8.13 (d, J=8.7 Hz, 2H), 8.09-7.95 (m, 7H), 7.93-7.79 (m, 5H), 7.40 (br s, 1H), 4.54 (d, J=5.6 Hz, 2H); LC-MS: 99.48%; 513.1 (M$^+$+1); (column; Ascentis Express C18, (50×3.0 mm, 2.7 μm); RT 1.77 min. 0.025% Aq. TFA+5% ACN: ACN+5% 0.025% Aq. TFA, 1.2 mL/min). HPLC (purity): 99.35%; (column; X-select CSH—C18 (150×4.6 mm, 3.5 μm); RT 5.45 min. 0.05% TFA (Aq)+5% ACN: ACN+5% 0.05% TFA (Aq): 1.0 mL/min, Diluent: DMSO: ACN: water).

Example 19: Synthesis of 869 & 870

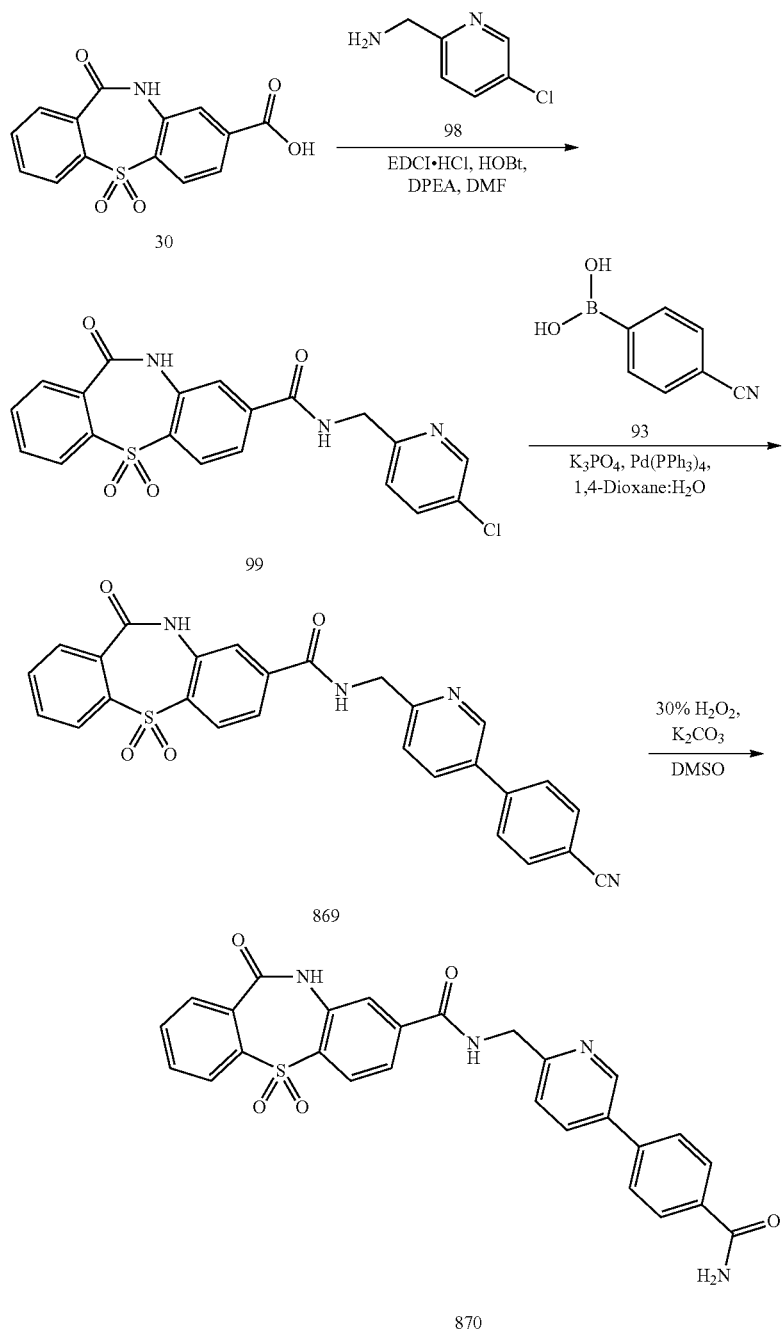

Synthesis of N-((5-chloropyridin-2-yl) methyl)-11-oxo-10,11-dihydrodibenzo[b,f][1, 4]thiazepine-8-carboxamide 5,5-dioxide (99)

To a stirring solution of 30 (1 g, 3.30 mmol) in DMF (20 mL) under inert atmosphere were added EDCI.HCl (945 g, 4.90 mmol), HOBt (668 mg, 4.95 mmol), ((5-chloropyridin-2-yl) methanamine 98 (470 mg, 3.30 mmol) and diisopropylethylamine (1.63 mL, 9.90 mmol) at 0° C.; warmed to RT and stirred for 16 h. The reaction was monitored by TLC; after completion of the reaction, the reaction mixture was diluted with ice-cold water (50 mL) and extracted with EtOAc (2×50 mL). The combined organic extracts were dried over sodium sulfate, filtered and concentrated in vacuo to obtain the crude. The crude was purified through silica gel column chromatography using 2-3% MeOH/CH$_2$Cl$_2$ to afford compound 99 (1.2 g, 85%) as an off-white solid. TLC: 10% MeOH/CH$_2$Cl$_2$ (R$_f$: 0.5); $^1$H NMR (DMSO-d$_6$, 500 MHz): δ 9.37 (t, J=5.8 Hz, 1H), 8.55 (d, J=2.3 Hz, 1H), 8.07 (d, J=8.7 Hz, 1H), 8.01-7.94 (m, 3H), 7.93-7.83 (m, 5H), 7.36 (d, J=8.7 Hz, 1H), 4.55 (d, J=6.1 Hz, 2H); (NMR shows DMF solvent) LC-MS: 50.51%; 427.9 (M$^+$+1); (column;

Ascentis Express C18, (50×3.0 mm, 2.7 μm); RT 2.09 min. 0.025% Aq. TFA+5% ACN: ACN+5% 0.025% Aq. TFA, 1.2 mL/min).

Synthesis of N-((5-(4-cyanophenyl) pyridin-2-yl) methyl)-11-oxo-10,11-dihydrodibenzo[b, f][1,4] thiazepine-8-carboxamide 5,5-dioxide (869)

To a stirring solution of compound 99 (1 g, 2.34 mmol) in 1, 2-dimethoxy ethane: H₂O (4:1, 30 mL) under argon atmosphere were added (4-cyanophenyl) boronic acid 93 (378 mg, 2.57 mmol) and potassium phosphate (1.49 g, 7.02 mmol) at RT and purged under argon atmosphere for 15 min. To this was added Pd(PPh₃)₄ (171 mg, 0.23 mmol) and heated to 140° C. and stirred for 24 h. The reaction was monitored by TLC; after completion of the reaction, the reaction mixture was diluted with ice-cold water (100 mL) and extracted with EtOAc (2×100 mL). The combined organic extracts were dried over sodium sulfate, filtered and concentrated in vacuo to obtain the crude. The crude was purified through silica gel column chromatography using 1-4% MeOH/CH₂Cl₂ and triturated with 5% MeOH/CH₂Cl₂ (5 mL), n-pentane (20 mL) to afford 869 (150 mg, 13%) as an off-white solid. TLC: 10% MeOH/CH₂Cl₂ (R$_f$: 0.5); ¹H NMR (DMSO-d₆, 400 MHz): δ 11.53 (s, 1H), 9.41 (br t, J=5.7 Hz, 1H), 8.90 (d, J=2.3 Hz, 1H), 8.13 (dd, J=8.2, 2.4 Hz, 1H), 8.08 (d, J=8.5 Hz, 1H), 8.02-7.84 (m, 10H), 7.44 (d, J=8.2 Hz, 1H), 4.62 (d, J=5.8 Hz, 2H); LC-MS (Agilent 6310 Ion Trap): 97.40%; 493.3 (M-1)⁺; (column; X-select CSH C-18, (50×3.0 mm, 2.7 μm); RT 3.55 min. 2.5 mM NH₄OAc: ACN, 0.8 mL/min); HPLC (purity): 97.49%; (column; X-select CSH C-18 (150×4.6 mm, 3.5 μm); RT 7.89 min. min. ACN+5% 0.05% TFA: 0.05% TFA+5% ACN; 1.0 mL/min; Diluent: DMSO: ACN: water).

Synthesis of N-((5-(4-carbamoylphenyl) pyridin-2-yl) methyl)-11-oxo-10, 11-dihydrodibenzo[b,f][1,4] thiazepine-8-carboxamide 5,5-dioxide (870)

To a stirring solution of 869 (100 mg, 0.20 mmol) in DMSO (10 mL) were added 30% aqueous H₂O₂ (1 mL) and potassium carbonate (139 mg, 1.00 mmol) at 0° C.; warmed to RT and stirred for 4 h. The reaction was monitored by TLC; after completion of the reaction, the reaction mixture diluted with water (10 mL) and stirred for 30 min. The precipitated solid was filtered, washed with water (100 mL) and dried in vacuo to afford 870 (80 mg, 77%) as an off-white solid. TLC: 10% MeOH/CH₂Cl₂ (R$_f$: 0.2); ¹H-NMR (DMSO-d₆, 400 MHz): δ 11.53 (br s, 1H), 9.37 (br t, J=6.0 Hz, 1H), 8.87 (s, 1H), 8.10 (dd, J=8.2, 2.4 Hz, 1H), 8.03 (br d, J=8.2 Hz, 2H), 8.00-7.92 (m, 4H), 7.88 (td, J=7.5, 1.3 Hz, 1H), 7.85-7.77 (m, 5H), 7.41 (d, J=8.2 Hz, 2H), 4.61 (d, J=5.8 Hz, 2H); LC-MS: 98.77%; 513.1 (M+1)⁺; (column; Kinetex EVO C-18 (50×3.0 mm, 2.6 um); RT 2.09 min. 2.5 mM Aq. NH₄OOCH+5% ACN: ACN+5% 2.5 mM Aq.NH₄OOCH, 0.8 mL/min); HPLC (purity): 98.72%; (column; X-select CSH C-18 (150×4.6 mm, 3.5 μm); RT 5.96 min. min. ACN+5% 0.05% TFA: 0.05% TFA+5% ACN; 1.0 mL/min; Diluent: DMSO: ACN: water).

Example 20: Synthesis of 872

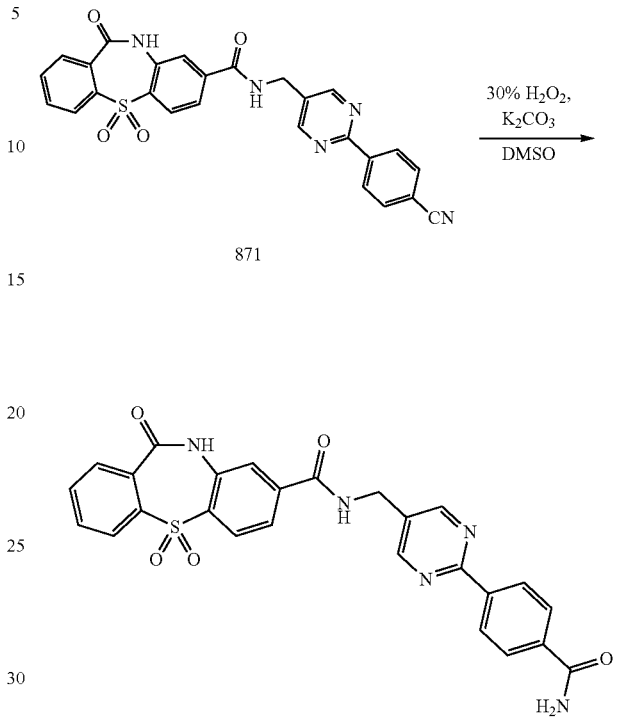

Synthesis of N-((2-(4-carbamoylphenyl) pyrimidin-5-yl) methyl)-11-oxo-10, 11-dihydrodibenzo[b,f][1, 4]thiazepine-8-carboxamide 5,5-dioxide (872)

To a stirring solution of N-((2-(4-cyanophenyl) pyrimidin-5-yl) methyl)-11-oxo-10, 11-dihydrodibenzo[b,f][1,4] thiazepine-8-carboxamide 5,5-dioxide 871 (70 mg, 0.14 mmol) in DMSO (2 mL) were added 30% H₂O₂ (0.16 mL, 1.4 mmol) and potassium carbonate (97 mg, 0.7 mmol) at 0° C. warmed to RT and stirred for 3 h. The reaction was monitored by TLC; after completion of the reaction, the reaction mixture was diluted with water (100 mL) and the precipitated solid was filtered, washed with hexane (2×10 mL) and dried in vacuo to afford 872 (62 mg, 86%) as white solid. TLC: 10% MeOH/CH₂Cl₂ (R$_f$: 0.6); ¹H-NMR (DMSO-d₆, 400 MHz): δ 11.52 (s, 1H), 9.36 (t, J=5.6 Hz, 1H), 8.89 (s, 2H), 8.42 (d, J=8.4 Hz, 2H), 8.09-7.81 (m, 10H), 7.45 (br s, 1H), 4.55 (d, J=5.4 Hz, 2H); LC-MS: 99.02%; 514.1 (M⁺+1); (column; Ascentis Express C18, (50×3.0 mm, 2.7 μm); RT 1.86 min. 0.025% Aq. TFA+5% ACN: ACN+5% 0.025% Aq. TFA, 1.2 mL/min); HPLC (purity): 99.38%; (column; X select CSH C-18 (150×4.6 mm, 3.5 μm); RT 6.99 min. ACN+5% 0.05% TFA (Aq): 0.05% TFA (Aq)+5% ACN; 1.0 mL/min, Diluent: DMSO: ACN: water).

Example 21: Synthesis of 825

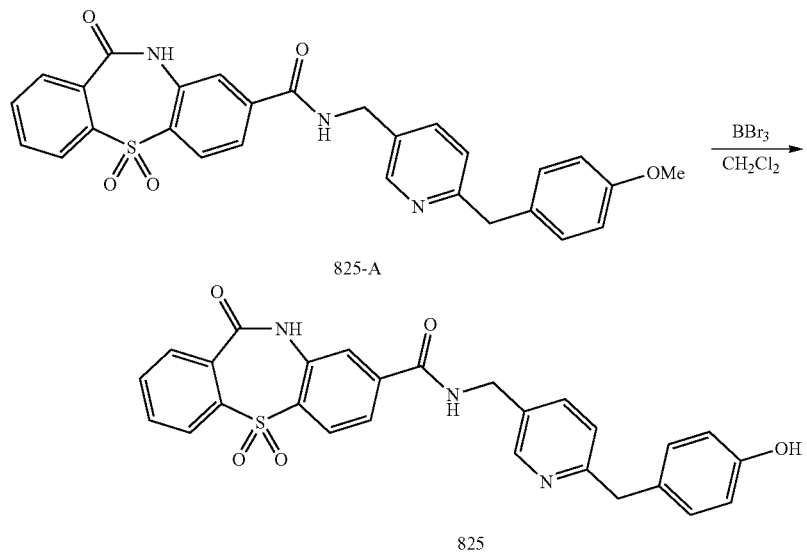

Synthesis of N-((6-(4-hydroxybenzyl) pyridin-3-yl) methyl)-11-oxo-10,11-dihydrodibenzo[b,f][1,4]thiazepine-8-carboxamide 5,5-dioxide (825)

To a stirring solution of N-((6-(4-methoxybenzyl) pyridin-3-yl) methyl)-11-oxo-10, 11-dihydrodibenzo[b,f][1,4]thiazepine-8-carboxamide 5,5-dioxide (825-A) (150 mg, 0.29 mmol) in CH$_2$Cl$_2$ (20 mL) under inert atmosphere was added BBr$_3$ (0.27 mL, 2.95 mmol) at 0° C.; warmed to RT and stirred for 16 h. The reaction was monitored by TLC; after completion of the reaction, the reaction mixture was poured into ice-cold water (10 mL), the pH of the aqueous layer was neutralized with 10% NaHCO$_3$ solution and extracted with EtOAc (2×150 mL). The combined organic extracts were dried over sodium sulfate, filtered and concentrated in vacuo to obtain the crude. The crude was purified through silica gel column chromatography using 3% MeOH/CH$_2$Cl$_2$ to afford 825 (105 mg, 72%) as an off-white solid. TLC: 7% MeOH/CH$_2$Cl$_2$ (R$_f$: 0.5); $^1$H NMR (DMSO-d$_6$, 400 MHz): δ 11.44 (br s, 1H), 9.17 (br s, 2H), 8.41 (s, 1H), 7.90 (t, J=8.8 Hz, 2H), 7.87-7.79 (m 2H), 7.77-7.71 (m, 1H), 7.69 (br s, 1H), 7.58 (dd, J=18.0, 1.8 Hz, 2H), 7.15 (d, J=7.9 Hz, 1H), 7.02 (d, J=8.4 Hz, 2H), 6.64 (d, J=8.3 Hz, 2H), 4.41 (d, J=5.6 Hz, 2H), 3.91 (s, 2H); LC-MS: 98.61%; 500.1 (M$^+$+1); (column; Ascentis Express C18, (50×3.0 mm, 2.7 μm); RT 1.75 min. 0.025% Aq. TFA+5% ACN: ACN+ 5% 0.025% Aq. TFA, 1.2 mL/min); HPLC (purity): 98.17%; (column; X-select CSH C-18 (150×4.6 mm, 3.5 μm); RT 5.45 min. 0.05% TFA+5% ACN: ACN+5% 0.05% TFA; 1.0 mL/min, Diluent: DMSO:ACN:water).

Example 22: Synthesis of 837

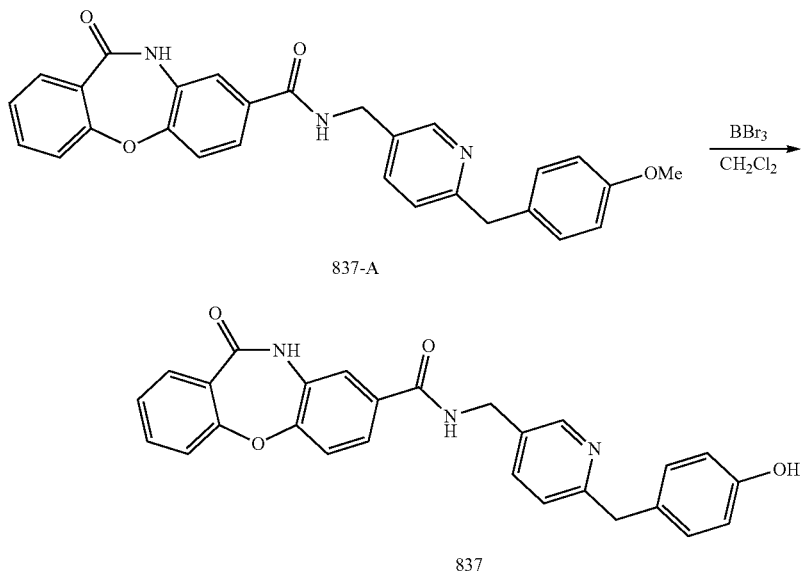

Synthesis of N-((6-(4-hydroxybenzyl)pyridin-3-yl)methyl)-11-oxo-10,11-dihydrodibenzo[b,f][1,4]oxazepine-8-carboxamide (837)

To a stirring solution of N-((6-(4-methoxybenzyl) pyridin-3-yl) methyl)-11-oxo-10, 11-dihydrodibenzo[b,f][1,4]oxazepine-8-carboxamide (837-A) (120 mg, 0.25 mmol) in $CH_2Cl_2$ (10 mL) under inert atmosphere was added $BBr_3$ (0.24 mL, 2.58 mmol) at 0° C.; warmed to RT and stirred for 16 h. The reaction was monitored by TLC; after completion of the reaction, the reaction mixture was poured into ice-cold water (10 mL), the pH of the aqueous layer was neutralized with 10% $NaHCO_3$ solution and extracted with EtOAc (2×100 mL). The combined organic extracts were dried over sodium sulfate, filtered and concentrated in vacuo to obtain the crude. The crude was triturated with MeOH (5 mL) and dried in vacuo to afford 837 (80 mg, 69%) as an off-white solid. TLC: 7% $MeOH/CH_2Cl_2$ ($R_f$: 0.5); $^1H$ NMR (DMSO-$d_6$, 400 MHz): δ 10.60 (br s, 1H), 9.15 (br s, 1H), 9.01 (t, J=5.8 Hz, 1H), 8.41 (s, 1H), 7.78 (dd, J=7.8, 1.6 Hz, 1H), 7.69-7.55 (m, 4H), 7.41 (d, J=8.4 Hz, 1H), 7.38-7.31 (m, 2H), 7.16 (d, J=7.9 Hz, 1H), 7.02 (d, J=8.5 Hz, 2H), 6.65 (d, J=8.5 Hz, 2H), 4.41 (d, J=5.8 Hz, 2H), 3.91 (s, 2H); LC-MS: 99.74%; 452.1 ($M^+$+1); (column; Ascentis Express C18, (50×3.0 mm, 2.7 µm); RT 1.75 min. 0.025% Aq. TFA+5% ACN: ACN+5% 0.025% Aq. TFA, 1.2 mL/min); HPLC (purity): 98.92%; (column; X-select CSH C-18 (150×4.6 mm, 3.5 µm); RT 5.45 min. 0.05% TFA+5% ACN: ACN+5% 0.05% TFA; 1.0 mL/min, Diluent: DMSO: ACN:water).

Example 23: Assay Measuring Activity of Compounds on Viral Production in and on Viability of AD38 Cells AD38 cells grown in a 175 cm flask with "Growth Medium" (DMEM/F12 (1:1) (cat# SH30023.01, Hyclone, 1× Pen/step (cat#: 30-002-CL, Mediatech, Inc), 10% FBS (cat#: 101, Tissue Culture Biologics), 250 µg/mL G418 (cat#: 30-234-CR, Mediatech, Inc), 1 µg/mL Tetracycline (cat#: T3325, Teknova)) were detached with 0.25% trypsin. Tetracycline-free "treatment medium" (15 mL DMEM/F12 (1:1) (cat# SH30023.01, Hyclone, lx Pen/step (cat#: 30-002-CL, Mediatech, Inc), with 2% FBS, Tet-system approved (cat#: 631106, Clontech) were then added to mix and spun at 1300 rpm for 5 min. Pelleted cells were then re-suspended/washed with 50 mL of 1×PBS 2 times and 10 mL Treatment Medium one time. AD38 cells were then re-suspended with 10 mL of Treatment Medium and counted. Wells of a collagen coated 96-well NUNC microtiter plate were seeded at 50,000/well in 180 µL of Treatment Medium, and 20 µL of in treatment media with either 10% DMSO (Control) or a 10× solution of compound in 10% DMSO was added. Plates were incubated for 6 days at 37° C.

Viral load production was assayed by quantitative PCR of the core sequence. Briefly, 5 µL of clarified supernatant was added to a PCR reaction mixture that contained forward primers HBV-f 5'-CTGTGCCTTGGGTGGCTTT-3', Reverse primers HBV-r 5'-AAGGAAAGAAGTCAGAAGGCAAAA-3' and Fluorescent TaqMan Probes HBV-probe 5'-FAM/AGCTCCAAA/ZEN/TTCTTTATAAGGGTCGAT-GTCCATG/3IABkFQ-3' in Quanta Biosciences PerfeCTa® qPCR Toughmix®, and was subsequently on an Applied Biosystems VIIA7 in a final volume of 20 µL. The PCR mixture was incubated at 45° C. for 5 minutes, then 95° C. for 10 min, followed by 40 cycles of 10 seconds at 95° C. and 20 seconds at 60° C. Viral load was quantitated against known standards by using ViiA™ 7 Software. Viral load in the supernatant from wells with treated cells were compared against viral load in supernatant from DMSO control wells (≥3 per plate).

At the end of compound treatment period cell viability was assessed using a Promega CellTiter-Glo protocol. All supernatant was removed the previously treated 96-well microtiter plate, and 50 µL Tetracycline-free treatment medium (DMEM/F12 (1:1), 1× Pen/step (cat#: 30-002-CL, Mediatech, Inc), with 2% FBS, Tet-system approved (cat#: 631106, Clontech), and 1% DMSO was added back to each well. Another 50 µL of CellTiter-Glo reagent solution (Promega, G7573) was then added at room temperature and the contents mixed for 2 minutes on an orbital shaker to induce cell lysis. This was followed by incubation at room temperature for 10 minutes to stabilize the luminescent signal. The luminescence was recorded for 0.2 seconds per well on a Tecan multimode platereader (Infinite M1000 pro). The luminescent signal from each well was normalized against that of untreated (DMSO) control wells. All results in Table 3 were reported with percent viability (with controls being 100%).

TABLE 3

Compounds and Biological activity

| Compound Number | AD38 Viral Load (%) (VL with cmpd/VL in DMSO control) at 10 µM | AD38 Viability Normalized Result (cmpd/DMSO %) at 10 µM |
|---|---|---|
| 495 | 23.1 | 96 |
| 497 | 38.7 | 97 |
| 504 | 62.9 | 101 |
| 506 | 31.6 | 100 |
| 505 | 48.2 | 103 |
| 507 | 51.9 | 103 |
| 545 | 1.4 | 95 |
| 547 | 1.5 | 99 |
| 540 | 0.6 | 52 |
| 539 | 0.2 | 0 |
| 542 | 1.6 | 106 |
| 543 | 1.2 | 24 |
| 778 | 3.2 | 104 |
| 780 | 1.8 | 106 |
| 782 | 25.4 | 108 |
| 779 | 0.5 | 87 |
| 781 | 7.3 | 102 |
| 786 | 5.0 | 105 |
| 784 | 137.3 | 103 |
| 785 | 2.1 | 94 |
| 783 | 6.3 | 105 |
| 787 | 15.5 | 100 |
| 807 | 0.9 | 96 |
| 843 | 18.8 | 103 |
| 739 | 62.2 | 108 |
| 788 | 1.9 | 111 |
| 789 | 0.4 | 108 |
| 796 | 1.4 | 111 |
| 844 | 10.2 | 103 |
| 791 | 2.2 | 100 |
| 794 | 1.3 | 104 |
| 867 | 0.6 | 86 |
| 875 | 26.1 | 108 |
| 868 | 27.7 | 103 |
| 792 | 23.1 | 105 |
| 793 | 3.5 | 103 |
| 795 | 6.4 | 106 |
| 790 | 1.7 | 103 |
| 871 | 1.3 | 96 |
| 872 | 5.2 | 104 |
| 869 | 13.3 | 83 |
| 870 | 82.7 | 106 |
| 837-A | 5.6 | 105 |
| 825 | 6.6 | 90 |
| 825-A | 6.2 | 58 |

TABLE 3-continued

Compounds and Biological activity

| Compound Number | AD38 Viral Load (%) (VL with cmpd/VL in DMSO control) at 10 μM | AD38 Viability Normalized Result (cmpd/DMSO %) at 10 μM |
|---|---|---|
| 837 | 0.9 | 108 |
| 876 | 65.5 | 101 |

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A compound represented by:

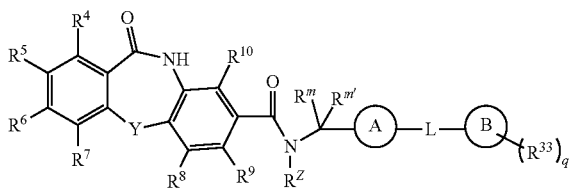

wherein

Y is $S(O)_y$, wherein y is 2;
$R^Z$ is H;
$R^{m'}$ and $R^m$ are each H;
L is a bond or $C_{1-2}$alkylene (optionally substituted by halogen or $C_{1-2}$alkyl);
A is a 5-7 membered monocyclic heterocyclic or 5-6 membered monocyclic heteroaryl ring optionally substituted by one or two substituents selected from the group consisting of halogen, hydroxyl, cyano, $C_{1-6}$alkyl, $C_{2-6}$alkenyl, $C_{2-6}$alkynyl, $C_{1-6}$alkoxy, and NR'R";
B is selected from the group consisting of phenyl (optionally substituted by one, two or three substituents represented by $R^{33}$), 5-6 membered monocyclic heteroaryl optionally substituted by one, two or three substituents represented by $R^{33}$), and 9-10 membered bicyclic heteroaryl (optionally substituted by one, two or three substituents represented by $R^{33}$);

R' is selected, independently for each occurrence, from H, methyl, ethyl, and propyl;

R" is selected, independently for each occurrence, from H, methyl, ethyl, propyl, (optionally substituted by hydroxyl), butyl (optionally substituted by hydroxyl), —C(O)-methyl and —C(O)-ethyl, or R' and R" taken together with the nitrogen to which they are attached may form a 4-7 membered heterocycle optionally substituted by one, two or more substituents selected from the group consisting of halogen, hydroxyl, $NH_2$, —C(O)—O—$C_{1-3}$alkyl, —C(O)—$C_{1-3}$alkyl, carboxy, oxo, and $C_{1-3}$alkyl;

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R";

$R^{33}$ is independently selected for each occurrence from the group consisting of H, halogen, hydroxyl, nitro, cyano, $C_{1-6}$alkyl, —C(O)—O—$C_{1-6}$alkyl, —C(O)—NR'R", —C(=NH)—NR'R", $C_{2-6}$alkenyl, $C_{2-6}$alkynyl, $C_{1-6}$alkoxy, carboxy, —CHO, NR'R", —C(O)—$C_{1-6}$alkyl, —C(O)—$C_{1-6}$ alkoxy, $C_{3-6}$cycloalkyl, —S(O)$_w$—$C_{1-6}$alkyl (where w is 0, 1 or 2), —S(O)$_w$—NR'R" (where w is 0, 1 or 2), and —NR'—S(O)$_w$—$C_{1-6}$alkyl (where w is 0, 1 or 2);

q is 0, 1, 2 or 3;

wherein for each occurrence, $C_{1-6}$alkyl may be optionally substituted with one, two, three or more substituents selected from the group consisting of halogen, hydroxyl, nitro, cyano, carboxy, $C_{2-6}$alkenyl, $C_{2-6}$alkynyl, $C_{1-6}$alkoxy, NR'R", —NR'—S(O)$_w$— $C_{1-6}$alkyl (where w is 0, 1 or 2), and S(O)$_w$—NR'R" (where w is 0, 1 or 2); $C_{1-6}$alkoxy may be optionally substituted with one, two, three or more substituents selected from the group consisting of halogen, hydroxyl, nitro, cyano, carboxy, $C_{1-6}$alkyl, NR'R", —NR'—S(O)$_w$— $C_{1-6}$alkyl (where w is 0, 1 or 2), and S(O)$_w$—NR'R" (where w is 0, 1 or 2); and pharmaceutically acceptable salts thereof.

2. The compound of claim 1, wherein the compound is represented by:

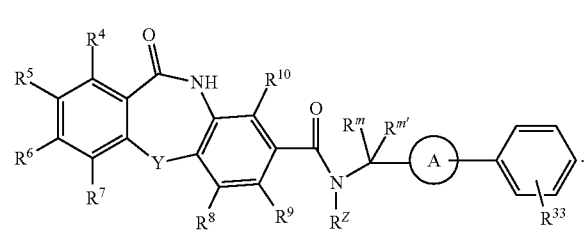

3. The compound of claim 2, wherein A is a 5-6 membered monocyclic heteroaryl.

4. The compound of claim 2, wherein A is pyridinyl.

5. The compound of claim 2, wherein A is pyrimidinyl.

6. The compound of claim 2, wherein A is thiadiazole.

7. The compound of claim 2, wherein each of moieties $R^4$, $R^5$, $R^6$, $R^7$, $R^8$, $R^9$, and $R^{10}$ is independently selected for each occurrence from the group consisting of hydrogen, methyl, trifluoromethyl, and halogen.

8. The compound of claim 7, wherein each of moieties $R^4$, $R^5$, $R^6$, $R^7$, $R^8$, $R^9$, and $R^{10}$ is hydrogen.

9. The compound of claim 2, wherein A is optionally substituted by one substituent selected from the group consisting of halogen, $C_{1-6}$haloalkyl, and $C_{1-6}$alkyl.

10. The compound of claim 2, wherein $R^{33}$ is selected from the group consisting of H, halogen, hydroxyl, cyano, $C_{1-6}$alkyl, —C(O)—O—$C_{1-6}$alkyl, —C(O)—NR'R", $C_{1-6}$alkoxy, carboxy, CHO, NR'R", and —$C_{1-6}$alkyl-OH.

11. The compound of claim 2, wherein L is a bond or a methylene.

12. The compound of claim 2, wherein LB is a bond.

13. The compound of claim 2, wherein B is selected from the group consisting of phenyl, indolyl, indazolyl, benzimidazolyl, and pyrimidinyl, each of which may be optionally substituted by one, two or three substituents represented by $R^{33}$.

14. The compound of claim 2, wherein q is 1.

15. A pharmaceutically acceptable composition comprising a compound of claim 2, and a pharmaceutically acceptable excipient.

16. A method of treating a hepatitis B infection in a patient in need thereof, comprising administering an effective amount of a compound of claim 2.

* * * * *